US012780935B2

(12) United States Patent
Viswanathan et al.

(10) Patent No.: US 12,780,935 B2
(45) Date of Patent: Nov. 3, 2026

(54) TREATMENT OF COMPLEMENT MEDIATED DISEASES AND DISORDERS WITH C3B ANTIBODIES

(71) Applicant: Visterra, Inc., Waltham, MA (US)

(72) Inventors: Karthik Viswanathan, Waltham, MA (US); Ramki Ramakrishnan, Waltham, MA (US); Hedy Adari, Waltham, MA (US); Feng Gao, Waltham, MA (US); Andrew Wollacott, Waltham, MA (US)

(73) Assignee: Visterra, Inc., Waltham, MA (US)

( * ) Notice: Subject to any disclaimer, the term of this patent is extended or adjusted under 35 U.S.C. 154(b) by 472 days.

(21) Appl. No.: 18/470,726

(22) Filed: Sep. 20, 2023

(65) Prior Publication Data

US 2024/0132617 A1 Apr. 25, 2024
US 2024/0228652 A9 Jul. 11, 2024

Related U.S. Application Data

(60) Provisional application No. 63/376,305, filed on Sep. 20, 2022.

(51) Int. Cl.
*C07K 16/28* (2006.01)
*A61P 21/00* (2006.01)

(52) U.S. Cl.
CPC .......... *C07K 16/2896* (2013.01); *A61P 21/00* (2018.01); *C07K 2317/52* (2013.01); *C07K 2317/565* (2013.01)

(58) Field of Classification Search
CPC ............ C07K 16/2896; C07K 2317/52; C07K 2317/565; C07K 2317/569; C07K 2317/76; A61P 37/06; A61K 2039/505
See application file for complete search history.

(56) References Cited

U.S. PATENT DOCUMENTS

| | | | |
|---|---|---|---|
| 6,737,056 | B1 | 5/2004 | Presta |
| 7,083,784 | B2 | 8/2006 | Dall et al. |
| 7,183,387 | B1 | 2/2007 | Presta |
| 7,790,858 | B2 | 9/2010 | Presta |
| 8,192,742 | B2 | 6/2012 | Bansal |
| 8,323,962 | B2 | 12/2012 | Dall'acqua et al. |
| 8,377,437 | B2 | 2/2013 | Van |
| 9,243,060 | B2 | 1/2016 | Bansal |
| 9,890,377 | B2 | 2/2018 | Igawa et al. |
| 10,183,989 | B2 | 1/2019 | Bansal |
| 10,556,949 | B2 | 2/2020 | Igawa et al. |
| 10,858,420 | B2 | 12/2020 | Bansal |
| 11,371,039 | B2 | 6/2022 | Igawa et al. |
| 2009/0081211 | A1 | 3/2009 | Campagne |
| 2009/0175875 | A1 | 7/2009 | Etemad-gilbertson et al. |
| 2010/0291106 | A1 | 11/2010 | Etemad-gilbertson et al. |
| 2016/0008427 | A1 | 1/2016 | Sidhu et al. |
| 2016/0244513 | A1 | 8/2016 | Bansal |
| 2019/0031747 | A1 | 1/2019 | Bansal |
| 2019/0185557 | A1 | 6/2019 | Igawa et al. |
| 2019/0233525 | A1 | 8/2019 | Igawa et al. |
| 2020/0181257 | A1 | 6/2020 | Kuramochi et al. |
| 2021/0070860 | A1 | 3/2021 | Marasco et al. |
| 2021/0115147 | A1 | 4/2021 | Chamberlain et al. |
| 2021/0253682 | A1 * | 8/2021 | Stub ..................... A61K 9/0019 |

FOREIGN PATENT DOCUMENTS

| | | | |
|---|---|---|---|
| EP | 2841453 | A1 | 3/2015 |
| EP | 2552955 | B1 | 5/2017 |
| EP | 3524620 | A1 | 8/2019 |
| EP | 2352521 | B1 | 9/2020 |
| EP | 2698431 | B1 | 9/2020 |
| EP | 2666787 | B1 | 2/2022 |
| JP | 5415624 | B2 | 11/2013 |
| JP | 6122072 | B2 | 4/2017 |
| JP | 6745858 | B2 | 8/2020 |
| JP | 2021518411 | A | 8/2021 |
| JP | 7012104 | B2 | 1/2022 |
| WO | 2009125825 | A1 | 10/2009 |
| WO | 2011122011 | A2 | 10/2011 |
| WO | 2012073992 | A1 | 6/2012 |
| WO | 2012115241 | A1 | 8/2012 |
| WO | 2012133782 | A1 | 10/2012 |
| WO | 2013118858 | A1 | 8/2013 |
| WO | 2019227102 | A1 | 11/2019 |
| WO | 2019238674 | A1 | 12/2019 |
| WO | 2020123662 | A2 | 6/2020 |

OTHER PUBLICATIONS

International Search Report for PCT/US2023/074656 dated Apr. 18, 2024 (9 pages).

Albert, Thilo , et al., "The B-cell epitope of the monoclonal anti-factor VIII antibody ESH8 characterized by peptide array analysis", Thrombosis and Haemostasis, vol. 99, No. 03, 2008, pp. 634-637, DOI: 10.1160/TH07-06-0400, (4 pages).

Altschul , et al., "Basic Local Alignment Search Tool", J. Mol. Biol., vol. 215, No. 3, 1990, pp. 403-410 (8 pages).

Altschul , et al., "Gapped Blast and PSI-Blast: a new generation of protein database search programs", Nucleic Acids Research, vol. 25, No. 17, Sep. 1, 1997, pp. 3389-3402, DOI: 10.1093/nar/25.17.3389, (14 pages).

Altschul , et al., "Local Alignment Statistics", Methods in Enzymology, vol. 266, 1996, pp. 460-480 (21 pages).

Coales, Stephen J., et al., "Epitope mapping by amide hydrogen/deuterium exchange coupled with immobilization of antibody, on-line proteolysis, liquid chromatography and mass spectrometry", Rapid Communications in Mass Spectrometry, vol. 23, No. 5, Mar. 15, 2009, pp. 639-647, DOI: 10.1002/rcm.3921.

(Continued)

*Primary Examiner* — Laura B Goddard
*Assistant Examiner* — Alyssa Rae Stonebraker
(74) *Attorney, Agent, or Firm* — Proskauer Rose LLP

(57) ABSTRACT

The present invention provides, among other things, anti-C3b antibodies with increased specificity and potency and methods of treating C3 glomerulopathy and other complement mediated diseases and disorders using the same.

26 Claims, 11 Drawing Sheets

Specification includes a Sequence Listing.

(56) References Cited

OTHER PUBLICATIONS

Cunningham & Wells , "High Resolution Epitope Mapping of hGH-Receptor Interactions by Alanine-Scanning Mutagenesis", Dept. of Biomolecular Chemistry, Genentech, Science, 1989, vol. 244, pp. 1081-1085.
Deisenhofer, Johann , "Crystallographic refinement and atomic models of a human Fc fragment and its complex with fragment B of protein A from *Staphylococcus aureus* at 2.9- and 2.8-.ANG. Resolution", Biochemistry vol. 20 No. 9, 1981, pp. 2361-2370, DOI: 10.1021/bi00051a001.
Fisher, Adam , et al., "Efficient isolation of soluble intracellular single-chain antibodies using the twin-arginine translocation machinery", Journal of Molecular Biology, vol. 385, No. 1, Jan. 9, 2009, pp. 299-311, DOI: 10.1016/j.jmb.2008.10.051 (23 pages).
Gerhardt, Stefan , et al., "Structure of IL-17A in Complex with a Potent, Fully Human Neutralizing Antibody", Journal of Molecular Biology, vol. 394, No. 5, Dec. 18, 2009, pp. 905-921, DOI: 10.1016/j.jmb.2009.10.008.
Ghetie, Victor , et al., "Multiple Roles for the Major Histocompatibility Complex Class I-Related Receptor FcRn", Annual Reviews of Immunology, vol. 18, Apr. 2000, pp. 739-766, DOI: 10.1146/annurev.immunol.18.1.739 (30 pages).
Harris, Claire L., et al., "Developments in anti-complement therapy; from disease to clinical trial", Molecular Immunology, vol. 102, Aug. 16, 2018 (16 pages).
Ito, Naoko , et al., "C3 glomerulopathy and current dilemmas", Clinical and Experimental Nephrology, Japanese Society of Nephrology, vol. 21, No. 4, Nov. 23, 2016 (6 pages).
Jefferis, Roy , et al., "Interaction sites on human IgG-Fc for FcγR: current models", Immunology Letters, vol. 82, No. 1-2, Jun. 2002, pp. 57-65, DOI: 10.1016/S0165-2478(02)00019-6.
Jia, Xiao-Chi , et al., "A novel method of Multiplexed Competitive Antibody Binning for the characterization of monoclonal antibodies", Journal of Immunological Methods, vol. 288, No. 102, May 2004, pp. 91-98, 10.1016/j.jim.2004.02.010.
Kirkland, Theo N., et al., "Analysis of the fine specificity and cross-reactivity of monoclonal anti-lipid A antibodies", Journal of Immunology, vol. 137, No. 11, 1986, pp. 3614-3619, DOI: 10.4049/jimmunol.137.11.3614 (7 pages).
Lasic, Dan D., "Novel applications of liposomes", Tibtech, vol. 16, Jul. 1998, pp. 307-321 (15 pages).
Lim, Al Ching , et al., "A Diversity of Antibody Epitopes Can Induce Signaling through the Erythropoietin Receptor", Biochemistry, vol. 49, No. 18, 2010, pp. 3797-3804, DOI: 10.1021/bi1001147.
Martin, W. Lance , et al., "Crystal Structure at 2.8 Å of an FcRn/Heterodimeric Fc Complex", Molecular Cell, vol. 7, Apr. 2001, pp. 867-877, DOI: (11 pages).
Maxwell, Kelly F., et al., "Crystal structure of the human leukocyte Fc receptor, FcγRIIa", Nature Structural Biology, vol. 6, 1999, pp. 437-442, DOI: 10.1038/8241.
Miller, Paul L., et al., "Epitope binning of murine monoclonal antibodies by a multiplexed pairing assay", Journal of Immunological Methods, vol. 365, Nos. 1-2, Feb. 28, 2011, pp. 118-125, DOI: 10.1016/j.jim.2010.12.021.
Morgan, William D., et al., "Precise Epitope Mapping of Malaria Parasite Inhibitory Antibodies by TROSY NMR Cross-Saturation", Biochemistry, vol. 44, No. 2, 2005, pp. 518-523, DOI: 10.1021/bi0482957.
Radaev, Sergei , et al., "The Structure of a Human Type III Fcγ Receptor in Complex with Fc", Journal of Biological Chemistry, vol. 276, No. 19, May 2001, pp. 16469-16477, DOI: 10.1074/jbc.M100350200 (9 pages).
Raghavan, Malini , et al., "Fc Receptors and Their Interactions with Immunoglobulins", Annual Review of Cell an Development Biology, vol. 12, 1996, pp. 181-220, DOI: 10.1146/annurev.cellbio.12.1.181.
Ravetch, Jeffrey V., et al., "IgG Fc Receptors", Annual Review of Immunology, vol. 19, Apr. 2001, pp. 275-290, DOI: 10.1146/annurev.immunol.19.1.275.
Rudikoff , et al., "Single amino acid substitution altering antigen-binding specificity", Proceedings of the National Academy of Sciences USA, Immunology, vol. 79, Mar. 1982, pp. 1979-1983 (5 pages).
Sauer-Eriksson , et al., "Crystal structure of the C2 fragment of streptococcal protein G in complex with the Fc domain of human IgG", Structure vol. 3 No. 3 (Mar. 15, 1995) pp. 265-278, DOI: 10.1016/s0969-2126(01)00157-5.
Sondermann, Peter , et al., "Crystal structure of the soluble form of the human Fcγ-receptor IIb: a new member of the immunoglobulin superfamily at 1.7 Å resolution", The EMBO Journal, vol. 18, No. 5, Mar. 1999, pp. 1095-1103, DOI: 10.1093/emboj/18.5.1095 (9 pages).
Sondermann, Peter , et al., "Molecular Basis for Immune Complex Recognition: A Comparison of Fc-Receptor Structures", Journal of Molecular Biology, vol. 309, No. 3, Jun. 2001, pp. 737-749, DOI: 10.1006/jmbi.2001.4670.
Sondermann, Peter , et al., "The 3.2-Å crystal structure of the human IgG1 Fc fragment-FcγRIII complex", Nature, vol. 406, 2000, pp. 267-273, DOI: 10.1038/35018508.
Song, Ruijiang , et al., "Epitope Mapping of Ibalizumab, a Humanized Anti-CD4 Monoclonal Antibody with Anti-HIV-1 Activity in Infected Patients", Journal of Virology, vol. 84, No. 14, Jul. 2010, pp. 6935-6942, DOI: 10.1128/JVI.00453-10 (8 pages).
Tashiro , et al., "Structures of bacterial immunoglobulin-binding domains and their complexes with immunoglobulins", Current Opinion in Structural Biology vol. 5 Issue 4 (Aug. 1995) pp. 471-481, DOI: 10,1016/0959-440X(95)80031-X.
Brown, Mckay, et al., "Tolerance of single, but not multiple, amino acid replacements in antibody VH CDR 2: a means of minimizing B cell wastage from somatic hypermutation?", The Journal of Immunology, vol. 156, No. 9, May 1, 1996, pp. 3285-3291, (8 pages).

* cited by examiner

TREATMENT OF COMPLEMENT MEDIATED DISEASES AND DISORDERS WITH C3B ANTIBODIES

CROSS REFERENCE TO RELATED APPLICATIONS

This application is claims priority to U.S. Provisional Patent Application No. 63/376,305, filed on Sep. 20, 2022, the entirety of which is hereby incorporated by reference.

INCORPORATION BY REFERENCE OF SEQUENCE LISTING

The instant application is being filed with an electronically filed Sequence Listing in XML format. The sequence listing file entitled SVI-002WO1_SL.xml was created on Sep. 19, 2023 and is 25 kilobytes in size. The information in the electronic format of the Sequence Listing is incorporated herein by reference in its entirety.

BACKGROUND

The complement system is a part of the innate immune system which does not adapt to changes over the course of the host's life but is recruited and used by the adaptive immune system. For example, it assists, or complements, the ability of antibodies and phagocytic cells to clear pathogens. This sophisticated regulatory pathway allows rapid reaction to pathogenic organisms while protecting host cells from destruction. Over thirty proteins and protein fragments make up the complement system. These proteins act through opsonization (enhancing phagocytosis of antigens), chemotaxis (attracting macrophages and neutrophils), cell lysis (rupturing membranes of foreign cells) and agglutination (clustering and binding of pathogens together).

The complement system has three pathways: classical, alternative and lectin. In the alternative pathway, C3, present in the blood stream, spontaneously cleaves at low rates into C3b and C3a. C3b is the larger of two elements and is considered an important part of the innate immune system. C3b is potent in opsonization: tagging pathogens, immune complexes (antigen-antibody), and apoptotic cells for phagocytosis. Additionally, C3b plays a role in forming a C3 convertase when bound to Factor B (C3bBb complex), or a C5 convertase when bound to C4b and C2b (C4b2b3b complex) or when an additional C3b molecule binds to the C3bBb complex (C3bBb3b complex). C3 glomerulopathy (C3G) is a rare disease that is characterized by accumulation of complement factors in the glomeruli due to overactivation and abnormal regulation of the alternative pathway (AP) of complement. Abnormal control of the AP of complement may be due to acquired or genetic abnormalities of the complement regulatory proteins. The deposition of complement factors drives glomerular inflammation, resulting in a proliferative glomerulonephritis. The most common diseases under the C3G umbrella are C3 Glomerulonephritis (C3GN), characterized by mesangial, subendothelial, and intramembranous deposits, and Dense Deposit Disease (DDD), characterized by dense deposits along the glomerular and tubular basement membranes.

SUMMARY OF THE INVENTION

The present invention provides, among other things, anti-C3b antibodies and antibody fragments with increased specificity to C3b and therapeutic uses of such antibodies in effectively treating complement mediated diseases, such as C3 glomerulopathy, dense deposit disease (DDD) and C3 glomerulonephritis (C3GN), wet age-related macular degeneration (wAMD), Passive Heymann Nephritis (NHP), and collagen-antibody induced arthritis (CAIA). In some embodiments, an anti-C3b antibody fragment is a VHH or VHH fused to an Fc domain. As described herein, the present invention is, in part, based on the identification of a new class of anti-C3b specific VHHs that have significantly reduced cross reactivity to C3. In particular, anti-C3b VHHs of the present invention are characterized with high binding affinity to C3b (e.g., with C3b $K_D$ less than 50 nM) and minimal cross-reactivity with C3 (e.g., with greater than 10 fold selectivity for C3b over C3). This is significant because C3b-antibodies and VHHs of the present invention selectively bind to C3b via, e.g., neoepitope on C3b, and can effectively target C3 convertase in diseased tissues without being saturated by high levels of circulating C3. As a result, C3b-antibodies of the present invention can be used at a lower dose to achieve therapeutic effect relative to the other anti-C3b antibodies or anti-C3 antibodies. This is demonstrated by the surprisingly high potency observed in functional assays, relative to prior-art antibodies, as described herein. Thus, the present invention provides inventive anti-C3b antibodies and VHHs that (i) inhibit the C3 convertase formation and mediate clearance of C3 deposits; (ii) target both solid phase and fluid phase alternative pathway C3 convertase activity; (iii) block C3b interaction with factor B (fB); (iv) inhibit activity specific to the alternative pathway (AP); (v) limit the interference of natural regulators of C3 convertase such as factor H (fH), DAF and other inhibitors; (vi) have favorable biophysical and pharmacokinetic properties to allow for prolonged therapeutic effect (biweekly or monthly dosing); and/or (vii) inhibit stabilization of C3 convertase by C3bNef autoantibodies. Inventive anti-C3b antibodies of the present invention promise a more potent treatment of complement mediated diseases and disorders.

In one aspect, the present invention provides, among other things, an antibody or antigen binding fragment thereof that binds to complement component 3b (C3b) comprising an amino acid sequence at least 90% identical to SEQ ID NO: 10.

In one aspect, the present invention provides, among other things, an antibody or antigen binding fragment thereof that binds to complement component 3b (C3b) comprising an amino acid sequence at least 90% identical to SEQ ID NO: 11.

In one aspect, the present invention provides, among other things, an antibody or antigen binding fragment thereof that binds to complement component 3b (C3b) comprising an amino acid sequence at least 90% identical to SEQ ID NO: 12.

In one aspect, the present invention provides, among other things, an antibody or antigen binding fragment thereof that binds to complement component 3b (C3b) comprising an amino acid sequence at least 90% identical to SEQ ID NO: 13.

In one aspect, the present invention provides, among other things, an antibody or antigen binding fragment thereof that binds to C3b comprising three complementarity determining regions (CDR1 to CDR3, respectively), wherein the CDR1 comprises NYHMG (SEQ ID NO: 16), CDR2 comprises TIIRTGETIYYADSVKG (SEQ ID NO: 17) and CDR3 comprises ATSGWNIKTVTPYEY (SEQ ID NO: 18).

In one aspect, the present invention provides, among other things, an antibody or antigen binding fragment thereof that binds to C3b comprising three complementarity determining regions (CDR1 to CDR3, respectively), wherein the CDR1 comprises GRTFSNY (SEQ ID NO: 19), CDR2 comprises IRTGET (SEQ ID NO: 20) and CDR3 comprises ATSGWNIKTVTPYEY (SEQ ID NO: 18).

In one aspect, the present invention provides, among other things, an antibody or antigen binding fragment thereof that binds to C3b comprising three complementarity determining regions (CDR1 to CDR3, respectively), wherein the CDR1 comprises NYHMG (SEQ ID NO: 16), CDR2 comprises TIIRTGKTIYYADSVKG (SEQ ID NO: 21) and CDR3 comprises ATSGWHIKTVTPYEY (SEQ ID NO: 22).

In one aspect, the present invention provides, among other things, an antibody or antigen binding fragment thereof that binds to C3b comprising three complementarity determining regions (CDR1 to CDR3, respectively), wherein the CDR1 comprises GRTFSNY (SEQ ID NO: 19), CDR2 comprises IRTGKT (SEQ ID NO: 23) and CDR3 comprises ATSGWHIKTVTPYEY (SEQ ID NO: 22).

In one aspect, the present invention provides, among other things, an antibody or antigen binding fragment thereof that binds to C3b comprising three complementarity determining regions (CDR1 to CDR3, respectively), wherein the CDR1 comprises NYHMG (SEQ ID NO: 16), CDR2 comprises TIIRTGTTIYYADSVKG (SEQ ID NO: 24) and CDR3 comprises ATSGWHIKTVTPYEY (SEQ ID NO: 22).

In one aspect, the present invention provides, among other things, an antibody or antigen binding fragment thereof that binds to C3b wherein the binding moiety comprises three complementarity determining regions (CDR1 to CDR3, respectively), wherein the CDR1 comprises GRTFSNY (SEQ ID NO: 19), CDR2 comprises IRTGTT (SEQ ID NO: 25) and CDR3 comprises ATSGWHIKTVTPYEY (SEQ ID NO: 22).

In one aspect, the present invention provides, among other things, an antibody or antigen binding fragment thereof that binds to C3b comprising three complementarity determining regions (CDR1 to CDR3, respectively), wherein the CDR1 comprises NYHMG (SEQ ID NO: 16), CDR2 comprises TIIRHGTTIYYADSVKG (SEQ ID NO: 26) and CDR3 comprises ATSGWHIKTVTPYEY (SEQ ID NO: 22).

In one aspect, the present invention provides, among other things, an antibody or antigen binding fragment thereof that binds to C3b wherein the binding moiety comprises three complementarity determining regions (CDR1 to CDR3, respectively), wherein the CDR1 comprises GRTFSNY (SEQ ID NO: 19), CDR2 comprises IRHGTT (SEQ ID NO: 27) and CDR3 comprises ATSGWHIKTVTPYEY (SEQ ID NO: 22).

In some embodiments, an antibody or antigen binding fragment thereof is a nanobody (VHH). In some embodiments, an antibody or antigen binding fragment thereof is a VHH fused to an Fc domain (VHH-Fc). In some embodiments, an antibody or antigen binding fragment thereof is a scFv. In some embodiments, an antibody or antigen binding fragment thereof is a Fab. In some embodiments, an antibody or antigen binding fragment thereof is a scFv fused to an Fc domain (scFv-Fc). In some embodiments, an antibody or antigen binding fragment thereof is a diabody. In some embodiments, an antibody or antigen binding fragment thereof is a minibody (scFv fused to CH3 domain of Fc). In some embodiments, an antibody or antigen binding fragment thereof is a scFab. In some embodiments, an antibody or antigen binding fragment thereof is a heavy chain antibody.

In some embodiments, a VHH comprises SEQ ID NO: 10. In some embodiments, a VHH comprises SEQ ID NO: 11. In some embodiments, a VHH comprises SEQ ID NO: 12. In some embodiments, a VHH comprises SEQ ID NO: 13.

In some embodiments, an antibody or antigen binding fragment thereof comprises an Fc domain. In some embodiments, an Fc domain is derived from IgG1. In some embodiments, an Fc domain is derived from IgG2. In some embodiments, an Fc domain is derived from IgG3. In some embodiments, an Fc domain is derived from IgG4.

In some embodiments, the Fc domain is modified. In some embodiments, the Fc domain is modified to increase half-life in vivo. In some embodiments, the Fc domain is modified to reduce immunogenicity in vivo.

In some embodiments, the Fc domain comprises T307Q mutation according to EU index numbering. In some embodiments, the Fc domain comprises Q331V mutation according to EU index numbering. In some embodiments, the Fc domain comprises A378V mutation according to EU index numbering. In some embodiments, the Fc domain comprises T307Q and Q331V mutations according to EU index numbering. In some embodiments, the Fc domain comprises T307Q mutation according to EU index numbering. In some embodiments, the Fc domain comprises T307Q and A378V mutations according to EU index numbering. In some embodiments, the Fc domain comprises Q331V and A378V mutations according to EU index numbering. In some embodiments, the Fc domain comprises T307Q, Q331V and A378V mutations according to EU index numbering.

In some embodiments, the Fc domain comprises S228P mutation according to EU index numbering.

In some embodiments, the Fc domain comprises a substitution at position F234 according to EU index numbering. In some embodiments, the Fc domain comprises a substitution at position L235 according to EU index numbering. In some embodiments, the Fc domain comprises a substitution at position D265 according to EU index numbering. In some embodiments, the Fc domain comprises a substitution at positions F234 and L235 according to EU index numbering. In some embodiments, the Fc domain comprises a substitution at positions F234 and D265 according to EU index numbering. In some embodiments, the Fc domain comprises a substitution at positions L235 and D265 according to EU index numbering. In some embodiments, the Fc domain comprises a substitution at positions F234, L235 and D265 according to EU index numbering.

In some embodiments, the substitution at position F234 is a hydrophobic amino acid. In some embodiments, the substitution at position F234 is a hydrophobic amino acid selected from a group consisting of alanine, valine, leucine, isoleucine, phenylalanine, and tryptophan according to EU index numbering. In some embodiments, the substitution at position F234 is alanine. In some embodiments, the substitution at position F234 is valine. In some embodiments, the substitution at position F234 is leucine. In some embodiments, the substitution at position F234 is isoleucine. In some embodiments, the substitution at position F234 is phenylalanine. In some embodiments, the substitution at position F234 is tryptophan.

In some embodiments, the substitution at position L235 is an acidic amino acid according to EU index numbering. In some embodiments, the substitution at position L235 is an acidic amino acid selected from a group consisting of glutamate and aspartate. In some embodiments, the substitution at position L235 is glutamate. In some embodiments, the substitution at position L235 is aspartate.

In some embodiments, the substitution at position D265 is a non-polar amino acid according to EU index numbering.

In some embodiments, the substitution at position D265 is a non-polar amino acid selected from a group consisting of alanine, cysteine, glycine, isoleucine, leucine, methionine, and valine. In some embodiments, the substitution at position D265 is alanine. In some embodiments, the substitution at position D265 is cysteine. In some embodiments, the substitution at position D265 is glycine. In some embodiments, the substitution at position D265 is isoleucine. In some embodiments, the substitution at position D265 is leucine. In some embodiments, the substitution at position D265 is methionine. In some embodiments, the substitution at position D265 is valine.

In some embodiments, the Fc domain comprises F234V mutation according to EU index numbering. In some embodiments, the Fc domain comprises L235E mutation according to EU index numbering. In some embodiments, the Fc domain comprises D265G mutation according to EU index numbering. In some embodiments, the Fc domain comprises F234V, L235E, and D265G mutations according to EU index numbering. In some embodiments, the Fc domain comprises F234V, L235E, D265G, and S228P mutations according to EU index numbering.

In some embodiments, the Fc domain comprises T307Q, Q331V, A378V, F234V, L235E, D265G, and S228P mutations according to EU index numbering.

In some embodiments, the antibody or a fragment there of inhibits formation of C3 convertase and/or C5 convertase. In some embodiments, the antibody or a fragment thereof does not bind to C3 protein.

In some embodiments, the antibody or a fragment thereof inhibits the activity of C3 convertase. In some embodiments, the antibody or a fragment thereof targets solid phase alternative pathway C3 convertase activity. In some embodiments, the antibody or a fragment thereof targets fluid phase alternative pathway C3 convertase activity. In some embodiments, the antibody or a fragment thereof targets both solid phase and fluid phase alternative pathway C3 convertase activity.

In some embodiments, the Fc domain comprises an amino acid sequence at least 80% identical to SEQ ID NO: 14. In some embodiments, the Fc domain comprises an amino acid sequence at least 85% identical to SEQ ID NO: 14. In some embodiments, the Fc domain comprises an amino acid sequence at least 88% identical to SEQ ID NO: 14. In some embodiments, the Fc domain comprises an amino acid sequence at least 90% identical to SEQ ID NO: 14. In some embodiments, the Fc domain comprises an amino acid sequence at least 92% identical to SEQ ID NO: 14. In some embodiments, the Fc domain comprises an amino acid sequence at least 93% identical to SEQ ID NO: 14. In some embodiments, the Fc domain comprises an amino acid sequence at least 94% identical to SEQ ID NO: 14. In some embodiments, the Fc domain comprises an amino acid sequence at least 95% identical to SEQ ID NO: 14. In some embodiments, the Fc domain comprises an amino acid sequence at least 96% identical to SEQ ID NO: 14. In some embodiments, the Fc domain comprises an amino acid sequence at least 97% identical to SEQ ID NO: 14. In some embodiments, the Fc domain comprises an amino acid sequence at least 98% identical to SEQ ID NO: 14. In some embodiments, the Fc domain comprises an amino acid sequence at least 99% identical to SEQ ID NO: 14. In some embodiments, the Fc domain comprises an amino acid sequence of SEQ ID NO: 14.

In some embodiments, the Fc domain comprises an amino acid sequence at least 80% identical to SEQ ID NO: 10. In some embodiments, the Fc domain comprises an amino acid sequence at least 85% identical to SEQ ID NO: 10. In some embodiments, the Fc domain comprises an amino acid sequence at least 88% identical to SEQ ID NO: 10. In some embodiments, the Fc domain comprises an amino acid sequence at least 90% identical to SEQ ID NO: 10. In some embodiments, the Fc domain comprises an amino acid sequence at least 92% identical to SEQ ID NO: 10. In some embodiments, the Fc domain comprises an amino acid sequence at least 93% identical to SEQ ID NO: 10. In some embodiments, the Fc domain comprises an amino acid sequence at least 94% identical to SEQ ID NO: 10. In some embodiments, the Fc domain comprises an amino acid sequence at least 95% identical to SEQ ID NO: 10. In some embodiments, the Fc domain comprises an amino acid sequence at least 96% identical to SEQ ID NO: 10. In some embodiments, the Fc domain comprises an amino acid sequence at least 97% identical to SEQ ID NO: 10. In some embodiments, the Fc domain comprises an amino acid sequence at least 98% identical to SEQ ID NO: 10. In some embodiments, the Fc domain comprises an amino acid sequence at least 99% identical to SEQ ID NO: 10. In some embodiments, the Fc domain comprises an amino acid sequence of SEQ ID NO: 10.

In some embodiments, the antibody or antigen binding fragment thereof comprises an amino acid sequence at least 80% identical to SEQ ID NO: 4. In some embodiments, the antibody or antigen binding fragment thereof comprises an amino acid sequence at least 85% identical to SEQ ID NO: 4. In some embodiments, the antibody or antigen binding fragment thereof comprises an amino acid sequence at least 88% identical to SEQ ID NO: 4. In some embodiments, the antibody or antigen binding fragment thereof comprises an amino acid sequence at least 90% identical to SEQ ID NO: 4. In some embodiments, the antibody or antigen binding fragment thereof comprises an amino acid sequence at least 92% identical to SEQ ID NO: 4. In some embodiments, the antibody or antigen binding fragment thereof comprises an amino acid sequence at least 95% identical to SEQ ID NO: 4. In some embodiments, the antibody or antigen binding fragment thereof comprises an amino acid sequence at least 96% identical to SEQ ID NO: 4. In some embodiments, the antibody or antigen binding fragment thereof comprises an amino acid sequence at least 97% identical to SEQ ID NO: 4. In some embodiments, the antibody or antigen binding fragment thereof comprises an amino acid sequence at least 98% identical to SEQ ID NO: 4. In some embodiments, the antibody or antigen binding fragment thereof comprises an amino acid sequence at least 99% identical to SEQ ID NO: 4. In some embodiments, the antibody or antigen binding fragment thereof comprises an amino acid sequence of SEQ ID NO: 4.

In some embodiments, the antibody or antigen binding fragment thereof comprises an amino acid sequence at least 80% identical to SEQ ID NO: 5. In some embodiments, the antibody or antigen binding fragment thereof comprises an amino acid sequence at least 85% identical to SEQ ID NO: 5. In some embodiments, the antibody or antigen binding fragment thereof comprises an amino acid sequence at least 88% identical to SEQ ID NO: 5. In some embodiments, the antibody or antigen binding fragment thereof comprises an amino acid sequence at least 90% identical to SEQ ID NO: 5. In some embodiments, the antibody or antigen binding fragment thereof comprises an amino acid sequence at least 92% identical to SEQ ID NO: 5. In some embodiments, the antibody or antigen binding fragment thereof comprises an amino acid sequence at least 95% identical to SEQ ID NO: 5. In some embodiments, the antibody or antigen binding fragment thereof comprises an amino acid sequence at least 96% identical to SEQ ID NO: 5. In some embodiments, the antibody or antigen binding fragment thereof comprises an amino acid sequence at least 97% identical to SEQ ID NO: 5. In some embodiments, the antibody or antigen binding fragment thereof comprises an amino acid sequence at least 98% identical to SEQ ID NO: 5. In some embodiments, the antibody or antigen binding fragment thereof comprises an amino acid sequence at least 99% identical to SEQ ID NO: 5. In some embodiments, the antibody or antigen binding fragment thereof comprises an amino acid sequence of SEQ ID NO: 5.

In some embodiments, the antibody or antigen binding fragment thereof comprises an amino acid sequence at least 80% identical to SEQ ID NO: 6. In some embodiments, the antibody or antigen binding fragment thereof comprises an amino acid sequence at least 85% identical to SEQ ID NO: 6. In some embodiments, the antibody or antigen binding fragment thereof comprises an amino acid sequence at least 88% identical to SEQ ID NO: 6. In some embodiments, the antibody or antigen binding fragment thereof comprises an amino acid sequence at least 90% identical to SEQ ID NO: 6. In some embodiments, the antibody or antigen binding fragment thereof comprises an amino acid sequence at least 92% identical to SEQ ID NO: 6. In some embodiments, the antibody or antigen binding fragment thereof comprises an amino acid sequence at least 95% identical to SEQ ID NO: 6. In some embodiments, the antibody or antigen binding fragment thereof comprises an amino acid sequence at least 96% identical to SEQ ID NO: 6. In some embodiments, the antibody or antigen binding fragment thereof comprises an amino acid sequence at least 97% identical to SEQ ID NO: 6. In some embodiments, the antibody or antigen binding fragment thereof comprises an amino acid sequence at least 98% identical to SEQ ID NO: 6. In some embodiments, the antibody or antigen binding fragment thereof comprises an amino acid sequence at least 99% identical to SEQ ID NO: 6. In some embodiments, the antibody or antigen binding fragment thereof comprises an amino acid sequence of SEQ ID NO: 6.

In some embodiments, the antibody or antigen binding fragment thereof comprises an amino acid sequence at least 80% identical to SEQ ID NO: 7. In some embodiments, the antibody or antigen binding fragment thereof comprises an amino acid sequence at least 85% identical to SEQ ID NO: 7. In some embodiments, the antibody or antigen binding fragment thereof comprises an amino acid sequence at least 88% identical to SEQ ID NO: 7. In some embodiments, the antibody or antigen binding fragment thereof comprises an amino acid sequence at least 90% identical to SEQ ID NO: 7. In some embodiments, the antibody or antigen binding fragment thereof comprises an amino acid sequence at least 92% identical to SEQ ID NO: 7. In some embodiments, the antibody or antigen binding fragment thereof comprises an amino acid sequence at least 95% identical to SEQ ID NO: 7. In some embodiments, the antibody or antigen binding fragment thereof comprises an amino acid sequence at least 96% identical to SEQ ID NO: 7. In some embodiments, the antibody or antigen binding fragment thereof comprises an amino acid sequence at least 97% identical to SEQ ID NO: 7. In some embodiments, the antibody or antigen binding fragment thereof comprises an amino acid sequence at least 98% identical to SEQ ID NO: 7. In some embodiments, the antibody or antigen binding fragment thereof comprises an amino acid sequence at least 99% identical to SEQ ID NO: 7. In some embodiments, the antibody or antigen binding fragment thereof comprises an amino acid sequence of SEQ ID NO: 7.

In some embodiments, the antibody or antigen binding fragment thereof comprises an amino acid sequence at least 80% identical to SEQ ID NO: 8. In some embodiments, the antibody or antigen binding fragment thereof comprises an amino acid sequence at least 85% identical to SEQ ID NO: 8. In some embodiments, the antibody or antigen binding fragment thereof comprises an amino acid sequence at least 88% identical to SEQ ID NO: 8. In some embodiments, the antibody or antigen binding fragment thereof comprises an amino acid sequence at least 90% identical to SEQ ID NO: 8. In some embodiments, the antibody or antigen binding fragment thereof comprises an amino acid sequence at least 92% identical to SEQ ID NO: 8. In some embodiments, the antibody or antigen binding fragment thereof comprises an amino acid sequence at least 95% identical to SEQ ID NO: 8. In some embodiments, the antibody or antigen binding fragment thereof comprises an amino acid sequence at least 96% identical to SEQ ID NO: 8. In some embodiments, the antibody or antigen binding fragment thereof comprises an amino acid sequence at least 97% identical to SEQ ID NO: 8. In some embodiments, the antibody or antigen binding fragment thereof comprises an amino acid sequence at least 98% identical to SEQ ID NO: 8. In some embodiments, the antibody or antigen binding fragment thereof comprises an amino acid sequence at least 99% identical to SEQ ID NO: 8. In some embodiments, the antibody or antigen binding fragment thereof comprises an amino acid sequence of SEQ ID NO: 8.

In some embodiments, the antibody or antigen binding fragment thereof comprises an amino acid sequence at least 80% identical to SEQ ID NO: 9. In some embodiments, the antibody or antigen binding fragment thereof comprises an amino acid sequence at least 85% identical to SEQ ID NO: 9. In some embodiments, the antibody or antigen binding fragment thereof comprises an amino acid sequence at least 88% identical to SEQ ID NO: 9. In some embodiments, the antibody or antigen binding fragment thereof comprises an amino acid sequence at least 90% identical to SEQ ID NO: 9. In some embodiments, the antibody or antigen binding fragment thereof comprises an amino acid sequence at least 92% identical to SEQ ID NO: 9. In some embodiments, the antibody or antigen binding fragment thereof comprises an amino acid sequence at least 95% identical to SEQ ID NO: 9. In some embodiments, the antibody or antigen binding fragment thereof comprises an amino acid sequence at least 96% identical to SEQ ID NO: 9. In some embodiments, the antibody or antigen binding fragment thereof comprises an amino acid sequence at least 97% identical to SEQ ID NO: 9. In some embodiments, the antibody or antigen binding fragment thereof comprises an amino acid sequence at least 98% identical to SEQ ID NO: 9. In some embodiments, the antibody or antigen binding fragment thereof comprises an amino acid sequence at least 99% identical to SEQ ID NO: 9. In some embodiments, the antibody or antigen binding fragment thereof comprises an amino acid sequence of SEQ ID NO: 9.

In one aspect, the present invention provides, among other things, a nucleic acid encoding an antibody or antigen binding thereof of the present invention. In some embodiments, the nucleic acid is DNA. In some embodiments, the nucleic acid is cDNA. In some embodiments, the nucleic acid is RNA. In some embodiments, the nucleic acid is messenger RNA (mRNA).

In one aspect, the present invention provides, among other things, a messenger RNA encoding an antibody or antigen binding thereof of the present invention.

In one aspect, the present invention provides, among other things, a composition comprising a nucleic acid encoding an antibody or antigen binding thereof of the present invention and a delivery vehicle.

In some embodiments, the delivery vehicle is an adeno-associated virus (AAV) vector. In some embodiments, the delivery vehicle is a lipid nanoparticle (LNP).

In one aspect, the present invention provides, among other things, a composition comprising a lipid nanoparticle (LNP) encapsulating a messenger RNA encoding an anti-C3b antibody or a fragment thereof.

In one aspect, the present invention provides, among other things, a method of treating a complement mediated disease or disorder, said method comprising administering a therapeutically effective amount of the antibody or antibody or antigen binding fragment thereof of the present invention to a subject in need thereof.

In one aspect, the present invention provides, among other things, a method of treating a complement mediated disease or disorder, said method comprising administering a therapeutically effective amount of the mRNA encoding an anti-C3b antibody or antibody or antigen binding fragment thereof of the present invention to a subject in need thereof.

In one aspect, the present invention provides, among other things, a method of treating a complement mediated disease or disorder, said method comprising administering a therapeutically effective amount of an anti-C3b-antibody or a fragment thereof to a subject in need thereof.

In some embodiments, the complement mediated disease or disorder is C glomerulopathy or a disease or disorder associated with C3 glomerulopathy. In some embodiments, the disease or disorder associated with C3 glomerulopathy is dense deposit disease (DDD). In some embodiments, the disease or disorder associated with C3 glomerulopathy is C3 glomerulonephritis (C3GN). In some embodiments, the complement mediated disease or disorder is characterized by accumulation of the C3 component of complement in renal tissue. In some embodiments, the subject has symptomatic hematuria, proteinuria, acute kidney injury (AKI), or chronic kidney disease (CKD). In some embodiments, the complement mediated disease or disorder is paroxysmal nocturnal hemoglobinuria, geographic atrophy, or autoimmune hemolytic anemia (AIHA). In some embodiments, the complement mediated disease or disorder is age-related macular degeneration (AMD). In some embodiments, the complement mediated disease or disorder is wet age-related macular degeneration (wAMD). In some embodiments, the complement mediated disease or disorder is Passive Heymann Nephritis (PHN).

BRIEF DESCRIPTION OF THE DRAWINGS

The drawings are for illustration purposes only, not for limitation.

FIG. 1A shows the levels of Ab1 and control Ab in plasma levels over 20 days. FIG. 1B shows the percentage of remaining antibodies for Ab1 and control Ab in plasma levels over 20 days.

FIG. 3A is an exemplary graph showing FA leakage area at Day 7 after treatment with test antibodies and controls. FIG. 3B is an exemplary graph showing the OCT area at Day 7 after treatment with test antibodies and controls.

DEFINITIONS

Figure 1A:
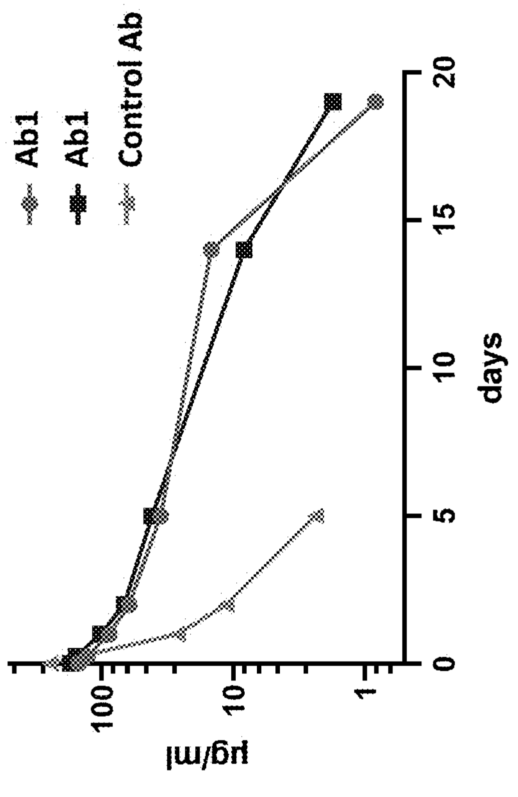
FIGS. 1A and 1B are exemplary graphs showing the pharmacokinetic effect of Ab1 (duplicates) and control Ab in Cynomolgus monkeys.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Antibody: As used herein, the term "antibody" refers to immunoglobulin molecules and immunologically active portions of immunoglobulin (Ig) molecules, i.e., molecules that contain an antigen binding site that binds (immunoreacts with) an antigen. By "binds" or "immunoreacts with" is meant that the antibody reacts with one or more antigenic determinants of the desired. Antibodies include, antibody fragments. Antibodies also include, but are not limited to, polyclonal, monoclonal, chimeric dAb (domain antibody), single chain, a single domain antibody (VHH), an antigen binding site fused to a constant region (Fc), Fab, Fab', F(ab')2 fragments, scFvs, and Fab expression libraries. An antibody may be a whole antibody, or immunoglobulin, or an antibody fragment.

Amino acid: As used herein, term "amino acid," in its broadest sense, refers to any compound and/or substance that can be incorporated into a polypeptide chain. In some embodiments, an amino acid has the general structure $H_2N—C(H)(R)—COOH$. In some embodiments, an amino acid is a naturally occurring amino acid. In some embodiments, an amino acid is a synthetic amino acid; in some embodiments, an amino acid is a d-amino acid; in some embodiments, an amino acid is an 1-amino acid. "Standard amino acid" refers to any of the twenty standard 1-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxyl- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Amelioration: As used herein, the term "amelioration" is meant the prevention, reduction or palliation of a state, or improvement of the state of a subject. Amelioration includes, but does not require complete recovery or complete prevention of a disease condition. In some embodiments, Amelioration can refer to partial recovery or prevention of a disease condition. In some embodiments, amelioration includes increasing levels of relevant protein or its activity that is deficient in relevant disease tissues.

Approximately or about: As used herein, the term "approximately" or "about," as applied to one or more values of interest, refers to a value that is similar to a stated reference value.

Delivery: As used herein, the term "delivery" encompasses both local and systemic delivery.

Improve, increase, inhibit or reduce: As used herein, the terms "improve," "increase" "inhibit" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein, e.g., a subject who is administered a placebo. A "control subject" is a subject afflicted with the same form of disease as the subject being treated, who is about the same age as the subject being treated.

Inhibition or inhibiting: As used herein "inhibition" or "inhibiting," or grammatical equivalents, means reduction, decrease or inhibition of biological activity. Neutralization: As used herein, neutralization means reduction or inhibition of biological activity of the protein to which the neutralizing antibody binds, in this case anti-C3b antibody, e.g. reduction or inhibition of any one of complement system component signaling e.g. as measured by C3b-mediated responses. The reduction or inhibition in biological activity may be partial or total. The degree to which an antibody neutralizes C3b is referred to as its neutralizing potency.

Patient: As used herein, the term "patient" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLAS TN for nucleotide sequences and BLASTP, gapped BLAST, and PSI-BLAST for amino acid sequences. Exemplary such programs are described in Altschul, et al., Basic local alignment search tool, *J Mal. Biol.,* 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. In some embodiments, the "therapeutically effective amount" is sufficient to prevent progression of a disease condition, an onset of one or more symptoms or complications associated with the condition, or a significant increase or a significant decrease in the level of one or more biomarkers associated with the condition from its normal level. For example, the "therapeutically effective amount" is sufficient to prevent progression of symptoms or complications associated with complement system. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease. In some embodiments, the term "treating" or its grammatically equivalents refers to preventing a disease condition, an onset of one or more symptoms associated with the condition, or a significant increase or a significant decrease in the level of one or more biomarkers associated with the condition from its normal level. For example, treating a patient with complement mediated disorders (e.g., C3 glomerulopathy) includes prevention of progression of symptoms or complications associated with complement mediated disorders, such as, prevention of C3 deposition.

DETAILED DESCRIPTION

The present invention provides, among other things, anti-C3b antibodies. Antibodies also include, but are not limited to, polyclonal, monoclonal, chimeric dAb (domain antibody), single chain, a single domain antibody (VHH), single-domain antibody-Fc fusion (VHH-Fc), an antigen binding site fused to a constant region (Fc), Fab, Fab', F(ab')2 fragments, scFvs, and Fab expression libraries. The new class of anti-C3b antibodies, e.g., single-domain antibody (VHH), single-domain antibody-Fc fusion (VHH-Fc), an antigen binding site fused to a constant region (Fc), of the present invention can effectively interfere with the formation of the alternative pathway's C3 convertase (C3bBP) and thereby prevent the cascade from proceeding downstream to the amplification loop of the complement cascade.

In some embodiments, the C3b-antibodies of the present invention selectively binds to C3b and inhibits the C3 convertase formation and mediates clearance of C3 deposits. The present invention also provides methods for treating complement mediated diseases and disorders with anti-C3b antibodies further described herein. Anti-C3b antibodies of the present invention are characterized by having high binding affinity to human C3b (e.g., with C3b $K_D$ less than 50 nM) and minimal cross-reactivity with C3 (e.g., with greater than 10 fold selectivity for C3b over C3). Selectively binding to C3b via, e.g., neoepitope on C3b, and can effectively target C3 convertase in diseased tissues without being saturated by high levels of circulating C3. As a result of the present invention's selective binding, the present invention can be used at a lower dose to achieve therapeutic effect relative to the other anti-C3b antibodies or anti-C3 antibodies.

In some embodiments, the antibody or the antibody fragment thereof is a single domain antibody (VHH). The VHH selectively binds to C3b and inhibits the C3 convertase formation and mediates clearance of C3 deposit. With high binding affinity and minimal cross-reactivity with C3b, the VHH-Fc fusion inhibits the formation of C3 convertase and mediating clearance of c3 deposits. The present invention provides inventive anti-C3b antibodies that (i) inhibit the C3 convertase formation and mediate clearance of C3 deposits; (ii) block C3b interaction with factor B (fB); (iii) inhibit activity specific to the alternative pathway (AP); (iv) limit the interference of natural regulators of C3 convertase such as factor H (fH), DAF and other inhibitors; and/or (v) inhibit stabilization of C3 convertase by C3bNef autoantibodies.

In some embodiments, the antibody or the antibody fragment thereof is a VHH-Fc fusion. The VHH-Fc fusion selectively binds to C3b and inhibits the C3 convertase formation and mediates clearance of C3 deposit. With high binding affinity and minimal cross-reactivity with C3b, the VHH-Fc fusion inhibits the formation of C3 convertase and mediating clearance of c3 deposits. The present invention provides inventive anti-C3b antibodies that (i) inhibit the C3 convertase formation and mediate clearance of C3 deposits; (ii) block C3b interaction with factor B (fB); (iii) inhibit activity specific to the alternative pathway (AP); (iv) limit the interference of natural regulators of C3 convertase such as factor H (fH), DAF and other inhibitors; and/or (v) inhibit stabilization of C3 convertase by C3bNef autoantibodies.

In some embodiments, the antibodies of the present invention perform one or more of the following functions: (i) inhibit the C3 convertase formation and mediate clearance of C3 deposits; (ii) target both solid phase and fluid phase alternative pathway C3 convertase activity; (iii) block C3b interaction with factor B (fB); (iv) inhibit activity specific to the alternative pathway (AP); (v) limit the interference of natural regulators of C3 convertase such as factor H (fH), DAF and other inhibitors; (vi) have favorable biophysical and pharmacokinetic properties to allow for prolonged therapeutic effect (biweekly or monthly dosing); and/or (vii) inhibit stabilization of C3 convertase by C3bNef autoantibodies. The present invention also provides a panel of antibodies that specifically and selectively binds human C3b and inhibit C3 convertase activity. This panel includes antibodies differing in their epitope, affinity and selectivity for C3b over C3.

Various aspects of the invention are described in detail in the following sections. The use of sections is not meant to limit the invention. Each section can apply to any aspect of the invention. In this application, the use of "or" means "and/or" unless stated otherwise.

Complement System

The complement system is a part of the innate immune system which does not adapt to changes over the course of the host's life, but is recruited and used by the adaptive immune system. For example, it assists, or complements, the ability of antibodies and phagocytic cells to clear pathogens. This sophisticated regulatory pathway allows rapid reaction to pathogenic organisms while protecting host cells from destruction. Over thirty proteins and protein fragments make up the complement system. These proteins act through opsonization (enhancing phagocytosis of antigens), chemotaxis (attracting macrophages and neutrophils), cell lysis (rupturing membranes of foreign cells) and agglutination (clustering and binding of pathogens together). The complement system has three pathways: classical, alternative and lectin. Classical pathway (CP) is activated by certain isotypes of antibodies bound to antigens. Alternative pathway (AP) is activated on microbial cell surfaces in the absence of antibody. Lectin pathway is activated by a plasma lectin that binds to mannose residues on microbes. Although the pathways of complement activation differ in how they are initiated, all of them result in the generation of enzyme complexes that are able to cleave the most abundant complement protein, C3.

Classical Pathway (CP)

The classical pathway, so called because it was discovered first, uses a plasma protein called C1q to detect antibodies bound to the surface of a microbe or other structure. Once C1q binds to the Fc portion of the antibodies, two associated serine proteases, called C1r and C1s, become active and initiate a proteolytic cascade involving other complement proteins. The classical pathway is one of the major effector mechanisms of the humoral arm of adaptive immune responses. Innate immune system soluble proteins called pentraxins, can also bind C1q and initiate the classical pathway.

Lectin Pathway

Lectin pathway is triggered by a plasma protein called mannose-binding lectin (MBL), which recognizes terminal mannose residues on microbial glycoproteins and glycolipids, similar to the mannose receptor on phagocyte membranes described earlier. MBL is a member of the collection family with a hexameric structure similar to the C1q component of the complement system. After MBL binds to microbes, two zymogens called MASP1 (mannose-associated serine protease 1, or mannan-binding lectin-associated serine protease) and MASP2, with similar functions to C1r and C1s, associate with MBL and initiate downstream proteolytic steps identical to the classical pathway. The central event in complement activation is proteolysis of the complement protein C3 to generate biologically active products and the subsequent covalent attachment of a product of C3, called C3b, to microbial cell surfaces or to antibody bound to antigen. Complement activation depends on the generation of two proteolytic complexes: the C3 convertase, which cleaves C3 into two proteolytic fragments called C3a and C3b; and the C5 convertase, which cleaves C5 into C5a and C5b.

Alternative Pathway (AP)

The third pathway of complement activation is called the alternative pathway because it was discovered as a second, or 'alternative,' pathway for complement activation after the classical pathway had been defined. This pathway can proceed on many microbial surfaces in the absence of specific antibody, and it leads to the generation of a distinct C3 convertase designated C3bBb. In contrast to the classical and MB-lectin pathways of complement activation, the alternative pathway does not depend on a pathogen-binding protein for its initiation; instead it is initiated through the spontaneous hydrolysis of C3. A number of mechanisms ensure that the activation pathway will only proceed on the surface of a pathogen.

C3 Convertase and C3b

C3 is abundant in plasma, and C3b is produced at a significant rate by spontaneous cleavage (also known as 'tickover'). This occurs through the spontaneous hydrolysis of the thioester bond in C3 to form C3(H2O) which has an altered conformation, allowing binding of the plasma protein factor B. The binding of B by C3(H2O) then allows a plasma protease called factor D to cleave factor B to Ba and Bb, the latter remaining associated with C3(H2O) to form the C3(H2O)Bb complex. This complex is a fluid-phase C3 convertase, and although it is only formed in small amounts it can cleave many molecules of C3 to C3a and C3b. Much of this C3b is inactivated by hydrolysis, but some attaches covalently, through its reactive thioester group, to the surfaces of host cells or to pathogens. C3b bound in this way is able to bind factor B, allowing its cleavage by factor D to yield the small fragment Ba and the active protease Bb. This results in formation of the alternative pathway C3 convertase, C3b, Bb.

When C3b binds to host cells, a number of complement-regulatory proteins, present in the plasma and on host cell membranes combine to prevent complement activation from proceeding. These proteins interact with C3b and either prevent the convertase from forming, or promote its rapid dissociation. Thus, the complement receptor 1 (CR1) and a membrane-attached protein known as decay-accelerating factor (DAF or CD55) compete with factor B for binding to C3b on the cell surface, and can displace Bb from a convertase that has already formed. Convertase formation can also be prevented by cleaving C3b to its inactive derivative iC3b. This is achieved by a plasma protease, factor I, in conjunction with C3b-binding proteins that can act as cofactors, such as CR1 and membrane cofactor of proteolysis (MCP or CD46), another host cell membrane protein. Factor H is another complement-regulatory protein in plasma that binds C3b and, like CR1, it is able to compete with factor B and displace Bb from the convertase in addition to acting as a cofactor for factor I. Factor H binds preferentially to C3b bound to vertebrate cells as it has an affinity for the sialic acid residues present on these cells.

By contrast, because pathogen surfaces lack these regulatory proteins and sialic acid residues, the C3bBb convertase can form and persist. Indeed, this process may be favored by a positive regulatory factor, known as properdin or factor P, which binds to many microbial surfaces and stabilizes the convertase. Deficiencies in factor P are associated with a heightened susceptibility to infection with *Neisseria* species. Once formed, the C3b, Bb convertase rapidly cleaves yet more C3 to C3b, which can bind to the pathogen and either act as an opsonin or reinitiate the pathway to form another molecule of C3bBb convertase. Thus, the alternative pathway activates through an amplification loop that can proceed on the surface of a pathogen, but not on a host cell. This same amplification loop enables the alternative pathway to contribute to complement activation initially triggered through the classical or MB-lectin pathways.

The C3 convertases resulting from activation of the classical and MB-lectin pathways (C4b, 2b) and from the alternative pathway (C3b,Bb) are apparently distinct. Only one component of the alternative pathway appears entirely unrelated to its functional equivalents in the classical and MB-lectin pathways; this is the initiating serine protease, factor D. Factor D can also be singled out as the only activating protease of the complement system to circulate as an active enzyme rather than a zymogen. This is both necessary for the initiation of the alternative pathway through spontaneous C3 cleavage, and safe for the host because factor D has no other substrate than factor B when bound to C3b. This means that factor D only finds its substrate at a very low level in plasma, and at pathogen surfaces where the alternative pathway of complement activation is allowed to proceed.

The formation of C3 convertases is the point at which the three pathways of complement activation converge, because both the classical pathway and MB-lectin pathway convertases C4b,2b, and the alternative pathway convertase C3bBb have the same activity, and they initiate the same subsequent events. They both cleave C3 to C3b and C3a. C3b binds covalently through its thioester bond to adjacent molecules on the pathogen surface; otherwise it is inactivated by hydrolysis. C3 is the most abundant complement protein in plasma, occurring at a concentration of 1.2 mg ml-1, and up to 1000 molecules of C3b can bind in the vicinity of a single active C3 convertase. Thus, the main effect of complement activation is to deposit large quantities of C3b on the surface of the infecting pathogen, where it forms a covalently bonded coat that can signal the ultimate destruction of the pathogen by phagocytes.

The next step in the cascade is the generation of the C5 convertases. In the classical and the MB-lectin pathways, a C5 convertase is formed by the binding of C3b to C4b,2b to yield C4b,2b,3b. By the same token, the C5 convertase of the alternative pathway is formed by the binding of C3b to the C3 convertase to form C3b2Bb. C5 is captured by these C5 convertase complexes through binding to an acceptor site on C3b, and is then rendered susceptible to cleavage by the serine protease activity of C2b or Bb. This reaction, which generates C5b and C5a, is much more limited than cleavage of C3, as C5 can be cleaved only when it binds to C3b that is part of the C5 convertase complex. Thus, complement activation by both the alternative, MB-lectin and classical pathways leads to the binding of large numbers of C3b molecules on the surface of the pathogen, the generation of a more limited number of C5b molecules, and the release of C3a and C5a.

C3b Antagonists and Anti-C3b Antibodies

A C3b antagonist suitable for the present invention includes those therapeutic agents that can reduce, inhibit or abolish one or more C3b mediated signaling including those described herein. For example, a suitable C3b antagonist according to the invention includes, but is not limited to an anti-C3b antibody or a fragment thereof, anti-C3b VHH-Fc, a soluble C3b binding protein, a soluble C3b binding protein-Fc fusion protein or a fragment thereof, to name but a few.

Anti-C3b Antibodies and Fragments

A traditional antibody, also known as an immunoglobulin, is a Y-shaped structure which consists of four polypeptides—two heavy chains and two light chains. This structure allows antibody molecules to carry out their dual functions: antigen binding and biological activity mediation. Each function is carried out by different parts of the antibody: fragment antigen-binding (Fab fragment) and fragment crystallizable region (Fc region). Fab fragment is a region on an antibody that binds to antigens. It is composed of one constant and one variable domain of each of the heavy and the light chain. These domains shape the paratope—the antigen-binding site—at the amino terminal end of the monomer. Fc region is the tail region of an antibody that interacts with cell surface receptors called Fc receptors and some proteins of the complement system. This property allows antibodies to activate the immune system. The Fc regions of immunoglobulin Gs bear a highly conserved N-glycosylation site.

Within the VH and VL regions exists three CDRs, hypervariable amino acid sequences, forming the antigen-binding sites of each Fab. The interface of each heavy and light chain CDRs with the constant segments creates a three-dimensional binding structure with high specificity for a distinct antigenic determinant or epitope.

Single Domain Antibody (VHH)

A single domain antibody (VHH) is a fragment represents the smallest antigen binding domains of antibodies. Despite having a molecular weight typically less than its parent antibody of 12-15 KDa, this type of antibody retains its binding specificity and affinity. This type of single-domain antibody is characterized by its high physical and thermal stability and production process.

In some embodiments, a VHH is fused to an Fc domain. In some embodiments, a VHH is fused to a CH2 domain. In some embodiments, a VHH is fused to a CH3 domain. In some embodiments, a VHH is fused to a CH2 and a CH3 domain.

Constant Region (Fc)

The Fc region of an antibody interacts with a number of Fc receptors and ligands, imparting an array of important functional capabilities referred to as effector functions. For IgG, the Fc region comprises Ig domains Cγ2 and Cγ3 and the N-terminal hinge leading into Cγ2. An important family of Fc receptors for the IgG class are the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65, incorporated by reference). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and γδ T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290, incorporated by reference). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP). A number of structures have been solved of the extracellular domains of human FcγRs, including FcγRIIa (pdb accession code 1H9V) (Sondermann et al., 2001, J Mol Biol 309:737-749) (pdb accession code 1 FCG) (Maxwell et al., 1999, Nat Struct Biol 6:437-442), FcγRIIb (pdb accession code 2FCB) (Sondermann et al., 1999, Embo J 18:1095-1103); and FcγRIIIb (pdb accession code 1E4J) (Sondermann et al., 2000, Nature 406:267-273, incorporated by reference). All FcγRs bind the same region on Fc, at the N-terminal end of the Cγ2 domain and the preceding hinge. This interaction is well characterized structurally (Sondermann et al., 2001, J Mol Biol 309:737-749 incorporated by reference), and several structures of the human Fc bound to the extracellular domain of human FcγRIIIb have been solved (pdb accession code 1E4K)(Sondermann et al., 2000, Nature 406:267-273) (pdb accession codes 1IIS and 1IIX) (Radaev et al., 2001, J Biol Chem 276:16469-16477, incorporated by reference), as well as has the structure of the human IgE Fd/FcεRIa complex (pdb accession code 1F6A) (Garman et al., 2000, Nature 406:259-266, incorporated by reference).

An overlapping but separate site on Fc serves as the interface for the complement protein C1q. In the same way that Fc/FcγR binding mediates ADCC, Fc/C1q binding mediates complement dependent cytotoxicity (CDC). C1q forms a complex with the serine proteases C1r and C1s to form the C1 complex. C1q is capable of binding six antibodies, although binding to two IgGs is sufficient to activate the complement cascade. Similar to Fc interaction with FcγRs, different IgG subclasses have different affinity for C1q, with IgG1 and IgG3 typically binding substantially better to the FcγRs than IgG2 and IgG4.

A site on Fc between the Cγ2 and Cγ3 domains mediates interaction with the neonatal receptor FcRn, the binding of which recycles endocytosed antibody from the endosome back to the bloodstream (Raghavan et al., 1996, Annu Rev Cell Dev Biol 12:181-220; Ghetie et al., 2000, Annu Rev Immunol 18:739-766, incorporated by reference). This process, coupled with preclusion of kidney filtration due to the large size of the full length molecule, results in favorable antibody serum half-lives ranging from one to three weeks. Binding of Fc to FcRn also plays a key role in antibody transport. The binding site for FcRn on Fc is also the site at which the bacterial proteins A and G bind. The tight binding by these proteins is typically exploited as a means to purify antibodies by employing protein A or protein G affinity chromatography during protein purification. Thus the fidelity of this region on Fc is important for both the clinical properties of antibodies and their purification. Available structures of the rat Fc/FcRn complex (Martin et al., 2001, Mol Cell 7:867-877, incorporated by reference), and of the complexes of Fc with proteins A and G (Deisenhofer, 1981, Biochemistry 20:2361-2370; Sauer-Eriksson et al., 1995, Structure 3:265-278; Tashiro et al., 1995, Curr Opin Struct Biol 5:471-481, incorporated by reference) provide insight into the interaction of Fc with these proteins.

In some embodiments, an antibody or fragments thereof comprises an optimized Fc variants useful in a variety of contexts. As outlined above, current antibody therapies suffer from a variety of problems. The present invention provides a promising means for enhancing the therapeutic efficacy of antibodies is via abolishment of their ability to mediate cytotoxic effector functions such as ADCC, ADCP, and CDC.

Fc Variants

An Fc polypeptide that comprises an Fc variant described herein is referred to as an "Fe polypeptide". Fc polypeptides of the present invention include polypeptides that comprise the Fc variants in the context of a larger polypeptide, such as an antibody or Fc fusion. That is, Fc polypeptides include antibodies and Fc fusions that comprise Fc variants of the present invention. Fc polypeptides of the present invention also include polypeptides that comprise little or no additional polypeptide sequence other than the Fc region, referred to as an isolated Fc. Fc polypeptides described in the present invention also include fragments of the Fc region. As described below, any of the aforementioned Fc polypeptides may be fused to one or more fusion partners or conjugate partners to provide desired functional properties.

The parent Fc polypeptides described herein may be derived from a wide range of sources, and may be substantially encoded by one or more Fc genes from any organism, including but not limited to humans, rodents including but not limited to mice and rats, lagomorpha such as rabbits and hares, camelidae such as camels, llamas, and dromedaries, and non-human primates, including but not limited to Prosimians, Platyrrhini (New World monkeys), Cercopithecoidea (Old World monkeys), and Hominoidea include the Gibbons, Lesser and Great Apes, with humans most preferred. The parent Fc polypeptides of the present invention may be substantially encoded by immunoglobulin genes belonging to any of the antibody classes, including but not limited to sequences belonging to the IgG (including human subclasses IgG1, IgG2, IgG3, or IgG4), IgA (including human subclasses IgA1 and IgA2), IgD, IgE, IgG, or IgM classes of antibodies. The parent Fc polypeptides of the present invention comprise sequences belonging to the human IgG class of antibodies. For example, the parent Fc polypeptide may be a parent antibody, for example a human IgG1 antibody, a human IgA antibody, or a mouse IgG2a or IgG2b antibody. Said parent antibody may be nonhuman, chimeric, humanized, or fully human as described in detail below. The parent Fc polypeptide may be modified or engineered in some way, for example a parent antibody may be affinity matured, or may possess engineered glycoforms, all as described more fully below. Alternatively, the parent Fc polypeptide may be an Fc fusion, for example an Fc fusion wherein the fusion partner targets a cell surface receptor. Alternatively, the parent Fc polypeptide may be an isolated Fc region, comprising little or no other polypeptide sequence outside the Fc region. The parent Fc polypeptide may be a naturally existing Fc region, or may be an existing engineered variant of an Fc polypeptide. What is important is that the parent Fc polypeptide comprise an Fc region, which can then be mutated to generate an Fc variant.

Optimized Properties

Fc variants described herein are optimized for a number of therapeutically relevant properties. An Fc variant comprises one or more amino acid modifications relative to a parent Fc polypeptide, wherein said amino acid modification(s) provide one or more optimized properties. An Fc variant of the present invention differs in amino acid sequence from its parent Fc polypeptide by virtue of at least one amino acid modification. In some embodiments, Fc variants have at least one amino acid modification compared to the parent. Alternatively, in some embodiments the Fc variants may have more than one amino acid modification as compared to the parent, for example from about one to fifty amino acid modifications, from about one to ten amino acid modifications, or from about one to about five amino acid modifications compared to the parent. Thus the sequences of the Fc variants and those of the parent Fc polypeptide are substantially homologous. For example, the variant Fc variant sequences herein will possess about 80% homology with the parent Fc variant sequence, preferably at least about 90% homology, and most preferably at least about 95% homology.

The Fc variants may be optimized for a variety of properties. An Fc variant that is engineered or predicted to display one or more optimized properties is herein referred to as an "optimized Fc variant". Properties that may be optimized include but are not limited to enhanced or reduced affinity for an FcγR. In some embodiments, the Fc variants are optimized to have reduced or ablated affinity for a human FcγR, including but not limited to FcγRI, FcγRIIa, FcγRIIb, FcγRIIc, FcγRIIIa, and FcγRIIIb. These embodiments are anticipated to provide Fc polypeptides with enhanced therapeutic properties in humans, for example reduced effector function and reduced toxicity. In other embodiments, Fc variants provide enhanced affinity for one or more FcγRs, yet reduced affinity for one or more other FcγRs. For example, an Fc variant may have enhanced binding to FcγRIIIa, yet reduced binding to FcγRIIb. Alternately, an Fc variant may have enhanced binding to FcγRIIa and FcγRI, yet reduced binding to FcγRIIb. In yet another embodiment, an Fc variant may have enhanced affinity for FcγRIIb, yet reduced affinity to one or more activating FcγRs.

In some embodiments, an Fc variant has reduced or ablated affinity for FcγRI. In some embodiments, an Fc variant has reduced or ablated affinity for FcγRIIa. In some embodiments, an Fc variant has reduced or ablated affinity for FcγRIIb. In some embodiments, an Fc variant has reduced or ablated affinity for FcγRIIc. In some embodiments, an Fc variant has reduced or ablated affinity for FcγRIIIa. In some embodiments, an Fc variant has reduced or ablated affinity for FcγRIIIb. In some embodiments, an Fc variant has reduced or ablated affinity for C1q. In some embodiments, an Fc variant has enhanced affinity for FcRn. In some embodiments, an Fc variant maintains affinity for FcRn. In some embodiments, an Fc variant has reduced or ablated affinity for FcγRI, FcγRIIa, FcγRIIb, FcγRIIIa, FcγRIIIb, and C1q. In some embodiments, an Fc variant has reduced or ablated affinity for FcγRI, FcγRIIa, FcγRIIb, FcγRIIIa, FcγRIIIb, and C1q, and retains binding to FcRn.

The Fc variants may also be optimized for enhanced functionality and/or solution properties in aglycosylated form. In a preferred embodiment, the aglycosylated Fc variants bind an Fc ligand with reduced affinity than the aglycosylated form of the parent Fc variant. Said Fc ligands include but are not limited to FcγRs, C1q, FcRn, and proteins A and G, and may be from any source including but not limited to human, mouse, rat, rabbit, or monkey, preferably human. In an alternately preferred embodiment, the Fc variants are optimized to be more stable and/or more soluble than the aglycosylated form of the parent Fc variant.

In some embodiments, an antibody or a fragment hereof comprises an Fc variant comprising a L235E mutation. In some embodiments, an antibody or a fragment hereof comprises an Fc variant comprising a D265G mutation. In some embodiments, an antibody or a fragment hereof comprises an Fc variant comprising a F234V mutation. In some embodiments, an antibody or a fragment hereof comprises an Fc variant comprising F234V, L235E, D265G mutations.

Engineered Fc Mutations

In some embodiments, an antibody or a fragment thereof comprises an Fc variant of a wild-type human IgG1 Fc region, said Fc variant comprising amino acid substitutions L234F/L235E/D265G, wherein the residues are numbered according to the EU index.

In some embodiments, an antibody or a fragment thereof comprises an Fc variant of a wild-type human IgG1 Fc region, said Fc variant comprising amino acid substitutions T307Q/Q311V/A378V, wherein the residues are numbered according to the EU index.

In some embodiments, an antibody or a fragment thereof comprises an Fc variant of a wild-type human IgG1 Fc region, said Fc variant comprising amino acid substitutions L234F/L235E/D265G/S228P/T307Q/Q311V/A378V, wherein the residues are numbered according to the EU index.

In some embodiments, an antibody or a fragment thereof comprises an Fc variant of a wild-type human IgG1 Fc region, said Fc variant comprising amino acid substitutions L234F/L235E/G237A/D265G, wherein the residues are numbered according to the EU index.

In some embodiments, an antibody or a fragment thereof comprises an Fc variant of a wild-type human IgG1 Fc region, said Fc variant comprising amino acid substitutions L234V/L235E/G237A/D265G, wherein the residues are numbered according to the EU index.

In some embodiments, an antibody or a fragment thereof comprises an Fc variant of a wild-type human IgG1 Fc region, said Fc variant comprising amino acid substitutions L234F/L235E/D265G/A330S/P331S, wherein the residues are numbered according to the EU index.

In some embodiments, an antibody or a fragment thereof comprises an Fc variant of a wild-type human IgG1 Fc region, said Fc variant comprising amino acid substitutions L234V/L235A/G237A/D265G, wherein the residues are numbered according to the EU index.

In some embodiments, an antibody or a fragment thereof comprises an Fc variant of a wild-type human IgG1 Fc region, said Fc variant comprising amino acid substitutions L234V/L235A/G237A/D265G/A330S/P331S wherein the residues are numbered according to the EU index.

In some embodiments, an antibody or a fragment thereof comprises an Fc variant of a wild-type human IgG1 Fc region, said Fc variant comprising an amino acid substitution D265G, wherein the residues are numbered according to the EU index.

In some embodiments, an antibody or a fragment thereof comprises an Fc variant of a wild-type human IgG4 Fc region, said Fc variant comprising amino acid substitutions L235E/D265G/S228P wherein the residues are numbered according to the EU index.

In some embodiments, an antibody or a fragment thereof comprises an Fc variant of a wild-type human IgG4 Fc region, said Fc variant comprising amino acid substitutions F234V/L235E/D265G/S228P wherein the residues are numbered according to the EU index.

In some embodiments, an antibody or a fragment thereof comprises an Fc variant of a wild-type human IgG4 Fc region, said Fc variant comprising amino acid substitutions F234V/L235A/G237A/D265G/S228P wherein the residues are numbered according to the EU index.

In some embodiments, an antibody or a fragment thereof comprises an Fc variant of a wild-type human IgG4 Fc region, said Fc variant comprising amino acid substitutions L235E/G237A/D265G/S228P wherein the residues are numbered according to the EU index.

In some embodiments, an antibody or a fragment thereof comprises an Fc variant of a wild-type human IgG4 Fc region, said Fc variant comprising amino acid substitutions L235E/G237A/P329G/S228P wherein the residues are numbered according to the EU index.

In some embodiments, an antibody or a fragment thereof comprises an Fc variant of a wild-type human IgG4 Fc region, said Fc variant comprising amino acid substitutions L235E/G237A/L328R/S228P wherein the residues are numbered according to the EU index.

In some embodiments, an antibody or a fragment thereof comprises an Fc variant of a wild-type human IgG2 Fc region, said Fc variant comprising amino acid substitutions D265G/A330S/P331S wherein the residues are numbered according to the EU index.

In some embodiments, an antibody or a fragment thereof comprises an Fc variant of a wild-type human IgG2 Fc region, said Fc variant comprising amino acid substitutions A235E/D265G/A330S/P331S wherein the residues are numbered according to the EU index.

In some embodiments, an antibody or a fragment thereof comprises an Fc variant of a wild-type human IgG2 Fc region, said Fc variant comprising amino acid substitutions A235E/D265G/P329G wherein the residues are numbered according to the EU index.

In some embodiments, an antibody or a fragment thereof comprises an Fc variant of a wild-type human IgG Fc region, said Fc variant comprising an amino acid substitutions at positions 235 and 265, wherein the amino acid at 265 is substituted to Gly, wherein the residues are numbered according to the EU index.

In some embodiments, an Fc variant further comprises one or more amino acid substitutions at 234, 237, 329, 330, or 331. In some embodiments, an Fc variant further comprises an amino acid substitution at 234. In some embodiments, an Fc variant further comprises amino acid substitutions at 234 and 237. In some embodiments, an Fc variant further comprises amino acid substitutions at 234, 330, and 331. In some embodiments, an Fc variant further comprises amino acid substitutions at 234, 237, 330, and 331. In some embodiments, an Fc variant further comprises an amino acid substitution at 237. In some embodiments, an Fc variant further comprises amino acid substitutions at 330 and 331. In some embodiments, an Fc variant further comprises an amino acid substitution at 329.

In some embodiments, an antibody or a fragment thereof comprises an Fc variant of a wild-type human IgG Fc region, said Fc variant comprising an amino acid substitutions at positions 234 and 265, wherein the amino acid at 234 is substituted to Val, wherein the residues are numbered according to the EU index.

In some embodiments, an Fc variant further comprises amino acid substitutions at 235 and 237. In some embodiments, an Fc variant further comprises amino acid substitutions at 235, 237, 330 and 331. In some embodiments, an Fc variant further comprises an amino acid substitution at 235.

In some embodiments, an antibody or a fragment thereof comprises an Fc variant of a wild-type human IgG4 Fc region, said Fc variant comprising an amino acid substitutions at positions F234, L235, and D265, wherein the residues are numbered according to the EU index.

In some embodiments, an antibody or a fragment thereof comprises an Fc variant of a wild-type human IgG Fc region, said Fc variant comprising an amino acid substitutions of 234V, L235E, and D265G, wherein the residues are numbered according to the EU index.

In some embodiments, an Fc variant is IgG4 Fc region. In some embodiments, an Fc variant comprises amino acid substitutions of S228P, F234V, L235E, and D265G. In some embodiments, an Fc variant is IgG4 Fc region and comprises amino acid substitutions of S228P, F234V, L235E, and D265G.

In some embodiments, an antibody or a fragment thereof comprises an Fc variant of a wild-type human IgG Fc region, said Fc variant comprising an amino acid substitutions of 234F, L235E, and D265G, wherein the residues are numbered according to the EU index.

In some embodiments, an Fc variant is IgG1 Fc region. In some embodiments, an Fc variant comprises amino acid substitutions of L234F, L235E, and D265G. In some embodiments, an Fc variant is IgG1 Fc region and comprises amino acid substitutions of L234F, L235E, and D265G.

In some embodiments, an antibody or a fragment thereof comprises an Fc variant of a wild-type human IgG Fc region, said Fc variant comprising an amino acid substitutions of 234F, L235E, G237A, and D265G, wherein the residues are numbered according to the EU index.

In some embodiments, an Fc variant is IgG1 Fc region. In some embodiments, an Fc variant comprises amino acid substitutions of L234F, L235E, G237A, and D265G. In some embodiments, an Fc variant is IgG1 Fc region and comprises amino acid substitutions of L234F, L235E, G237A, and D265G.

In some embodiments, an antibody or a fragment thereof comprises an Fc variant of a wild-type human IgG Fc region, said Fc variant comprising an amino acid substitutions of 234V, L235E, G237A, and D265G, wherein the residues are numbered according to the EU index.

In some embodiments, an Fc variant is IgG1 Fc region. In some embodiments, an Fc variant comprises amino acid substitutions of L234V, L235E, G237A, and D265G. In some embodiments, an Fc variant is IgG1 Fc region and comprises amino acid substitutions of L234V, L235E, G237A, and D265G.

In some embodiments, an antibody or a fragment thereof comprises an Fc variant of a wild-type human IgG Fc region, said Fc variant comprising an amino acid substitutions of 234F, L235E, D265D, A330S, and P331S, wherein the residues are numbered according to the EU index.

In some embodiments, an Fc variant is IgG1 Fc region. In some embodiments, an Fc variant comprises amino acid substitutions of L234F, L235E, D265D, A330S, and P331S. In some embodiments, an Fc variant is IgG1 Fc region and comprises amino acid substitutions of L234F, L235E, D265D, A330S, and P331S.

In some embodiments, an antibody or a fragment thereof comprises an Fc variant of a wild-type human IgG Fc region, said Fc variant comprising an amino acid substitutions of 234V, L235A, G237A, and D265G, wherein the residues are numbered according to the EU index.

In some embodiments, an Fc variant is IgG1 Fc region. In some embodiments, an Fc variant comprises amino acid substitutions of L234V, L235A, G237A, and D265G. In some embodiments, an Fc variant is IgG1 Fc region and comprises amino acid substitutions of 234F, L234V, L235A, G237A, and D265G. In some embodiments, an Fc variant is IgG4 Fc region. In some embodiments, an Fc variant comprises amino acid substitutions of S228P, L234V, L235A, G237A, and D265G. In some embodiments, an Fc variant is IgG4 Fc region and comprises amino acid substitutions of S228P, L234V, L235A, G237A, and D265G.

In some embodiments, an Fc variant comprises amino acid substitutions of S228P, L234V, L235A, G237A, D265G, T307Q, Q311V, and A378V. In some embodiments, an Fc variant is IgG4 Fc region and comprises amino acid substitutions of L234V, L235A, G237A, D265G, T307Q, Q311V, and A378V.

In some embodiments, an antibody or a fragment thereof comprises an Fc variant of a wild-type human IgG Fc region, said Fc variant comprising an amino acid substitutions of 234V, L235A, G237A, D265G, A330S, and P331S wherein the residues are numbered according to the EU index.

In some embodiments, an Fc variant is IgG1 Fc region. In some embodiments, an Fc variant comprises amino acid substitutions of L234V, L235A, G237A, D265G, A330S, and P331S. In some embodiments, an Fc variant is IgG1 Fc region and comprises amino acid substitutions of L234V, L235A, G237A, D265G, A330S, and P331S.

In some embodiments, an antibody or a fragment thereof comprises an Fc variant of a wild-type human IgG Fc region, said Fc variant comprising an amino acid substitutions of L235E and D265G, wherein the residues are numbered according to the EU index.

In some embodiments, an Fc variant is IgG4 Fc region. In some embodiments, an Fc variant comprises amino acid substitutions of S228P, L235E and D265G. In some embodiments, an Fc variant is IgG4 Fc region and comprises amino acid substitutions of S228P, L235E and D265G.

In some embodiments, an antibody or a fragment thereof comprises an Fc variant of a wild-type human IgG Fc region, said Fc variant comprising an amino acid substitutions of L235E, G237A, and D265G, wherein the residues are numbered according to the EU index.

In some embodiments, an Fc variant is IgG4 Fc region. In some embodiments, an Fc variant comprises amino acid substitutions of S228P, L235E, G237A, and D265G. In some embodiments, an Fc variant is IgG4 Fc region and comprises amino acid substitutions of S228P, L235E, G237A, and D265G.

In some embodiments, an antibody or a fragment thereof comprises an Fc variant of a wild-type human IgG Fc region, said Fc variant comprising an amino acid substitutions of L235E, G237A, and P329G, wherein the residues are numbered according to the EU index.

In some embodiments, an Fc variant is IgG4 Fc region. In some embodiments, an Fc variant comprises amino acid substitutions of S228P, L235E, G237A, and P329G. In some embodiments, an Fc variant is IgG4 Fc region and comprises amino acid substitutions of S228P, L235E, G237A, and P329G.

In some embodiments, an antibody or a fragment thereof comprises an Fc variant of a wild-type human IgG Fc region, said Fc variant comprising an amino acid substitutions of L235E, G237A, and L328R, wherein the residues are numbered according to the EU index.

In some embodiments, an Fc variant is IgG4 Fc region. In some embodiments, an Fc variant comprises amino acid substitutions of S228P, L235E, G237A, and L328R. In some embodiments, an Fc variant is IgG4 Fc region and comprises amino acid substitutions of S228P, L235E, G237A, and L328R.

In some embodiments, an antibody or a fragment thereof comprises an Fc variant of a wild-type human IgG Fc region, said Fc variant comprising an amino acid substitutions of D265G, A330S, and P331S, wherein the residues are numbered according to the EU index.

In some embodiments, an Fc variant is IgG2 Fc region. In some embodiments, an Fc variant comprises amino acid substitutions of D265G, A330S, and P331S. In some embodiments, an Fc variant is IgG2 Fc region and comprises amino acid substitutions of D265G, A330S, and P331S.

In some embodiments, an antibody or a fragment thereof comprises an Fc variant of a wild-type human IgG Fc region, said Fc variant comprising an amino acid substitutions of 235E, D265G, A330S, and P331S, wherein the residues are numbered according to the EU index.

In some embodiments, an Fc variant is IgG2 Fc region. In some embodiments, an Fc variant comprises amino acid substitutions of A235E, D265G, A330S, and P331S. In some embodiments, an Fc variant is IgG2 Fc region and comprises amino acid substitutions of A235E, D265G, A330S, and P331S.

In some embodiments, an antibody or a fragment thereof comprises an Fc variant of a wild-type human IgG Fc region, said Fc variant comprising an amino acid substitutions of 235E, D265G, and P329G, wherein the residues are numbered according to the EU index.

In some embodiments, an Fc variant is IgG2 Fc region. In some embodiments, an Fc variant comprises amino acid substitutions of A235E, D265G, and P329G. In some embodiments, an Fc variant is IgG2 Fc region and comprises amino acid substitutions of A235E, D265G, and P329G.

In some embodiments, an Fc variant comprises SEQ ID NO: 14.

(SEQ ID NO: 14)
ESKYGPPCPPCPAPEVEGGPSVFLFPPKPKDTLMISRTPEVTCVVVGVSQ

EDPEVQFNWYVDGVEVHNAKTKPREEQFNSTYRVVSVLQVLHVDWLNGKE

YKCKVSNKGLPSSIEKTISKAKGQPREPQVYTLPPSQEEMTKNQVSLTCL

VKGFYPSDIVVEWESNGQPENNYKTTPPVLDSDGSFFLYSRLTVDKSRWQ

EGNVFSCSVMHEALHNHYTQKSLSLSLGK

In some embodiments, an Fc variant comprises amino acid sequence 85% identical to SEQ ID NO: 14. In some embodiments, an Fc variant comprises amino acid sequence 90% identical to SEQ ID NO: 14. In some embodiments, an Fc variant comprises amino acid sequence 92% identical to SEQ ID NO: 14. In some embodiments, an Fc variant comprises amino acid sequence 95% identical to SEQ ID NO: 14. In some embodiments, an Fc variant comprises amino acid sequence 96% identical to SEQ ID NO: 14. In some embodiments, an Fc variant comprises amino acid sequence 97% identical to SEQ ID NO: 14. In some embodiments, an Fc variant comprises amino acid sequence 98% identical to SEQ ID NO: 14. In some embodiments, an Fc variant comprises amino acid sequence 99% identical to SEQ ID NO: 14. In some embodiments, an Fc variant comprises amino acid sequence identical to SEQ ID NO: 14.

Sequence of Anti-C3b Antibodies

In some embodiments, an antibody is comprised of two light chains and two heavy chains. In some embodiments, the heavy and light chains each comprise complementarity determining regions (CDRs) and framework regions. In some embodiments, an antibody or a fragment thereof is a VHH.

In some embodiments, a VHH comprises three CDRs: CDR1, CDR2, and CDR3 as identified by the amino acid sequences in Table A and Table B.

Exemplary anti-C3b antibody sequences are provided below:

TABLE A

CDR Sequences of Exemplary Anti-C3bVHHs based on Kabat convention

| | CDRs | | | | | |
|---|---|---|---|---|---|---|
| Ab | CDR1 | SEQ ID NO | CDR2 | SEQ ID NO | CDR3 | SEQ ID NO |
| Ab1 and Ab3 | NYHMG | 16 | TIIRTGTTIYY ADSVKG | 24 | ATSGWHIKTVTPYEY | 22 |
| Ab2 and Ab4 | NYHMG | 16 | TIIRHGTTIYY ADSVKG | 26 | ATSGWHIKTVTPYEY | 22 |
| Ab5 | NYHMG | 16 | TIIRTGETIYY ADSVKG | 17 | ATSGWNIKTVTPYEY | 18 |

TABLE A-continued

CDR Sequences of Exemplary Anti-C3bVHHs based on Kabat convention

| Ab | CDR1 | SEQ ID NO | CDR2 | SEQ ID NO | CDR3 | SEQ ID NO |
|---|---|---|---|---|---|---|
| Ab6 | NYHMG | 16 | TIIRTGKTIYY ADSVKG | 21 | ATSGWHIKTVTPYEY | 22 |

TABLE B

CDR Sequences of Exemplary Anti-C3b VHHs based on Chothia convention

| Ab | CDR1 | SEQ ID NO | CDR2 | SEQ ID NO | CDR3 | SEQ ID NO |
|---|---|---|---|---|---|---|
| Ab1 and Ab3 | GRTESNY | 19 | IRTGTT | 25 | ATSGWHIKTVTPYEY | 22 |
| Ab2 and Ab4 | GRTFSNY | 19 | IRHGTT | 27 | ATSGWHIKTVTPYEY | 22 |
| Ab5 | GRTESNY | 19 | IRTGET | 20 | ATSGWNIKTVTPYEY | 18 |
| Ab6 | GRTESNY | 19 | IRTGKT | 23 | ATSGWHIKTVTPYEY | 22 |

In some embodiments, an anti-C3b antibody or antigen binding fragment thereof comprises a VHH sequence of SEQ ID NO: 10.

(SEQ ID NO: 10)
EVQLLESGGGLVQPGGSLRLSCAASGRTFSNYHMGWFRQAPGQGREFVAT
IIRTGETIYYADSVKGRFTISRDNSKNTLYLQMNSLRAEDTAVYYCAAAT
SGWNIKTVTPYEYWGQGTLVTVSS

In some embodiments, an anti-C3b antibody or antigen binding fragment thereof comprises a VHH sequence of SEQ ID NO: 11.

(SEQ ID NO: 11)
EVQLLESGGGLVQPGGSLRLSCAASGRTFSNYHMGWFRQAPGQGREFVAT
IIRTGKTIYYADSVKGRFTISRDNSKNTLYLQMNSLRAEDTAVYYCAAAT
SGWHIKTVTPYEYWGQGTLVTVSS

In some embodiments, an anti-C3b antibody or antigen binding fragment thereof comprises a VHH sequence of SEQ ID NO: 12.

(SEQ ID NO: 12)
EVQLLESGGGLVQPGGSLRLSCAASGRTFSNYHMGWFRQAPGQGREFVAT
IIRTGTTIYYADSVKGRFTISRDNSKNTLYLQMNSLRAEDTAVYYCAAAT
SGWHIKTVTPYEYWGQGTLVTVSS

In some embodiments, an anti-C3b antibody or antigen binding fragment thereof comprises a VHH sequence of SEQ ID NO: 13.

(SEQ ID NO: 13)
EVQLLESGGGLVQPGGSLRLSCAASGRTFSNYHMGWFRQAPGQGREFVAT
IIRHGTTIYYADSVKGRFTISRDNSKNTLYLQMNSLRAEDTAVYYCAAAT
SGWHIKTVTPYEYWGQGTLVTVSS

In some embodiments, an anti-C3b antibody or antigen binding fragment thereof comprises a VHH fused to an Fc domain.

In some embodiments, an anti-C3b antibody or antigen binding fragment thereof comprises a VHH-Fc domain fusion of SEQ ID NO: 4.

(SEQ ID NO: 4)
EVQLLESGGGLVQPGGSLRLSCAASGRTFSNYHMGWFRQAPGQGREFVAT
IIRTGETIYYADSVKGRFTISRDNSKNTLYLQMNSLRAEDTAVYYCAAAT
SGWNIKTVTPYEYWGQGTLVTVSSESKYGPPCPPCPAPEVEGGPSVFLFP
PKPKDTLMISRTPEVTCVVVGVSQEDPEVQFNWYVDGVEVHNAKTKPREE
QFNSTYRVVSVLQVLHVDWLNGKEYKCKVSNKGLPSSIEKTISKAKGQPR
EPQVYTLPPSQEEMTKNQVSLTCLVKGFYPSDIVVEWESNGQPENNYKTT
PPVLDSDGSFFLYSRLTVDKSRWQEGNVFSCSVMHEALHNHYTQKSLSLS
LGK

In some embodiments, an anti-C3b antibody or antigen binding fragment thereof comprises a VHH-Fc domain fusion of SEQ ID NO: 5.

(SEQ ID NO: 5)
EVQLLESGGGLVQPGGSLRLSCAASGRTFSNYHMGWFRQAPGQGREFVAT
IIRTGKTIYYADSVKGRFTISRDNSKNTLYLQMNSLRAEDTAVYYCAAAT
SGWHIKTVTPYEYWGQGTLVTVSSESKYGPPCPPCPAPEVEGGPSVFLFP
PKPKDTLMISRTPEVTCVVVGVSQEDPEVQFNWYVDGVEVHNAKTKPREE
QFNSTYRVVSVLQVLHVDWLNGKEYKCKVSNKGLPSSIEKTISKAKGQPR
EPQVYTLPPSQEEMTKNQVSLTCLVKGFYPSDIVVEWESNGQPENNYKTT
PPVLDSDGSFFLYSRLTVDKSRWQEGNVFSCSVMHEALHNHYTQKSLSLS
LGK

In some embodiments, an anti-C3b antibody or antigen binding fragment thereof comprises a VHH-Fc domain fusion of SEQ ID NO: 6.

(SEQ ID NO: 6)
EVQLLESGGGLVQPGGSLRLSCAASGRTFSNYHMGWFRQAPGQGREFVAT
IIRTGTTIYYADSVKGRFTISRDNSKNTLYLQMNSLRAEDTAVYYCAAAT
SGWHIKTVTPYEYWGQGTLVTVSSESKYGPPCPPCPAPEVEGGPSVFLFP
PKPKDTLMISRTPEVTCVVVGVSQEDPEVQFNWYVDGVEVHNAKTKPREE
QFNSTYRVVSVLQVLHVDWLNGKEYKCKVSNKGLPSSIEKTISKAKGQPR
EPQVYTLPPSQEEMTKNQVSLTCLVKGFYPSDIVVEWESNGQPENNYKTT
PPVLDSDGSFFLYSRLTVDKSRWQEGNVFSCSVMHEALHNHYTQKSLSLS
LGK

In some embodiments, an anti-C3b antibody or antigen binding fragment thereof comprises a VHH-Fc domain fusion of SEQ ID NO: 7.

(SEQ ID NO: 7)
EVQLLESGGGLVQPGGSLRLSCAASGRTFSNYHMGWFRQAPGQGREFVAT

IIRHGTTIYYADSVKGRFTISRDNSKNTLYLQMNSLRAEDTAVYYCAAAT

SGWHIKTVTPYEYWGQGTLVTVSSESKYGPPCPPCPAPEVEGGPSVFLFP

PKPKDTLMISRTPEVTCVVVGVSQEDPEVQFNWYVDGVEVHNAKTKPREE

QFNSTYRVVSVLQVLHVDWLNGKEYKCKVSNKGLPSSIEKTISKAKGQPR

EPQVYTLPPSQEEMTKNQVSLTCLVKGFYPSDIVVEWESNGQPENNYKTT

PPVLDSDGSFFLYSRLTVDKSRWQEGNVFSCSVMHEALHNHYTQKSLSLS

LGK

In some embodiments, an anti-C3b antibody or antigen binding fragment thereof comprises a VHH-Fc domain fusion of SEQ ID NO: 8.

(SEQ ID NO: 8)
EVQLLESGGGLVQPGGSLRLSCAASGRTFSNYHMGWFRQAPGQGREFVAT

IIRTGETIYYADSVKGRFTISRDNSKNTLYLQMNSLRAEDTAVYYCAAAT

SGWNIKTVTPYEYWGQGTLVTVSSESKYGPPCPPCPAPEFLGGPSVFLFP

PKPKDTLMISRTPEVTCVVVDVSQEDPEVQFNWYVDGVEVHNAKTKPREE

QFNSTYRVVSVLTVLHQDWLNGKEYKCKVSNKGLPSSIEKTISKAKGQPR

EPQVYTLPPSQEEMTKNQVSLTCLVKGFYPSDIAVEWESNGQPENNYKTT

PPVLDSDGSFFLYSRLTVDKSRWQEGNVFSCSVMHEALHNHYTQKSLSLS

LGK

In some embodiments, an anti-C3b antibody or antigen binding fragment thereof comprises a VHH-Fc domain fusion of SEQ ID NO: 9.

(SEQ ID NO: 9)
EVQLLESGGGLVQPGGSLRLSCAASGRTFSNYHMGWFRQAPGQGREFVAT

IIRTGTTIYYADSVKGRFTISRDNSKNTLYLQMNSLRAEDTAVYYCAAAT

SGWHIKTVTPYEYWGQGTLVTVSSESKYGPPCPPCPAPEFLGGPSVFLFP

PKPKDTLMISRTPEVTCVVVDVSQEDPEVQFNWYVDGVEVHNAKTKPREE

QFNSTYRVVSVLTVLHQDWLNGKEYKCKVSNKGLPSSIEKTISKAKGQPR

EPQVYTLPPSQEEMTKNQVSLTCLVKGFYPSDIAVEWESNGQPENNYKTT

PPVLDSDGSFFLYSRLTVDKSRWQEGNVFSCSVMHEALHNHYTQKSLSLS

LGK

In some embodiments, an anti-C3b antibody according to the invention comprises CDR amino acid sequences with at least 75%, 78%, 80%, 82%, 85%, 87%, 90%, 91%, 92%, 93%, 94%, 95%, 96%, 97%, 98%, 99% or more identity with one or more of SEQ ID NO: 16-27.

In some embodiments, an anti-C3b antibody or a fragment thereof comprises: CDR1 amino acid sequence with at least 75% identity with SEQ ID NO: 16. In some embodiments, an anti-C3b antibody or a fragment thereof comprises: CDR1 amino acid sequence with at least 78% identity with SEQ ID NO: 16. In some embodiments, an anti-C3b antibody or a fragment thereof comprises: CDR1 amino acid sequence with at least 80% identity with SEQ ID NO: 16. In some embodiments, an anti-C3b antibody or a fragment thereof comprises: CDR1 amino acid sequence with at least 82% identity with SEQ ID NO: 16. In some embodiments, an anti-C3b antibody or a fragment thereof comprises: CDR1 amino acid sequence with at least 85% identity with SEQ ID NO: 16. In some embodiments, an anti-C3b antibody or a fragment thereof comprises: CDR1 amino acid sequence with at least 85% identity with SEQ ID NO: 16. In some embodiments, an anti-C3b antibody or a fragment thereof comprises: CDR1 amino acid sequence with at least 87% identity with SEQ ID NO: 16. In some embodiments, an anti-C3b antibody or a fragment thereof comprises: CDR1 amino acid sequence with at least 90% identity with SEQ ID NO: 16. In some embodiments, an anti-C3b antibody or a fragment thereof comprises: CDR1 amino acid sequence with at least 91% identity with SEQ ID NO: 16. In some embodiments, an anti-C3b antibody or a fragment thereof comprises: CDR1 amino acid sequence with at least 92% identity with SEQ ID NO: 16. In some embodiments, an anti-C3b antibody or a fragment thereof comprises: CDR1 amino acid sequence with at least 93% identity with SEQ ID NO: 16. In some embodiments, an anti-C3b antibody or a fragment thereof comprises: CDR1 amino acid sequence with at least 94% identity with SEQ ID NO: 16. In some embodiments, an anti-C3b antibody or a fragment thereof comprises: CDR1 amino acid sequence with at least 95% identity with SEQ ID NO: 16. In some embodiments, an anti-C3b antibody or a fragment thereof comprises: CDR1 amino acid sequence with at least 96% identity with SEQ ID NO: 16. In some embodiments, an anti-C3b antibody or a fragment thereof comprises: CDR1 amino acid sequence with at least 97% identity with SEQ ID NO: 16. In some embodiments, an anti-C3b antibody or a fragment thereof comprises: CDR1 amino acid sequence with at least 98% identity with SEQ ID NO: 16. In some embodiments, an anti-C3b antibody or a fragment thereof comprises: CDR1 amino acid sequence with at least 99% identity with SEQ ID NO: 16.

In some embodiments, an anti-C3b antibody or a fragment thereof comprises: CDR2 amino acid sequence with at least 75% identity with SEQ ID NO: 17. In some embodiments, an anti-C3b antibody or a fragment thereof comprises: CDR2 amino acid sequence with at least 78% identity with SEQ ID NO: 17. In some embodiments, an anti-C3b antibody or a fragment thereof comprises: CDR2 amino acid sequence with at least 80% identity with SEQ ID NO: 17. In some embodiments, an anti-C3b antibody or a fragment thereof comprises: CDR2 amino acid sequence with at least 82% identity with SEQ ID NO: 17. In some embodiments, an anti-C3b antibody or a fragment thereof comprises: CDR2 amino acid sequence with at least 85% identity with SEQ ID NO: 17. In some embodiments, an anti-C3b antibody or a fragment thereof comprises: CDR2 amino acid sequence with at least 85% identity with SEQ ID NO: 17. In some embodiments, an anti-C3b antibody or a fragment thereof comprises: CDR2 amino acid sequence with at least 87% identity with SEQ ID NO: 17. In some embodiments, an anti-C3b antibody or a fragment thereof comprises: CDR2 amino acid sequence with at least 90% identity with SEQ ID NO: 17. In some embodiments, an anti-C3b antibody or a fragment thereof comprises: CDR2 amino acid sequence with at least 91% identity with SEQ ID NO: 17. In some embodiments, an anti-C3b antibody or a fragment thereof comprises: CDR2 amino acid sequence with at least 92% identity with SEQ ID NO: 17. In some embodiments, an anti-C3b antibody or a fragment thereof comprises: CDR2 amino acid sequence with at least 93% identity with SEQ ID NO: 17. In some embodiments, an anti-C3b antibody or a fragment thereof comprises: CDR2 amino acid sequence with at least 94% identity with SEQ ID NO: 17. In some embodiments, an anti-C3b antibody or a fragment thereof comprises: CDR2 amino acid sequence with at least 95% identity with SEQ ID NO: 17. In some embodiments, an anti-C3b antibody or a fragment thereof comprises: CDR2 amino acid sequence with at least 96% identity with SEQ ID NO: 17. In some embodiments, an anti-C3b antibody or a fragment thereof comprises: CDR2 amino acid sequence with at least 97% identity with SEQ ID NO: 17. In some embodiments, an anti-C3b antibody or a fragment thereof comprises: CDR2 amino acid sequence with at least 98% identity with SEQ ID NO: 17. In some embodiments, an anti-C3b antibody or a fragment thereof comprises: CDR2 amino acid sequence with at least 99% identity with SEQ ID NO: 17.

In some embodiments, an anti-C3b antibody or a fragment thereof comprises: CDR3 amino acid sequence with at least 75% identity with SEQ ID NO: 18. In some embodiments, an anti-C3b antibody or a fragment thereof comprises: CDR3 amino acid sequence with at least 78% identity with SEQ ID NO: 18. In some embodiments, an anti-C3b antibody or a fragment thereof comprises: CDR3 amino acid sequence with at least 80% identity with SEQ ID NO: 18. In some embodiments, an anti-C3b antibody or a fragment thereof comprises: CDR3 amino acid sequence with at least 82% identity with SEQ ID NO: 18. In some embodiments, an anti-C3b antibody or a fragment thereof comprises: CDR3 amino acid sequence with at least 85% identity with SEQ ID NO: 18. In some embodiments, an anti-C3b antibody or a fragment thereof comprises: CDR3 amino acid sequence with at least 85% identity with SEQ ID NO: 18. In some embodiments, an anti-C3b antibody or a fragment thereof comprises: CDR3 amino acid sequence with at least 87% identity with SEQ ID NO: 18. In some embodiments, an anti-C3b antibody or a fragment thereof comprises: CDR3 amino acid sequence with at least 90% identity with SEQ ID NO: 18. In some embodiments, an anti-C3b antibody or a fragment thereof comprises: CDR3 amino acid sequence with at least 91% identity with SEQ ID NO: 18. In some embodiments, an anti-C3b antibody or a fragment thereof comprises: CDR3 amino acid sequence with at least 92% identity with SEQ ID NO: 18. In some embodiments, an anti-C3b antibody or a fragment thereof comprises: CDR3 amino acid sequence with at least 93% identity with SEQ ID NO: 18. In some embodiments, an anti-C3b antibody or a fragment thereof comprises: CDR3 amino acid sequence with at least 94% identity with SEQ ID NO: 18. In some embodiments, an anti-C3b antibody or a fragment thereof comprises: CDR3 amino acid sequence with at least 95% identity with SEQ ID NO: 18. In some embodiments, an anti-C3b antibody or a fragment thereof comprises: CDR3 amino acid sequence with at least 96% identity with SEQ ID NO: 18. In some embodiments, an anti-C3b antibody or a fragment thereof comprises: CDR3 amino acid sequence with at least 97% identity with SEQ ID NO: 18. In some embodiments, an anti-C3b antibody or a fragment thereof comprises: CDR3 amino acid sequence with at least 98% identity with SEQ ID NO: 18. In some embodiments, an anti-C3b antibody or a fragment thereof comprises: CDR3 amino acid sequence with at least 99% identity with SEQ ID NO: 18.

In some embodiments, an anti-C3b antibody or a fragment thereof comprises: CDR1 amino acid sequence with at least 75% identity with SEQ ID NO: 19. In some embodiments, an anti-C3b antibody or a fragment thereof comprises: CDR1 amino acid sequence with at least 78% identity with SEQ ID NO: 19. In some embodiments, an anti-C3b antibody or a fragment thereof comprises: CDR1 amino acid sequence with at least 80% identity with SEQ ID NO: 19. In some embodiments, an anti-C3b antibody or a fragment thereof comprises: CDR1 amino acid sequence with at least 82% identity with SEQ ID NO: 19. In some embodiments, an anti-C3b antibody or a fragment thereof comprises: CDR1 amino acid sequence with at least 85% identity with SEQ ID NO: 19. In some embodiments, an anti-C3b antibody or a fragment thereof comprises: CDR1 amino acid sequence with at least 85% identity with SEQ ID NO: 19. In some embodiments, an anti-C3b antibody or a fragment thereof comprises: CDR1 amino acid sequence with at least 87% identity with SEQ ID NO: 19. In some embodiments, an anti-C3b antibody or a fragment thereof comprises: CDR1 amino acid sequence with at least 90% identity with SEQ ID NO: 19. In some embodiments, an anti-C3b antibody or a fragment thereof comprises: CDR1 amino acid sequence with at least 91% identity with SEQ ID NO: 19. In some embodiments, an anti-C3b antibody or a fragment thereof comprises: CDR1 amino acid sequence with at least 92% identity with SEQ ID NO: 19. In some embodiments, an anti-C3b antibody or a fragment thereof comprises: CDR1 amino acid sequence with at least 93% identity with SEQ ID NO: 19. In some embodiments, an anti-C3b antibody or a fragment thereof comprises: CDR1 amino acid sequence with at least 94% identity with SEQ ID NO: 19. In some embodiments, an anti-C3b antibody or a fragment thereof comprises: CDR1 amino acid sequence with at least 95% identity with SEQ ID NO: 19. In some embodiments, an anti-C3b antibody or a fragment thereof comprises: CDR1 amino acid sequence with at least 96% identity with SEQ ID NO: 19. In some embodiments, an anti-C3b antibody or a fragment thereof comprises: CDR1 amino acid sequence with at least 97% identity with SEQ ID NO: 19. In some embodiments, an anti-C3b antibody or a fragment thereof comprises: CDR1 amino acid sequence with at least 98% identity with SEQ ID NO: 19. In some embodiments, an anti-C3b antibody or a fragment thereof comprises: CDR1 amino acid sequence with at least 99% identity with SEQ ID NO: 19.

In some embodiments, an anti-C3b antibody or a fragment thereof comprises: CDR2 amino acid sequence with at least 75% identity with SEQ ID NO: 20. In some embodiments, an anti-C3b antibody or a fragment thereof comprises: CDR2 amino acid sequence with at least 78% identity with SEQ ID NO: 20. In some embodiments, an anti-C3b antibody or a fragment thereof comprises: CDR2 amino acid sequence with at least 80% identity with SEQ ID NO: 20. In some embodiments, an anti-C3b antibody or a fragment thereof comprises: CDR2 amino acid sequence with at least 82% identity with SEQ ID NO: 20. In some embodiments, an anti-C3b antibody or a fragment thereof comprises: CDR2 amino acid sequence with at least 85% identity with SEQ ID NO: 20. In some embodiments, an anti-C3b antibody or a fragment thereof comprises: CDR2 amino acid sequence with at least 85% identity with SEQ ID NO: 20. In some embodiments, an anti-C3b antibody or a fragment thereof comprises: CDR2 amino acid sequence with at least 87% identity with SEQ ID NO: 20. In some embodiments, an anti-C3b antibody or a fragment thereof comprises: CDR2 amino acid sequence with at least 90% identity with SEQ ID NO: 20. In some embodiments, an anti-C3b antibody or a fragment thereof comprises: CDR2 amino acid sequence with at least 91% identity with SEQ ID NO: 20. In some embodiments, an anti-C3b antibody or a fragment thereof comprises: CDR2 amino acid sequence with at least 92% identity with SEQ ID NO: 20. In some embodiments, an anti-C3b antibody or a fragment thereof comprises: CDR2 amino acid sequence with at least 93% identity with SEQ ID NO: 20. In some embodiments, an anti-C3b antibody or a fragment thereof comprises: CDR2 amino acid sequence with at least 94% identity with SEQ ID NO: 20. In some embodiments, an anti-C3b antibody or a fragment thereof comprises: CDR2 amino acid sequence with at least 95% identity with SEQ ID NO: 20. In some embodiments, an anti-C3b antibody or a fragment thereof comprises: CDR2 amino acid sequence with at least 96% identity with SEQ ID NO: 20. In some embodiments, an anti-C3b antibody or a fragment thereof comprises: CDR2 amino acid sequence with at least 97% identity with SEQ ID NO: 20. In some embodiments, an anti-C3b antibody or a fragment thereof comprises: CDR2 amino acid sequence with at least 98% identity with SEQ ID NO: 20. In some embodiments, an anti-C3b antibody or a fragment thereof comprises: CDR2 amino acid sequence with at least 99% identity with SEQ ID NO: 20.

In some embodiments, an anti-C3b antibody or a fragment thereof comprises: CDR2 amino acid sequence with at least 75% identity with SEQ ID NO: 21. In some embodiments, an anti-C3b antibody or a fragment thereof comprises: CDR2 amino acid sequence with at least 78% identity with SEQ ID NO: 21. In some embodiments, an anti-C3b antibody or a fragment thereof comprises: CDR2 amino acid sequence with at least 80% identity with SEQ ID NO: 21. In some embodiments, an anti-C3b antibody or a fragment thereof comprises: CDR2 amino acid sequence with at least 82% identity with SEQ ID NO: 21. In some embodiments, an anti-C3b antibody or a fragment thereof comprises: CDR2 amino acid sequence with at least 85% identity with SEQ ID NO: 21. In some embodiments, an anti-C3b antibody or a fragment thereof comprises: CDR2 amino acid sequence with at least 85% identity with SEQ ID NO: 21. In some embodiments, an anti-C3b antibody or a fragment thereof comprises: CDR2 amino acid sequence with at least 87% identity with SEQ ID NO: 21. In some embodiments, an anti-C3b antibody or a fragment thereof comprises: CDR2 amino acid sequence with at least 90% identity with SEQ ID NO: 21. In some embodiments, an anti-C3b antibody or a fragment thereof comprises: CDR2 amino acid sequence with at least 91% identity with SEQ ID NO: 21. In some embodiments, an anti-C3b antibody or a fragment thereof comprises: CDR2 amino acid sequence with at least 92% identity with SEQ ID NO: 21. In some embodiments, an anti-C3b antibody or a fragment thereof comprises: CDR2 amino acid sequence with at least 93% identity with SEQ ID NO: 21. In some embodiments, an anti-C3b antibody or a fragment thereof comprises: CDR2 amino acid sequence with at least 94% identity with SEQ ID NO: 21. In some embodiments, an anti-C3b antibody or a fragment thereof comprises: CDR2 amino acid sequence with at least 95% identity with SEQ ID NO: 21. In some embodiments, an anti-C3b antibody or a fragment thereof comprises: CDR2 amino acid sequence with at least 96% identity with SEQ ID NO: 21. In some embodiments, an anti-C3b antibody or a fragment thereof comprises: CDR2 amino acid sequence with at least 97% identity with SEQ ID NO: 21. In some embodiments, an anti-C3b antibody or a fragment thereof comprises: CDR2 amino acid sequence with at least 98% identity with SEQ ID NO: 21. In some embodiments, an anti-C3b antibody or a fragment thereof comprises: CDR2 amino acid sequence with at least 99% identity with SEQ ID NO: 21.

In some embodiments, an anti-C3b antibody or a fragment thereof comprises: CDR3 amino acid sequence with at least 75% identity with SEQ ID NO: 22. In some embodiments, an anti-C3b antibody or a fragment thereof comprises: CDR3 amino acid sequence with at least 78% identity with SEQ ID NO: 22. In some embodiments, an anti-C3b antibody or a fragment thereof comprises: CDR3 amino acid sequence with at least 80% identity with SEQ ID NO: 22. In some embodiments, an anti-C3b antibody or a fragment thereof comprises: CDR3 amino acid sequence with at least 82% identity with SEQ ID NO: 22. In some embodiments, an anti-C3b antibody or a fragment thereof comprises: CDR3 amino acid sequence with at least 85% identity with SEQ ID NO: 22. In some embodiments, an anti-C3b antibody or a fragment thereof comprises: CDR3 amino acid sequence with at least 85% identity with SEQ ID NO: 22. In some embodiments, an anti-C3b antibody or a fragment thereof comprises: CDR3 amino acid sequence with at least 87% identity with SEQ ID NO: 22. In some embodiments, an anti-C3b antibody or a fragment thereof comprises: CDR3 amino acid sequence with at least 90% identity with SEQ ID NO: 22. In some embodiments, an anti-C3b antibody or a fragment thereof comprises: CDR3 amino acid sequence with at least 91% identity with SEQ ID NO: 22. In some embodiments, an anti-C3b antibody or a fragment thereof comprises: CDR3 amino acid sequence with at least 92% identity with SEQ ID NO: 22. In some embodiments, an anti-C3b antibody or a fragment thereof comprises: CDR3 amino acid sequence with at least 93% identity with SEQ ID NO: 22. In some embodiments, an anti-C3b antibody or a fragment thereof comprises: CDR3 amino acid sequence with at least 94% identity with SEQ ID NO: 22. In some embodiments, an anti-C3b antibody or a fragment thereof comprises: CDR3 amino acid sequence with at least 95% identity with SEQ ID NO: 22. In some embodiments, an anti-C3b antibody or a fragment thereof comprises: CDR3 amino acid sequence with at least 96% identity with SEQ ID NO: 22. In some embodiments, an anti-C3b antibody or a fragment thereof comprises: CDR3 amino acid sequence with at least 97% identity with SEQ ID NO: 22. In some embodiments, an anti-C3b antibody or a fragment thereof comprises: CDR3 amino acid sequence with at least 98% identity with SEQ ID NO: 22. In some embodiments, an anti-C3b antibody or a fragment thereof comprises: CDR3 amino acid sequence with at least 99% identity with SEQ ID NO: 22.

In some embodiments, an anti-C3b antibody or a fragment thereof comprises: CDR2 amino acid sequence with at least 75% identity with SEQ ID NO: 23. In some embodiments, an anti-C3b antibody or a fragment thereof comprises: CDR2 amino acid sequence with at least 78% identity with SEQ ID NO: 23. In some embodiments, an anti-C3b antibody or a fragment thereof comprises: CDR2 amino acid sequence with at least 80% identity with SEQ ID NO: 23. In some embodiments, an anti-C3b antibody or a fragment thereof comprises: CDR2 amino acid sequence with at least 82% identity with SEQ ID NO: 23. In some embodiments, an anti-C3b antibody or a fragment thereof comprises: CDR2 amino acid sequence with at least 85% identity with SEQ ID NO: 23. In some embodiments, an anti-C3b antibody or a fragment thereof comprises: CDR2 amino acid sequence with at least 85% identity with SEQ ID NO: 23. In some embodiments, an anti-C3b antibody or a fragment thereof comprises: CDR2 amino acid sequence with at least 87% identity with SEQ ID NO: 23. In some embodiments, an anti-C3b antibody or a fragment thereof comprises: CDR2 amino acid sequence with at least 90% identity with SEQ ID NO: 23. In some embodiments, an anti-C3b antibody or a fragment thereof comprises: CDR2 amino acid sequence with at least 91% identity with SEQ ID NO: 23. In some embodiments, an anti-C3b antibody or a fragment thereof comprises: CDR2 amino acid sequence with at least 92% identity with SEQ ID NO: 23. In some embodiments, an anti-C3b antibody or a fragment thereof comprises: CDR2 amino acid sequence with at least 93% identity with SEQ ID NO: 23. In some embodiments, an anti-C3b antibody or a fragment thereof comprises: CDR2 amino acid sequence with at least 94% identity with SEQ ID NO: 23. In some embodiments, an anti-C3b antibody or a fragment thereof comprises: CDR2 amino acid sequence with at least 95% identity with SEQ ID NO: 23. In some embodiments, an anti-C3b antibody or a fragment thereof comprises: CDR2 amino acid sequence with at least 96% identity with SEQ ID NO: 23. In some embodiments, an anti-C3b antibody or a fragment thereof comprises: CDR2 amino acid sequence with at least 97% identity with SEQ ID NO: 23. In some embodiments, an anti-C3b antibody or a fragment thereof comprises: CDR2 amino acid sequence with at least 98% identity with SEQ ID NO: 23. In some embodiments, an anti-C3b antibody or a fragment thereof comprises: CDR2 amino acid sequence with at least 99% identity with SEQ ID NO: 23.

In some embodiments, an anti-C3b antibody or a fragment thereof comprises: CDR2 amino acid sequence with at least 75% identity with SEQ ID NO: 24. In some embodiments, an anti-C3b antibody or a fragment thereof comprises: CDR2 amino acid sequence with at least 78% identity with SEQ ID NO: 24. In some embodiments, an anti-C3b antibody or a fragment thereof comprises: CDR2 amino acid sequence with at least 80% identity with SEQ ID NO: 24. In some embodiments, an anti-C3b antibody or a fragment thereof comprises: CDR2 amino acid sequence with at least 82% identity with SEQ ID NO: 24. In some embodiments, an anti-C3b antibody or a fragment thereof comprises: CDR2 amino acid sequence with at least 85% identity with SEQ ID NO: 24. In some embodiments, an anti-C3b antibody or a fragment thereof comprises: CDR2 amino acid sequence with at least 85% identity with SEQ ID NO: 24. In some embodiments, an anti-C3b antibody or a fragment thereof comprises: CDR2 amino acid sequence with at least 87% identity with SEQ ID NO: 24. In some embodiments, an anti-C3b antibody or a fragment thereof comprises: CDR2 amino acid sequence with at least 90% identity with SEQ ID NO: 24. In some embodiments, an anti-C3b antibody or a fragment thereof comprises: CDR2 amino acid sequence with at least 91% identity with SEQ ID NO: 24. In some embodiments, an anti-C3b antibody or a fragment thereof comprises: CDR2 amino acid sequence with at least 92% identity with SEQ ID NO: 24. In some embodiments, an anti-C3b antibody or a fragment thereof comprises: CDR2 amino acid sequence with at least 93% identity with SEQ ID NO: 24. In some embodiments, an anti-C3b antibody or a fragment thereof comprises: CDR2 amino acid sequence with at least 94% identity with SEQ ID NO: 24. In some embodiments, an anti-C3b antibody or a fragment thereof comprises: CDR2 amino acid sequence with at least 95% identity with SEQ ID NO: 24. In some embodiments, an anti-C3b antibody or a fragment thereof comprises: CDR2 amino acid sequence with at least 96% identity with SEQ ID NO: 24. In some embodiments, an anti-C3b antibody or a fragment thereof comprises: CDR2 amino acid sequence with at least 97% identity with SEQ ID NO: 24. In some embodiments, an anti-C3b antibody or a fragment thereof comprises: CDR2 amino acid sequence with at least 98% identity with SEQ ID NO: 24. In some embodiments, an anti-C3b antibody or a fragment thereof comprises: CDR2 amino acid sequence with at least 99% identity with SEQ ID NO: 24.

In some embodiments, an anti-C3b antibody or a fragment thereof comprises: CDR2 amino acid sequence with at least 75% identity with SEQ ID NO: 25. In some embodiments, an anti-C3b antibody or a fragment thereof comprises: CDR2 amino acid sequence with at least 78% identity with SEQ ID NO: 25. In some embodiments, an anti-C3b antibody or a fragment thereof comprises: CDR2 amino acid sequence with at least 80% identity with SEQ ID NO: 25. In some embodiments, an anti-C3b antibody or a fragment thereof comprises: CDR2 amino acid sequence with at least 82% identity with SEQ ID NO: 25. In some embodiments, an anti-C3b antibody or a fragment thereof comprises: CDR2 amino acid sequence with at least 85% identity with SEQ ID NO: 25. In some embodiments, an anti-C3b antibody or a fragment thereof comprises: CDR2 amino acid sequence with at least 85% identity with SEQ ID NO: 25. In some embodiments, an anti-C3b antibody or a fragment thereof comprises: CDR2 amino acid sequence with at least 87% identity with SEQ ID NO: 25. In some embodiments, an anti-C3b antibody or a fragment thereof comprises: CDR2 amino acid sequence with at least 90% identity with SEQ ID NO: 25. In some embodiments, an anti-C3b antibody or a fragment thereof comprises: CDR2 amino acid sequence with at least 91% identity with SEQ ID NO: 25. In some embodiments, an anti-C3b antibody or a fragment thereof comprises: CDR2 amino acid sequence with at least 92% identity with SEQ ID NO: 25. In some embodiments, an anti-C3b antibody or a fragment thereof comprises: CDR2 amino acid sequence with at least 93% identity with SEQ ID NO: 25. In some embodiments, an anti-C3b antibody or a fragment thereof comprises: CDR2 amino acid sequence with at least 94% identity with SEQ ID NO: 25. In some embodiments, an anti-C3b antibody or a fragment thereof comprises: CDR2 amino acid sequence with at least 95% identity with SEQ ID NO: 25. In some embodiments, an anti-C3b antibody or a fragment thereof comprises: CDR2 amino acid sequence with at least 96% identity with SEQ ID NO: 25. In some embodiments, an anti-C3b antibody or a fragment thereof comprises: CDR2 amino acid sequence with at least 97% identity with SEQ ID NO: 25. In some embodiments, an anti-C3b antibody or a fragment thereof comprises: CDR2 amino acid sequence with at least 98% identity with SEQ ID NO: 25. In some embodiments, an anti-C3b antibody or a fragment thereof comprises: CDR2 amino acid sequence with at least 99% identity with SEQ ID NO: 25.

In some embodiments, an anti-C3b antibody or a fragment thereof comprises: CDR2 amino acid sequence with at least 75% identity with SEQ ID NO: 26. In some embodiments, an anti-C3b antibody or a fragment thereof comprises: CDR2 amino acid sequence with at least 78% identity with SEQ ID NO: 26. In some embodiments, an anti-C3b antibody or a fragment thereof comprises: CDR2 amino acid sequence with at least 80% identity with SEQ ID NO: 26. In some embodiments, an anti-C3b antibody or a fragment thereof comprises: CDR2 amino acid sequence with at least 82% identity with SEQ ID NO: 26. In some embodiments, an anti-C3b antibody or a fragment thereof comprises: CDR2 amino acid sequence with at least 85% identity with SEQ ID NO: 26. In some embodiments, an anti-C3b antibody or a fragment thereof comprises: CDR2 amino acid sequence with at least 85% identity with SEQ ID NO: 26. In some embodiments, an anti-C3b antibody or a fragment thereof comprises: CDR2 amino acid sequence with at least 87% identity with SEQ ID NO: 26. In some embodiments, an anti-C3b antibody or a fragment thereof comprises: CDR2 amino acid sequence with at least 90% identity with SEQ ID NO: 26. In some embodiments, an anti-C3b antibody or a fragment thereof comprises: CDR2 amino acid sequence with at least 91% identity with SEQ ID NO: 26. In some embodiments, an anti-C3b antibody or a fragment thereof comprises: CDR2 amino acid sequence with at least 92% identity with SEQ ID NO: 26. In some embodiments, an anti-C3b antibody or a fragment thereof comprises: CDR2 amino acid sequence with at least 93% identity with SEQ ID NO: 26. In some embodiments, an anti-C3b antibody or a fragment thereof comprises: CDR2 amino acid sequence with at least 94% identity with SEQ ID NO: 26. In some embodiments, an anti-C3b antibody or a fragment thereof comprises: CDR2 amino acid sequence with at least 95% identity with SEQ ID NO: 26. In some embodiments, an anti-C3b antibody or a fragment thereof comprises: CDR2 amino acid sequence with at least 96% identity with SEQ ID NO: 26. In some embodiments, an anti-C3b antibody or a fragment thereof comprises: CDR2 amino acid sequence with at least 97% identity with SEQ ID NO: 26. In some embodiments, an anti-C3b antibody or a fragment thereof comprises: CDR2 amino acid sequence with at least 98% identity with SEQ ID NO: 26. In some embodiments, an anti-C3b antibody or a fragment thereof comprises: CDR2 amino acid sequence with at least 99% identity with SEQ ID NO: 26.

In some embodiments, an anti-C3b antibody or a fragment thereof comprises: CDR2 amino acid sequence with at least 75% identity with SEQ ID NO: 27. In some embodiments, an anti-C3b antibody or a fragment thereof comprises: CDR2 amino acid sequence with at least 78% identity with SEQ ID NO: 27. In some embodiments, an anti-C3b antibody or a fragment thereof comprises: CDR2 amino acid sequence with at least 80% identity with SEQ ID NO: 27. In some embodiments, an anti-C3b antibody or a fragment thereof comprises: CDR2 amino acid sequence with at least 82% identity with SEQ ID NO: 27. In some embodiments, an anti-C3b antibody or a fragment thereof comprises: CDR2 amino acid sequence with at least 85% identity with SEQ ID NO: 27. In some embodiments, an anti-C3b antibody or a fragment thereof comprises: CDR2 amino acid sequence with at least 85% identity with SEQ ID NO: 27. In some embodiments, an anti-C3b antibody or a fragment thereof comprises: CDR2 amino acid sequence with at least 87% identity with SEQ ID NO: 27. In some embodiments, an anti-C3b antibody or a fragment thereof comprises: CDR2 amino acid sequence with at least 90% identity with SEQ ID NO: 27. In some embodiments, an anti-C3b antibody or a fragment thereof comprises: CDR2 amino acid sequence with at least 91% identity with SEQ ID NO: 27. In some embodiments, an anti-C3b antibody or a fragment thereof comprises: CDR2 amino acid sequence with at least 92% identity with SEQ ID NO: 27. In some embodiments, an anti-C3b antibody or a fragment thereof comprises: CDR2 amino acid sequence with at least 93% identity with SEQ ID NO: 27. In some embodiments, an anti-C3b antibody or a fragment thereof comprises: CDR2 amino acid sequence with at least 94% identity with SEQ ID NO: 27. In some embodiments, an anti-C3b antibody or a fragment thereof comprises: CDR2 amino acid sequence with at least 95% identity with SEQ ID NO: 27. In some embodiments, an anti-C3b antibody or a fragment thereof comprises: CDR2 amino acid sequence with at least 96% identity with SEQ ID NO: 27. In some embodiments, an anti-C3b antibody or a fragment thereof comprises: CDR2 amino acid sequence with at least 97% identity with SEQ ID NO: 27. In some embodiments, an anti-C3b antibody or a fragment thereof comprises: CDR2 amino acid sequence with at least 98% identity with SEQ ID NO: 27. In some embodiments, an anti-C3b antibody or a fragment thereof comprises: CDR2 amino acid sequence with at least 99% identity with SEQ ID NO: 27.

In some embodiments, an anti-C3b antibody according to the invention comprises up to one, two, three, or four amino acid substitutions in one or more of the CDR sequences of SEQ ID NO: 16-27. In some embodiments, an anti-C3b antibody according to the invention comprises up to one, two, three, four, or five amino acid substitutions in one or more of the CDR sequences selected from SEQ ID NOs: 16-27.

In some embodiments, an anti-C3b antibody or a fragment thereof comprises one amino acid substitution in CDR1 of SEQ ID NO: 16. In some embodiments, an anti-C3b antibody or a fragment thereof comprises two amino acid substitutions in CDR1 of SEQ ID NO: 16. In some embodiments, an anti-C3b antibody or a fragment thereof comprises two amino acid substitutions in CDR1 of SEQ ID NO: 16. In some embodiments, an anti-C3b antibody or a fragment thereof comprises three amino acid substitutions in CDR1 of SEQ ID NO: 16. In some embodiments, an anti-C3b antibody or a fragment thereof comprises four amino acid substitutions in CDR1 of SEQ ID NO: 16. In some embodiments, an anti-C3b antibody or a fragment thereof comprises five amino acid substitutions in CDR1 of SEQ ID NO: 16.

In some embodiments, an anti-C3b antibody or a fragment thereof comprises one amino acid substitution in CDR2 of SEQ ID NO: 17. In some embodiments, an anti-C3b antibody or a fragment thereof comprises two amino acid substitutions in CDR2 of SEQ ID NO: 17. In some embodiments, an anti-C3b antibody or a fragment thereof comprises two amino acid substitutions in CDR2 of SEQ ID NO: 17. In some embodiments, an anti-C3b antibody or a fragment thereof comprises three amino acid substitutions in CDR2 of SEQ ID NO: 17. In some embodiments, an anti-C3b antibody or a fragment thereof comprises four amino acid substitutions in CDR2 of SEQ ID NO: 17. In some embodiments, an anti-C3b antibody or a fragment thereof comprises five amino acid substitutions in CDR2 of SEQ ID NO: 17.

In some embodiments, an anti-C3b antibody or a fragment thereof comprises one amino acid substitution in CDR3 of SEQ ID NO: 18. In some embodiments, an anti-C3b antibody or a fragment thereof comprises two amino acid substitutions in CDR3 of SEQ ID NO: 18. In some embodiments, an anti-C3b antibody or a fragment thereof comprises two amino acid substitutions in CDR3 of SEQ ID NO: 18. In some embodiments, an anti-C3b antibody or a fragment thereof comprises three amino acid substitutions in CDR3 of SEQ ID NO: 18. In some embodiments, an anti-C3b antibody or a fragment thereof comprises four amino acid substitutions in CDR3 of SEQ ID NO: 18. In some embodiments, an anti-C3b antibody or a fragment thereof comprises five amino acid substitutions in CDR3 of SEQ ID NO: 18.

In some embodiments, an anti-C3b antibody or a fragment thereof comprises one amino acid substitution in CDR1 of SEQ ID NO: 19. In some embodiments, an anti-C3b antibody or a fragment thereof comprises two amino acid substitutions in CDR1 of SEQ ID NO: 19. In some embodiments, an anti-C3b antibody or a fragment thereof comprises two amino acid substitutions in CDR1 of SEQ ID NO: 19. In some embodiments, an anti-C3b antibody or a fragment thereof comprises three amino acid substitutions in CDR1 of SEQ ID NO: 19. In some embodiments, an anti-C3b antibody or a fragment thereof comprises four amino acid substitutions in CDR1 of SEQ ID NO: 19. In some embodiments, an anti-C3b antibody or a fragment thereof comprises five amino acid substitutions in CDR1 of SEQ ID NO: 19.

In some embodiments, an anti-C3b antibody or a fragment thereof comprises one amino acid substitution in CDR2 of SEQ ID NO: 20. In some embodiments, an anti-C3b antibody or a fragment thereof comprises two amino acid substitutions in CDR2 of SEQ ID NO: 20. In some embodiments, an anti-C3b antibody or a fragment thereof comprises two amino acid substitutions in CDR2 of SEQ ID NO: 20. In some embodiments, an anti-C3b antibody or a fragment thereof comprises three amino acid substitutions in CDR2 of SEQ ID NO: 20. In some embodiments, an anti-C3b antibody or a fragment thereof comprises four amino acid substitutions in CDR2 of SEQ ID NO: 20. In some embodiments, an anti-C3b antibody or a fragment thereof comprises five amino acid substitutions in CDR2 of SEQ ID NO: 20.

In some embodiments, an anti-C3b antibody or a fragment thereof comprises one amino acid substitution in CDR2 of SEQ ID NO: 21. In some embodiments, an anti-C3b antibody or a fragment thereof comprises two amino acid substitutions in CDR2 of SEQ ID NO: 21. In some embodiments, an anti-C3b antibody or a fragment thereof comprises two amino acid substitutions in CDR2 of SEQ ID NO: 21. In some embodiments, an anti-C3b antibody or a fragment thereof comprises three amino acid substitutions in CDR2 of SEQ ID NO: 21. In some embodiments, an anti-C3b antibody or a fragment thereof comprises four amino acid substitutions in CDR2 of SEQ ID NO: 21. In some embodiments, an anti-C3b antibody or a fragment thereof comprises five amino acid substitutions in CDR2 of SEQ ID NO: 21.

In some embodiments, an anti-C3b antibody or a fragment thereof comprises one amino acid substitution in CDR3 of SEQ ID NO: 22. In some embodiments, an anti-C3b antibody or a fragment thereof comprises two amino acid substitutions in CDR3 of SEQ ID NO: 22. In some embodiments, an anti-C3b antibody or a fragment thereof comprises two amino acid substitutions in CDR3 of SEQ ID NO: 22. In some embodiments, an anti-C3b antibody or a fragment thereof comprises three amino acid substitutions in CDR3 of SEQ ID NO: 22. In some embodiments, an anti-C3b antibody or a fragment thereof comprises four amino acid substitutions in CDR3 of SEQ ID NO: 22. In some embodiments, an anti-C3b antibody or a fragment thereof comprises five amino acid substitutions in CDR3 of SEQ ID NO: 22.

In some embodiments, an anti-C3b antibody or a fragment thereof comprises one amino acid substitution in CDR2 of SEQ ID NO: 23. In some embodiments, an anti-C3b antibody or a fragment thereof comprises two amino acid substitutions in CDR2 of SEQ ID NO: 23. In some embodiments, an anti-C3b antibody or a fragment thereof comprises two amino acid substitutions in CDR2 of SEQ ID NO: 23. In some embodiments, an anti-C3b antibody or a fragment thereof comprises three amino acid substitutions in CDR2 of SEQ ID NO: 23. In some embodiments, an anti-C3b antibody or a fragment thereof comprises four amino acid substitutions in CDR2 of SEQ ID NO: 23. In some embodiments, an anti-C3b antibody or a fragment thereof comprises five amino acid substitutions in CDR2 of SEQ ID NO: 23.

In some embodiments, an anti-C3b antibody or a fragment thereof comprises one amino acid substitution in CDR2 of SEQ ID NO: 24. In some embodiments, an anti-C3b antibody or a fragment thereof comprises two amino acid substitutions in CDR2 of SEQ ID NO: 24. In some embodiments, an anti-C3b antibody or a fragment thereof comprises two amino acid substitutions in CDR2 of SEQ ID NO: 24. In some embodiments, an anti-C3b antibody or a fragment thereof comprises three amino acid substitutions in CDR2 of SEQ ID NO: 24. In some embodiments, an anti-C3b antibody or a fragment thereof comprises four amino acid substitutions in CDR2 of SEQ ID NO: 24. In some embodiments, an anti-C3b antibody or a fragment thereof comprises five amino acid substitutions in CDR2 of SEQ ID NO: 24.

In some embodiments, an anti-C3b antibody or a fragment thereof comprises one amino acid substitution in CDR2 of SEQ ID NO: 25. In some embodiments, an anti-C3b antibody or a fragment thereof comprises two amino acid substitutions in CDR2 of SEQ ID NO: 25. In some embodiments, an anti-C3b antibody or a fragment thereof comprises two amino acid substitutions in CDR2 of SEQ ID NO: 25. In some embodiments, an anti-C3b antibody or a fragment thereof comprises three amino acid substitutions in CDR2 of SEQ ID NO: 25. In some embodiments, an anti-C3b antibody or a fragment thereof comprises four amino acid substitutions in CDR2 of SEQ ID NO: 25. In some embodiments, an anti-C3b antibody or a fragment thereof comprises five amino acid substitutions in CDR2 of SEQ ID NO: 25.

In some embodiments, an anti-C3b antibody or a fragment thereof comprises one amino acid substitution in CDR2 of SEQ ID NO: 26. In some embodiments, an anti-C3b antibody or a fragment thereof comprises two amino acid substitutions in CDR2 of SEQ ID NO: 26. In some embodiments, an anti-C3b antibody or a fragment thereof comprises two amino acid substitutions in CDR2 of SEQ ID NO: 26. In some embodiments, an anti-C3b antibody or a fragment thereof comprises three amino acid substitutions in CDR2 of SEQ ID NO: 26. In some embodiments, an anti-C3b antibody or a fragment thereof comprises four amino acid substitutions in CDR2 of SEQ ID NO: 26. In some embodiments, an anti-C3b antibody or a fragment thereof comprises five amino acid substitutions in CDR2 of SEQ ID NO: 26.

In some embodiments, an anti-C3b antibody or a fragment thereof comprises one amino acid substitution in CDR2 of SEQ ID NO: 27. In some embodiments, an anti-C3b antibody or a fragment thereof comprises two amino acid substitutions in CDR2 of SEQ ID NO: 27. In some embodiments, an anti-C3b antibody or a fragment thereof comprises two amino acid substitutions in CDR2 of SEQ ID NO: 27. In some embodiments, an anti-C3b antibody or a fragment thereof comprises three amino acid substitutions in CDR2 of SEQ ID NO: 27. In some embodiments, an anti-C3b antibody or a fragment thereof comprises four amino acid substitutions in CDR2 of SEQ ID NO: 27. In some embodiments, an anti-C3b antibody or a fragment thereof comprises five amino acid substitutions in CDR2 of SEQ ID NO: 27.

In some embodiments, an anti-C3b antibody or a fragment thereof comprises a CDR1 defined by SEQ ID NO: 16. In some embodiments, an anti-C3b antibody or a fragment thereof comprises a CDR2 defined by SEQ ID NO: 17. In some embodiments, an anti-C3b antibody or a fragment thereof comprises a CDR3 defined by SEQ ID NO: 18. In some embodiments, an anti-C3b antibody or a fragment thereof comprises a CDR1 defined by SEQ ID NO: 19. In some embodiments, an anti-C3b antibody or a fragment thereof comprises a CDR2 defined by SEQ ID NO: 20. In some embodiments, an anti-C3b antibody or a fragment thereof comprises a CDR2 defined by SEQ ID NO: 21. In some embodiments, an anti-C3b antibody or a fragment thereof comprises a CDR3 defined by SEQ ID NO: 22. In some embodiments, an anti-C3b antibody or a fragment thereof comprises a CDR2 defined by SEQ ID NO: 23. In some embodiments, an anti-C3b antibody or a fragment thereof comprises a CDR2 defined by SEQ ID NO: 24. In some embodiments, an anti-C3b antibody or a fragment thereof comprises a CDR2 defined by SEQ ID NO: 25. In some embodiments, an anti-C3b antibody or a fragment thereof comprises a CDR2 defined by SEQ ID NO: 26. In some embodiments, an anti-C3b antibody or a fragment thereof comprises a CDR2 defined by SEQ ID NO: 27.

In some embodiments, an anti-C3b antibody or a fragment thereof comprises a CDR1 defined by SEQ ID NO: 16, a CDR2 defined by SEQ ID NO: 17, and a CDR3 defined by SEQ ID NO: 18. In some embodiments, an anti-C3b antibody or a fragment thereof comprises a CDR1 defined by SEQ ID NO: 19, a CDR2 defined by SEQ ID NO: 20, and a CDR3 defined by SEQ ID NO: 18. In some embodiments, an anti-C3b antibody or a fragment thereof comprises a CDR1 defined by SEQ ID NO: 16, a CDR2 defined by SEQ ID NO: 21, and a CDR3 defined by SEQ ID NO: 22. In some embodiments, an anti-C3b antibody or a fragment thereof comprises a CDR1 defined by SEQ ID NO: 19, a CDR2 defined by SEQ ID NO: 23, and a CDR3 defined by SEQ ID NO: 22. In some embodiments, an anti-C3b antibody or a fragment thereof comprises a CDR1 defined by SEQ ID NO: 16, a CDR2 defined by SEQ ID NO: 24, and a CDR3 defined by SEQ ID NO: 22. In some embodiments, an anti-C3b antibody or a fragment thereof comprises a CDR1 defined by SEQ ID NO: 19, a CDR2 defined by SEQ ID NO: 25, and a CDR3 defined by SEQ ID NO: 22. In some embodiments, an anti-C3b antibody or a fragment thereof comprises a CDR1 defined by SEQ ID NO: 16, a CDR2 defined by SEQ ID NO: 26, and a CDR3 defined by SEQ ID NO: 22. In some embodiments, an anti-C3b antibody or a fragment thereof comprises a CDR1 defined by SEQ ID NO: 19, a CDR2 defined by SEQ ID NO: 27, and a CDR3 defined by SEQ ID NO: 22.

In some embodiments of the invention, a heavy chain constant region of an anti-C3b antibody comprises CH1, hinge and CH2 domains derived from an IgG4 antibody fused to a CH3 domain derived from an IgG1 antibody. In some embodiments of the invention, a heavy chain constant region of an anti-C3b antibody is, or is derived from, an IgG1, IgG2, IgG3 or IgG4 heavy chain constant region. In some embodiments of the invention, a light chain constant region of an anti-C3b antibody is, or is derived from, a lambda or kappa light chain constant region.

In some embodiments, an antibody or antigen binding fragment thereof is a single chain variable fragment (ScFv) comprising at least any one of the CDR sequences of SEQ ID NO: 16-27. In some embodiments an antibody or antigen binding fragment thereof is a fusion molecule comprising at least any one of the CDR sequences of SEQ ID NO: 16-27. In some embodiments, an antibody or antigen binding fragment thereof is a bispecific antibody comprising at least one of the CDR sequences of SEQ ID NO: 16-27. In some embodiments, an antibody or antigen binding fragment thereof is a VHH comprising at least one of the CDR sequences of SEQ ID NO: 16-27.

In some embodiments, a VHH that binds to Cb3 comprises a CDR1 defined by SEQ ID NO: 16, a CDR2 defined by SEQ ID NO: 17, and a CDR3 defined by SEQ ID NO: 18. In some embodiments, a VHH that binds to Cb3 comprises a CDR1 defined by SEQ ID NO: 19, a CDR2 defined by SEQ ID NO: 20, a CDR3 defined by SEQ ID NO: 18. In some embodiments, a VHH that binds to Cb3 comprises a CDR1 defined by SEQ ID NO: 16, a CDR2 defined by SEQ ID NO: 21, and a CDR3 defined by SEQ ID NO: 22. In some embodiments, a VHH that binds to Cb3 comprises a CDR1 defined by SEQ ID NO: 19, a CDR2 defined by SEQ ID NO: 23, and a CDR3 defined by SEQ ID NO: 22. In some embodiments, a VHH that binds to Cb3 comprises a CDR1 defined by SEQ ID NO: 16, a CDR2 defined by SEQ ID NO: 24, and a CDR3 defined by SEQ ID NO: 22. In some embodiments, a VHH that binds to Cb3 comprises a CDR1 defined by SEQ ID NO: 19, a CDR2 defined by SEQ ID NO: 25, and a CDR3 defined by SEQ ID NO: 22. In some embodiments, a VHH that binds to Cb3 comprises a CDR1 defined by SEQ ID NO: 16, a CDR2 defined by SEQ ID NO: 26, and a CDR3 defined by SEQ ID NO: 22. In some embodiments, a VHH that binds to Cb3 comprises a CDR1 defined by SEQ ID NO: 19, a CDR2 defined by SEQ ID NO: 27, and a CDR3 defined by SEQ ID NO: 22.

In some embodiments, an antibody or antigen binding fragment thereof is a VHH-Fc fusion comprising at least one of the CDR sequences of SEQ ID NO: 16-27.

In some embodiments, a VHH-Fc fusion that binds to Cb3 comprises a CDR1 defined by SEQ ID NO: 16, a CDR2 defined by SEQ ID NO: 17, and a CDR3 defined by SEQ ID NO: 18. In some embodiments, a VHH-Fc fusion that binds to Cb3 comprises a CDR1 defined by SEQ ID NO: 19, a CDR2 defined by SEQ ID NO: 20, and a CDR3 defined by SEQ ID NO: 18. In some embodiments, a VHH-Fc fusion that binds to Cb3 comprises a CDR1 defined by SEQ ID NO: 16, a CDR2 defined by SEQ ID NO: 21, and a CDR3 defined by SEQ ID NO: 22. In some embodiments a VHH-Fc fusion that binds to Cb3 comprises a CDR1 defined by SEQ ID NO: 19, a CDR2 defined by SEQ ID NO: 23, and a CDR3 defined by SEQ ID NO: 22. In some embodiments, a VHH-Fc fusion that binds to Cb3 comprises a CDR1 defined by SEQ ID NO: 16, a CDR2 defined by SEQ ID NO: 24, and a CDR3 defined by SEQ ID NO: 22. In some embodiments, a VHH-Fc fusion that binds to Cb3 comprises a CDR1 defined by SEQ ID NO: 19, a CDR2 defined by SEQ ID NO: 25, and a CDR3 defined by SEQ ID NO: 22. In some embodiments, a VHH-Fc fusion that binds to Cb3 comprises a CDR1 defined by SEQ ID NO: 16, a CDR2 defined by SEQ ID NO: 26, and a CDR3 defined by SEQ ID NO: 22. In some embodiments, a VHH-Fc fusion that binds to Cb3 comprises a CDR1 defined by SEQ ID NO: 19, a CDR2 defined by SEQ ID NO: 27, and a CDR3 defined by SEQ ID NO: 22.

In some embodiments, an anti-C3b antibody or antigen binding fragment thereof comprises a VHH sequence at least 85% identical to SEQ ID NO: 10. In some embodiments, an anti-C3b antibody or antigen binding fragment thereof comprises a VHH sequence at least 88% identical to SEQ ID NO: 10. In some embodiments, an anti-C3b antibody or antigen binding fragment thereof comprises a VHH sequence at least 90% identical to SEQ ID NO: 10. In some embodiments, an anti-C3b antibody or antigen binding fragment thereof comprises a VHH sequence at least 92% identical to SEQ ID NO: 10. In some embodiments, an anti-C3b antibody or antigen binding fragment thereof comprises a VHH sequence at least 95% identical to SEQ ID NO: 10. In some embodiments, an anti-C3b antibody or antigen binding fragment thereof comprises a VHH sequence at least 97% identical to SEQ ID NO: 10. In some embodiments, an anti-C3b antibody or antigen binding fragment thereof comprises a VHH sequence at least 98% identical to SEQ ID NO: 10. In some embodiments, an anti-C3b antibody or antigen binding fragment thereof comprises a VHH sequence at least 99% identical to SEQ ID NO: 10.

In some embodiments, an anti-C3b antibody or antigen binding fragment thereof comprises a VHH sequence at least 85% identical to SEQ ID NO: 11. In some embodiments, an anti-C3b antibody or antigen binding fragment thereof comprises a VHH sequence at least 88% identical to SEQ ID NO: 11. In some embodiments, an anti-C3b antibody or antigen binding fragment thereof comprises a VHH sequence at least 90% identical to SEQ ID NO: 11. In some embodiments, an anti-C3b antibody or antigen binding fragment thereof comprises a VHH sequence at least 92% identical to SEQ ID NO: 11. In some embodiments, an anti-C3b antibody or antigen binding fragment thereof comprises a VHH sequence at least 95% identical to SEQ ID NO: 11. In some embodiments, an anti-C3b antibody or antigen binding fragment thereof comprises a VHH sequence at least 97% identical to SEQ ID NO: 11. In some embodiments, an anti-C3b antibody or antigen binding fragment thereof comprises a VHH sequence at least 98% identical to SEQ ID NO: 11. In some embodiments, an anti-C3b antibody or antigen binding fragment thereof comprises a VHH sequence at least 99% identical to SEQ ID NO: 11.

In some embodiments, an anti-C3b antibody or antigen binding fragment thereof comprises a VHH sequence at least 85% identical to SEQ ID NO: 12. In some embodiments, an anti-C3b antibody or antigen binding fragment thereof comprises a VHH sequence at least 88% identical to SEQ ID NO: 12. In some embodiments, an anti-C3b antibody or antigen binding fragment thereof comprises a VHH sequence at least 90% identical to SEQ ID NO: 12. In some embodiments, an anti-C3b antibody or antigen binding fragment thereof comprises a VHH sequence at least 92% identical to SEQ ID NO: 12. In some embodiments, an anti-C3b antibody or antigen binding fragment thereof comprises a VHH sequence at least 95% identical to SEQ ID NO: 12. In some embodiments, an anti-C3b antibody or antigen binding fragment thereof comprises a VHH sequence at least 97% identical to SEQ ID NO: 12. In some embodiments, an anti-C3b antibody or antigen binding fragment thereof comprises a VHH sequence at least 98% identical to SEQ ID NO: 12. In some embodiments, an anti-C3b antibody or antigen binding fragment thereof comprises a VHH sequence at least 99% identical to SEQ ID NO: 12.

In some embodiments, an anti-C3b antibody or antigen binding fragment thereof comprises a VHH sequence at least 85% identical to SEQ ID NO: 13. In some embodiments, an anti-C3b antibody or antigen binding fragment thereof comprises a VHH sequence at least 88% identical to SEQ ID NO: 13. In some embodiments, an anti-C3b antibody or antigen binding fragment thereof comprises a VHH sequence at least 90% identical to SEQ ID NO: 13. In some embodiments, an anti-C3b antibody or antigen binding fragment thereof comprises a VHH sequence at least 92% identical to SEQ ID NO: 13. In some embodiments, an anti-C3b antibody or antigen binding fragment thereof comprises a VHH sequence at least 95% identical to SEQ ID NO: 13. In some embodiments, an anti-C3b antibody or antigen binding fragment thereof comprises a VHH sequence at least 97% identical to SEQ ID NO: 13. In some embodiments, an anti-C3b antibody or antigen binding fragment thereof comprises a VHH sequence at least 98% identical to SEQ ID NO: 13. In some embodiments, an anti-C3b antibody or antigen binding fragment thereof comprises a VHH sequence at least 99% identical to SEQ ID NO: 13.

In some embodiments, an anti-C3b antibody or antigen binding fragment thereof comprises a VHH-Fc domain sequence at least 85% identical to SEQ ID NO: 4. In some embodiments, an anti-C3b antibody or antigen binding fragment thereof comprises a VHH-Fc domain sequence at least 88% identical to SEQ ID NO: 4. In some embodiments, an anti-C3b antibody or antigen binding fragment thereof comprises a VHH-Fc domain sequence at least 90% identical to SEQ ID NO: 4. In some embodiments, an anti-C3b antibody or antigen binding fragment thereof comprises a VHH-Fc domain sequence at least 92% identical to SEQ ID NO: 4. In some embodiments, an anti-C3b antibody or antigen binding fragment thereof comprises a VHH-Fc domain sequence at least 95% identical to SEQ ID NO: 4. In some embodiments, an anti-C3b antibody or antigen binding fragment thereof comprises a VHH-Fc domain sequence at least 96% identical to SEQ ID NO: 4. In some embodiments, an anti-C3b antibody or antigen binding fragment thereof comprises a VHH-Fc domain sequence at least 97% identical to SEQ ID NO: 4. In some embodiments, an anti-C3b antibody or antigen binding fragment thereof comprises a VHH-Fc domain sequence at least 98% identical to SEQ ID NO: 4. In some embodiments, an anti-C3b antibody or antigen binding fragment thereof comprises a VHH-Fc domain sequence at least 99% identical to SEQ ID NO: 4.

In some embodiments, an anti-C3b antibody or antigen binding fragment thereof comprises a VHH-Fc domain sequence at least 85% identical to SEQ ID NO: 5. In some embodiments, an anti-C3b antibody or antigen binding fragment thereof comprises a VHH-Fc domain sequence at least 88% identical to SEQ ID NO: 5. In some embodiments, an anti-C3b antibody or antigen binding fragment thereof comprises a VHH-Fc domain sequence at least 90% identical to SEQ ID NO: 5. In some embodiments, an anti-C3b antibody or antigen binding fragment thereof comprises a VHH-Fc domain sequence at least 92% identical to SEQ ID NO: 5. In some embodiments, an anti-C3b antibody or antigen binding fragment thereof comprises a VHH-Fc domain sequence at least 95% identical to SEQ ID NO: 5. In some embodiments, an anti-C3b antibody or antigen binding fragment thereof comprises a VHH-Fc domain sequence at least 96% identical to SEQ ID NO: 5. In some embodiments, an anti-C3b antibody or antigen binding fragment thereof comprises a VHH-Fc domain sequence at least 97% identical to SEQ ID NO: 5. In some embodiments, an anti-C3b antibody or antigen binding fragment thereof comprises a VHH-Fc domain sequence at least 98% identical to SEQ ID NO: 5. In some embodiments, an anti-C3b antibody or antigen binding fragment thereof comprises a VHH-Fc domain sequence at least 99% identical to SEQ ID NO: 5.

In some embodiments, an anti-C3b antibody or antigen binding fragment thereof comprises a VHH-Fc domain sequence at least 85% identical to SEQ ID NO: 6. In some embodiments, an anti-C3b antibody or antigen binding fragment thereof comprises a VHH-Fc domain sequence at least 88% identical to SEQ ID NO: 6. In some embodiments, an anti-C3b antibody or antigen binding fragment thereof comprises a VHH-Fc domain sequence at least 90% identical to SEQ ID NO: 6. In some embodiments, an anti-C3b antibody or antigen binding fragment thereof comprises a VHH-Fc domain sequence at least 92% identical to SEQ ID NO: 6. In some embodiments, an anti-C3b antibody or antigen binding fragment thereof comprises a VHH-Fc domain sequence at least 95% identical to SEQ ID NO: 6. In some embodiments, an anti-C3b antibody or antigen binding fragment thereof comprises a VHH-Fc domain sequence at least 96% identical to SEQ ID NO: 6. In some embodiments, an anti-C3b antibody or antigen binding fragment thereof comprises a VHH-Fc domain sequence at least 97% identical to SEQ ID NO: 6. In some embodiments, an anti-C3b antibody or antigen binding fragment thereof comprises a VHH-Fc domain sequence at least 98% identical to SEQ ID NO: 6. In some embodiments, an anti-C3b antibody or antigen binding fragment thereof comprises a VHH-Fc domain sequence at least 99% identical to SEQ ID NO: 6.

In some embodiments, an anti-C3b antibody or antigen binding fragment thereof comprises a VHH-Fc domain sequence at least 85% identical to SEQ ID NO: 7. In some embodiments, an anti-C3b antibody or antigen binding fragment thereof comprises a VHH-Fc domain sequence at least 88% identical to SEQ ID NO: 7. In some embodiments, an anti-C3b antibody or antigen binding fragment thereof comprises a VHH-Fc domain sequence at least 90% identical to SEQ ID NO: 7. In some embodiments, an anti-C3b antibody or antigen binding fragment thereof comprises a VHH-Fc domain sequence at least 92% identical to SEQ ID NO: 7. In some embodiments, an anti-C3b antibody or antigen binding fragment thereof comprises a VHH-Fc domain sequence at least 95% identical to SEQ ID NO: 7. In some embodiments, an anti-C3b antibody or antigen binding fragment thereof comprises a VHH-Fc domain sequence at least 96% identical to SEQ ID NO: 7. In some embodiments, an anti-C3b antibody or antigen binding fragment thereof comprises a VHH-Fc domain sequence at least 97% identical to SEQ ID NO: 7. In some embodiments, an anti-C3b antibody or antigen binding fragment thereof comprises a VHH-Fc domain sequence at least 98% identical to SEQ ID NO: 7. In some embodiments, an anti-C3b antibody or antigen binding fragment thereof comprises a VHH-Fc domain sequence at least 99% identical to SEQ ID NO: 7.

In some embodiments, an anti-C3b antibody or antigen binding fragment thereof comprises a VHH-Fc domain sequence at least 85% identical to SEQ ID NO: 8. In some embodiments, an anti-C3b antibody or antigen binding fragment thereof comprises a VHH-Fc domain sequence at least 88% identical to SEQ ID NO: 8. In some embodiments, an anti-C3b antibody or antigen binding fragment thereof comprises a VHH-Fc domain sequence at least 90% identical to SEQ ID NO: 8. In some embodiments, an anti-C3b antibody or antigen binding fragment thereof comprises a VHH-Fc domain sequence at least 92% identical to SEQ ID NO: 8. In some embodiments, an anti-C3b antibody or antigen binding fragment thereof comprises a VHH-Fc domain sequence at least 95% identical to SEQ ID NO: 8. In some embodiments, an anti-C3b antibody or antigen binding fragment thereof comprises a VHH-Fc domain sequence at least 96% identical to SEQ ID NO: 8. In some embodiments, an anti-C3b antibody or antigen binding fragment thereof comprises a VHH-Fc domain sequence at least 97% identical to SEQ ID NO: 8. In some embodiments, an anti-C3b antibody or antigen binding fragment thereof comprises a VHH-Fc domain sequence at least 98% identical to SEQ ID NO: 8. In some embodiments, an anti-C3b antibody or antigen binding fragment thereof comprises a VHH-Fc domain sequence at least 99% identical to SEQ ID NO: 8.

In some embodiments, an anti-C3b antibody or antigen binding fragment thereof comprises a VHH-Fc domain sequence at least 85% identical to SEQ ID NO: 9. In some embodiments, an anti-C3b antibody or antigen binding fragment thereof comprises a VHH-Fc domain sequence at least 88% identical to SEQ ID NO: 9. In some embodiments, an anti-C3b antibody or antigen binding fragment thereof comprises a VHH-Fc domain sequence at least 90% identical to SEQ ID NO: 9. In some embodiments, an anti-C3b antibody or antigen binding fragment thereof comprises a VHH-Fc domain sequence at least 92% identical to SEQ ID NO: 9. In some embodiments, an anti-C3b antibody or antigen binding fragment thereof comprises a VHH-Fc domain sequence at least 95% identical to SEQ ID NO: 9. In some embodiments, an anti-C3b antibody or antigen binding fragment thereof comprises a VHH-Fc domain sequence at least 96% identical to SEQ ID NO: 9. In some embodiments, an anti-C3b antibody or antigen binding fragment thereof comprises a VHH-Fc domain sequence at least 97% identical to SEQ ID NO: 9. In some embodiments, an anti-C3b antibody or antigen binding fragment thereof comprises a VHH-Fc domain sequence at least 98% identical to SEQ ID NO: 9. In some embodiments, an anti-C3b antibody or antigen binding fragment thereof comprises a VHH-Fc domain sequence at least 99% identical to SEQ ID NO: 9.

In other embodiments, a suitable C3b antagonist is an anti-C3b antibody. An anti-C3b antibody of the present disclosure may be multispecific, e.g., bispecific. An antibody of the may be mammalian (e.g., human, llama, or mouse), humanized, chimeric, recombinant, synthetically produced, or naturally isolated. Exemplary antibodies of the present disclosure include, without limitation, IgG (e.g., IgG1, IgG2, IgG3, and IgG4), IgM, IgA (e.g., IgA1, IgA2, and IgAsec), IgD, IgE, Fab, Fab', Fab'2, F(ab')2, Fd, Fv, Feb, scFv, scFv-Fc, and SMIP binding moieties. In certain embodiments, the antibody is a scFv. The scFv may include, for example, a flexible linker allowing the scFv to orient in different directions to enable antigen binding. In various embodiments, the antibody may be a cytosol-stable scFv or intrabody that retains its structure and function in the reducing environment inside a cell (see, e.g., Fisher and DeLisa, J. Mol. Biol. 385(1): 299-311, 2009; incorporated by reference herein). In particular embodiments, the scFv is converted to an IgG or a chimeric antigen receptor according to methods known in the art. In embodiments, the antibody binds to both denatured and native protein targets. In embodiments, the antibody binds to either denatured or native protein.

In most mammals, including humans, whole antibodies have at least two heavy (H) chains and two light (L) chains connected by disulfide bonds. Each heavy chain consists of a heavy chain variable region (VH) and a heavy chain constant region (CH). The heavy chain constant region consists of three domains (CH1, CH2, and CH3) and a hinge region between CH1 and CH2. Each light chain consists of a light chain variable region (VL) and a light chain constant region (CL). The light chain constant region consists of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

Antibodies include all known forms of antibodies and other protein scaffolds with antibody-like properties. For example, the anti-C3b antibody can be a monoclonal antibody, a polyclonal antibody, human antibody, a humanized antibody, a bispecific antibody, a monovalent antibody, a chimeric antibody, or a protein scaffold with antibody-like properties, such as fibronectin or ankyrin repeats. The antibody can have any of the following isotypes: IgG (e.g., IgG1, IgG2, IgG3, and IgG4), IgM, IgA (e.g., IgA1, IgA2, and IgAsec), IgD, or IgE.

An antibody fragment may include one or more segments derived from an antibody. A segment derived from an antibody may retain the ability to specifically bind to a particular antigen. An antibody fragment may be, e.g., a Fab, Fab', Fab'2, F(ab')2, Fd, Fv, Feb, scFv, or SMIP. An antibody fragment may be, e.g., a diabody, triabody, affibody, nanobody (VhH), aptamer, domain antibody, linear antibody, single-chain antibody, or any of a variety of multispecific antibodies that may be formed from antibody fragments.

Examples of antibody fragments include: (i) a Fab fragment: a monovalent fragment consisting of VL, VH, CL, and CH1 domains; (ii) a F(ab')2 fragment: a bivalent fragment comprising two Fab fragments linked by a disulfide bridge at the hinge region; (iii) a Fd fragment: a fragment consisting of VH and CH1 domains; (iv) an Fv fragment: a fragment consisting of the VL and VH domains of a single arm of an antibody; (v) a dAb fragment: a fragment including VH and VL domains; (vi) a dAb fragment: a fragment that is a VH domain; (vii) a dAb fragment: a fragment that is a VL domain; (viii) an isolated complementarity determining region (CDR); and (ix) a combination of two or more isolated CDRs which may optionally be joined by one or more synthetic linkers. Furthermore, although the two domains of the Fv fragment, VL and VH, are coded for by separate genes, they can be joined, using recombinant methods, e.g., by a synthetic linker that enables them to be expressed as a single protein, of which the VL and VH regions pair to form a monovalent binding moiety (known as a single chain Fv (scFv)). Antibody fragments may be obtained using conventional techniques known to those of skill in the art, and may, in some instances, be used in the same manner as intact antibodies. Antigen-binding fragments may be produced by recombinant DNA techniques or by enzymatic or chemical cleavage of intact immunoglobulins. An antibody fragment may further include any of the antibody fragments described above with the addition of additional C-terminal amino acids, N-terminal amino acids, or amino acids separating individual fragments.

An antibody may be referred to as chimeric if it includes one or more antigen-determining regions or constant regions derived from a first species and one or more antigen-determining regions or constant regions derived from a second species. Chimeric antibodies may be constructed, e.g., by genetic engineering. A chimeric antibody may include immunoglobulin gene segments belonging to different species (e.g., from a mouse and a human).

An antibody may be a human antibody. A human antibody refers to a binding moiety having variable regions in which both the framework and CDR regions are derived from human immunoglobulin sequences. Furthermore, if the antibody contains a constant region, the constant region also is derived from a human immunoglobulin sequence. A human antibody may include amino acid residues not identified in a human immunoglobulin sequence, such as one or more sequence variations, e.g., mutations. A variation or additional amino acid may be introduced, e.g., by human manipulation. A human antibody of the present disclosure is not chimeric.

An antibody may be humanized, meaning that an antibody that includes one or more antigen-determining regions (e.g., at least one CDR) substantially derived from a non-human immunoglobulin or antibody is manipulated to include at least one immunoglobulin domain substantially derived from a human immunoglobulin or antibody. An antibody may be humanized using the conversion methods described herein, for example, by inserting antigen-recognition sequences from a non-human antibody encoded by a first vector into a human framework encoded by a second vector. For example, the first vector may include a polynucleotide encoding the non-human antibody (or a fragment thereof) and a site-specific recombination motif, while the second vector may include a polynucleotide encoding a human framework and a site-specific recombination complementary to a site-specific recombination motif on the first vector. The site-specific recombination motifs may be positioned on each vector such that a recombination event results in the insertion of one or more antigen-determining regions from the non-human antibody into the human framework, thereby forming a polynucleotide encoding a humanized antibody.

In certain embodiments, an antibody is converted from scFv to an IgG (e.g., IgG1, IgG2, IgG3, and IgG4). There are various methods in the art for converting scFv fragments to IgG. One such method of converting scFv fragments to IgG is disclosed in US patent application publication number 20160362476, the contents of which are incorporated herein by reference.

Specificity of Anti-C3b Antibodies

In some embodiments, an anti-C3b antibody binds human or Cynomolgus C3b with a dissociation constant ($K_D$) of between 0.01 nM and 1000 nM. In some embodiments, $K_D$ is determined by surface plasma resonance assay (SPR). In some embodiments, $K_D$ is determined by ELISA.

In some embodiments, an anti-C3b antibody has selectivity for C3b over C3. In some embodiments, an anti-C3b antibody binds C3b, but does not bind C3. In some embodiments, an anti-C3b antibody described herein binds to C3b with a binding affinity to C3b that is more than 5 fold greater than a binding affinity to C3. In some embodiments, an anti-C3b antibody described herein binds to C3b with a binding affinity to C3b that is more than 6 fold greater than a binding affinity to C3. In some embodiments, an anti-C3b antibody described herein binds to C3b with a binding affinity to C3b that is more than 7 fold greater than a binding affinity to C3. In some embodiments, an anti-C3b antibody described herein binds to C3b with a binding affinity to C3b that is more than 8 fold greater than a binding affinity to C3. In some embodiments, an anti-C3b antibody described herein binds to C3b with a binding affinity to C3b that is more than 9 fold greater than a binding affinity to C3. In some embodiments, an anti-C3b antibody described herein binds to C3b with a binding affinity to C3b that is more than 10 fold greater than a binding affinity to C3. In some embodiments, an anti-C3b antibody described herein binds to C3b with a binding affinity to C3b that is more than 12 fold greater than a binding affinity to C3. In some embodiments, an anti-C3b antibody described herein binds to C3b with a binding affinity to C3b that is more than 15 fold greater than a binding affinity to C3. In some embodiments, an anti-C3b antibody described herein binds to C3b with a binding affinity to C3b that is more than 17 fold greater than a binding affinity to C3. In some embodiments, an anti-C3b antibody described herein binds to C3b with a binding affinity to C3b that is more than 20 fold greater than a binding affinity to C3. In some embodiments, an anti-C3b antibody described herein binds to C3b with a binding affinity to C3b that is more than 7 fold greater, 10 fold greater, 15 fold greater, 20 fold greater, 25 fold greater, or 30 fold greater than the binding affinity to C3. In some embodiments, an anti-C3b antibody described herein has greater than 2 fold selectivity for C3b over C3. In some embodiments, an anti-C3b antibody described herein has greater than 5 fold selectivity for C3b over C3. In some embodiments, an anti-C3b antibody described herein has greater than 7 fold selectivity for C3b over C3. In some embodiments, an anti-C3b antibody described herein has greater than 8 fold selectivity for C3b over C3. In some embodiments, an anti-C3b antibody described herein has greater than 10 fold selectivity for C3b over C3. In some embodiments, an anti-C3b antibody described herein has greater than 12 fold selectivity for C3b over C3. In some embodiments, an anti-C3b antibody described herein has greater than 15 fold selectivity for C3b over C3. In some embodiments, an anti-C3b antibody described herein has greater than 18 fold selectivity for C3b over C3. In some embodiments, an anti-C3b antibody described herein has greater than 20 fold selectivity for C3b over C3. In some embodiments, an anti-C3b antibody described herein has greater than 25 fold selectivity for C3b over C3. In some embodiments, an anti-C3b antibody described herein has greater than 30 fold selectivity for C3b over C3.

In some embodiments, an anti-C3b antibody binds C3 with a dissociation constant ($K_D$) greater than 100 nM. In some embodiments, an anti-C3b antibody binds C3 with a dissociation constant ($K_D$) greater than 150 nM. In some embodiments, an anti-C3b antibody binds C3 with a dissociation constant ($K_D$) greater than 200 nM. In some embodiments, an anti-C3b antibody binds C3 with a dissociation constant ($K_D$) greater than 250 nM. In some embodiments, an anti-C3b antibody binds C3 with a dissociation constant ($K_D$) greater than 300 nM. In some embodiments, an anti-C3b antibody binds C3 with a dissociation constant ($K_D$) greater than 350 nM. In some embodiments, an anti-C3b antibody binds C3 with a dissociation constant ($K_D$) greater than 400 nM. In some embodiments, an anti-C3b antibody binds C3 with a dissociation constant ($K_D$) greater than 450 nM. In some embodiments, an anti-C3b antibody binds C3 with a dissociation constant ($K_D$) greater than 500 nM. In some embodiments, $K_D$ is determined by surface plasma resonance assay (SPR). In some embodiments, $K_D$ is determined by ELISA.

In some embodiments, an anti-C3b antibody lacks effector function to prevent C3b bound cells from cytotoxic effects.

Potency of Anti-C3b Antibodies

In some embodiments, an anti-C3b antibody or a fragment thereof has EC50 of between 0.1 ng/mL and 100 ng/mL.

In some embodiments, an anti-C3b antibody or a fragment thereof has IC50 of between 0.1 nM and 100 nM. In some embodiments IC50 is measured by C3 deposition assay. In some embodiments, IC50 is measured by hemolytic assay.

Epitopes of Anti-C3b Antibodies

The exemplary anti-C3b antibodies described herein have properties based on the distinct epitope on C3b bound by the anti-C3b antibody. The term "epitope" means the amino acids of a target molecule that are contacted by an anti-C3b antibody, when the antibody is bound to the target molecule. An epitope can be contiguous or non-contiguous (e.g., (i) in a single-chain polypeptide, amino acid residues that are not contiguous to one another in the polypeptide sequence but that within the context of the target molecule are bound by an antibody, or (ii) in a multimeric proteins comprising two or more individual components (e.g., amino acid residues are present on one or more of the individual components but are still bound by the antibody). Epitope determinants can include chemically active surface groupings of molecules such as amino acids, sugar side chains, phosphoryl or sulfonyl groups, and can have specific three dimensional structural characteristics, and/or specific charge characteristics. Generally, antigen binding proteins specific for a particular target molecule will preferentially recognize an epitope on the target molecule in a complex mixture of proteins and/or macromolecules.

Methods of characterizing the epitope bound by an antigen binding protein are well known in the art, including, but not limited to, binning (cross-competition) (Miller et al "Epitope binning of murine monoclonal antibodies by a multiplexed pairing assay" J Immunol Methods (2011) 365, 118-25), peptide mapping (e.g., PEPSPOT™) (Albert et al "The B-cell Epitope of the Monoclonal Anti-Factor VIII Antibody ESH8 Characterized by Peptide Array Analysis" 2008 Thromb. Haemost. 99, 634-7), mutagenesis methods such as chimeras (Song et al "Epitope Mapping of Ibalizumab, a Humanized Anti-CD4 Monoclonal Antibody with Anti-HIV-1 Activity in Infected Patients" J. Virol. (2010) 84, 6935-6942), alanine scanning (Cunningham and Wells "High-resolution epitope mapping of HGH-receptor interactions by alanine-scanning mutagenesis" Science (1989) 244, 1081-1085), arginine scanning (Lim et al "A diversity of antibody epitopes can induce signaling through the erythropoietin receptor" Biochemistry (2010) 49, 3797-3804), HD exchange methods (Coates et al "Epitope mapping by amide hydrogen/deuterium exchange coupled with immobilization of antibody, on-line proteolysis, liquid chromatography and mass spectrometry" Rapid Commun. Mass Spectrom. (2009) 23 639-647), NMR cross saturation methods (Morgan et al "Precise epitope mapping of malaria parasite inhibitory antibodies by TROSY NMR cross-saturation" Biochemistry (2005) 44, 518-23), and crystallography (Gerhardt et al "Structure of IL-17A in complex with a potent, fully human neutralizing antibody" J. Mol. Biol (2009) 394, 905-21). The methods vary in the level of detail they provide as to the amino acids comprising the epitope.

Antibodies that have an identical epitope or overlapping epitope will often cross-compete for binding to the antigen. Thus, in certain embodiments, an antibody of the invention cross-competes with any one of Ab3-Ab35. To "cross-compete" or "cross-competition" means the antibodies compete for the same epitope or binding site on a target. Such competition can be determined by an assay in which the reference antigen binding protein (e.g., antibody or antigen-binding portion thereof) prevents or inhibits specific binding of a test antibody, and vice versa. Numerous types of competitive binding assays can be used to determine if a test molecule competes with a reference molecule for binding. Examples of assays that can be employed include solid phase direct or indirect radioimmunoassay (RIA), solid phase direct or indirect enzyme immunoassay (EIA), sandwich competition assay (see, e.g., Stahli et al. (1983) Methods in Enzymology 9:242-253), solid phase direct biotin-avidin EIA (see, e.g., Kirkland et al., (1986) J. Immunol. 137:3614-9), solid phase direct labeled assay, solid phase direct labeled sandwich assay, Luminex (Jia et al. "A novel method of Multiplexed Competitive Antibody Binning for the characterization of monoclonal antibodies" J. Immunological Methods (2004) 288, 91-98) and surface plasmon resonance (Song et al. "Epitope Mapping of Ibalizumab, a Humanized Anti-CD4 Monoclonal Antibody with Anti-HIV-1 Activity in Infected Patients" J. Virol. (2010) 84, 6935-42). Usually, when a competing antibody is present in excess, it will inhibit binding of a reference antigen binding protein to a common antigen by at least 50%, 55%, 60%, 65%, 70%, or 75%. In some instances, binding is inhibited by at least 80%, 85%, 90%, 95%, 96%, 97%, 98%, 99%, or more.

Nucleic Acid Encoding C3b Antagonists and Anti-C3b Antibodies

In some embodiments, the present invention provides, among other things a nucleic acid encoding a C3b antagonist or an anti-C3b antibody. In some embodiments, a nucleic acid encodes CDRs of the anti-C3b antibody of the present invention. In some embodiments, a nucleic acid encodes fragments of the anti-C3b antibody of the present invention. In some embodiments, a nucleic acid encodes variable regions of the anti-C3b antibody of the present invention. In some embodiments, a nucleic acid encodes a variable heavy chain and/or a variable light chain of the anti-C3b antibody of the present invention. In some embodiments, a nucleic acid encodes VHH of the anti-C3b antibody of the present invention. In some embodiments, a nucleic acid encodes anti-C3b VHH fused to an Fc domain.

In some embodiments, a nucleic acid is a DNA. In some embodiments, a nucleic acid is a cDNA. In some embodiments, a nucleic acid is a RNA. In some embodiments, a nucleic acid is a messenger RNA (mRNA).

In some embodiments, the present invention provides, among other things a messenger RNA (mRNA) encoding a C3b antagonist or an anti-C3b antibody. In some embodiments, an mRNA encodes CDRs of the anti-C3b antibody of the present invention. In some embodiments, an mRNA encodes fragments of the anti-C3b antibody of the present invention. In some embodiments, an mRNA encodes variable regions of the anti-C3b antibody of the present invention. In some embodiments, an mRNA encodes a variable heavy chain and/or a variable light chain of the anti-C3b antibody of the present invention. In some embodiments, an mRNA encodes VHH of the anti-C3b antibody of the present invention. In some embodiments, an mRNA encodes anti-C3b VHH fused to an Fc domain.

mRNA Encoding Anti-C3b Antibody and Antigen Binding Fragment Thereof

In some embodiments, the present invention provides an mRNA encoding an anti-C3b antibody or an antigen binding fragment thereof. In some embodiments, an mRNA encoding an anti-C3b antibody or an antigen binding fragment thereof is codon optimized. In some embodiments, the present invention provides methods and compositions for delivering codon optimized mRNA encoding an anti-C3b antibody or an antigen binding fragment thereof to a subject for the treatment of complement mediated disease. A suitable codon optimized mRNA encodes any full length, fragment or portion of an anti-C3b antibody, for example, CDRs, variable regions, variable heavy chain, variable light chain, scFv, VHH, or a VHH-Fc fusion.

Synthesis of mRNA mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7, or SP6 RNA polymerase), DNAse I, pyrophosphatase, and/or RNAse inhibitor. The exact conditions will vary according to the specific application.

Exemplary mRNA Construct

Construct Design:

5' UTR-mRNA encoding an antibody or a fragment thereof-3' UTR

Codon Optimization

According to an increasing amount of research, mRNAs contain numerous layers of information that overlap the amino acid code. Traditionally, codon optimization has been used to remove rare codons which were thought to be rate-limiting for protein expression. While fast growing bacteria and yeast both exhibit strong codon bias in highly expressed genes, higher eukaryotes exhibit much less codon bias, making it more difficult to discern codons that may be rate-limiting. In addition, it has been found that codon bias per se does not necessarily yield high expression but requires other features.

For example, rare codons have been implicated in slowing translation and forming pause sites, which may be required for correct protein folding. Therefore, variations in codon usage may provide a mechanism to fine-tune the temporal pattern of elongation and thus increase the time available for a protein to take on its correct confirmation. Codon optimization can interfere with this fine-tuning mechanism, resulting in less efficient protein translation or an increased amount of incorrectly folded proteins. Similarly, codon optimization may disrupt the normal patterns of cognate and wobble tRNA usage, thereby affecting protein structure and function because wobble-dependent slowing of elongation may likewise have been selected as a mechanism for achieving correct protein folding.

Various methods of performing codon optimization are known in the art, however, each has significant drawbacks and limitations from a computational and/or therapeutic point of view. In particular, known methods of codon optimization often involve, for each amino acid, replacing every codon with the codon having the highest usage for that amino acid, such that the "optimized" sequence contains only one codon encoding each amino acid (so may be referred to as a one-to-one sequence). The increase in expression is not limited to cell cultures of mammalian cells but was also observed in vivo in a mouse model. It is expected that the observed improvement in expression of the codon-optimized coding sequence will result in an improved, more cost-effective mRNA replacement therapy for patients in need thereof, because it does not require the use of modified nucleotides for the preparation of the mRNA and allows treatment with a reduced dose and/or at extended dosing intervals.

In some embodiments, codon-optimized mRNA is produced in accordance with methods known in the art.

Nucleotides

Various naturally-occurring or modified nucleosides may be used to product mRNA according to the present invention. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, pseudouridine, (e.g., N-1-methyl-pseudouridine), 2-thiouridine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

In some embodiments, the mRNA comprises one or more nonstandard nucleotide residues. The nonstandard nucleotide residues may include, e.g., 5-methylcytidine ("5mC"), pseudouridine ("ψU"), and/or 2-thio-uridine ("2sU"). See, e.g., U.S. Pat. No. 8,278,036 or WO2011012316 for a discussion of such residues and their incorporation into mRNA. The mRNA may be RNA, which is defined as RNA in which 25% of U residues are 2-thio-uridine and 25% of C residues are 5-methylcytidine. Teachings for the use of RNA are disclosed US Patent Publication US20120195936 and international publication WO2011012316, both of which are hereby incorporated by reference in their entirety. The presence of nonstandard nucleotide residues may render an mRNA more stable and/or less immunogenic than a control mRNA with the same sequence but containing only standard residues. In further embodiments, the mRNA may comprise one or more nonstandard nucleotide residues chosen from isocytosine, pseudoisocytosine, 5-bromouracil, 5-propynyluracil, 6-aminopurine, 2-aminopurine, inosine, diaminopurine and 2-chloro-6-aminopurine cytosine, as well as combinations of these modifications and other nucleobase modifications. Some embodiments may further include additional modifications to the furanose ring or nucleobase. Additional modifications may include, for example, sugar modifications or substitutions (e.g., one or more of a 2'-O-alkyl modification, a locked nucleic acid (LNA)). In some embodiments, the RNAs may be complexed or hybridized with additional polynucleotides and/or peptide polynucleotides (PNA). In some embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification. In some embodiments, any of these modifications may be present in 0-100% of the nucleotides—for example, more than 0%, 1%, 10%, 25%, 50%, 75%, 85%, 90%, 95%, or 100% of the constituent nucleotides individually or in combination.

Post-Synthesis Processing

Typically, a 5' cap and/or a 3' tail may be added after the synthesis. The presence of the cap is important in providing resistance to nucleases found in most eukaryotic cells. The presence of a "tail" serves to protect the mRNA from exonuclease degradation.

A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A, G(5')ppp(5')A and G(5')ppp(5')G. Additional cap structures are described in published US Application No. US 2016/0032356 and U.S. Provisional Application 62/464,327, filed Feb. 27, 2017, which are incorporated herein by reference.

Typically, a tail structure includes a poly(A) and/or poly (C) tail. A poly-A or poly-C tail on the 3' terminus of mRNA typically includes at least 50 adenosine or cytosine nucleotides, at least 150 adenosine or cytosine nucleotides, at least 200 adenosine or cytosine nucleotides, at least 250 adenosine or cytosine nucleotides, at least 300 adenosine or cytosine nucleotides, at least 350 adenosine or cytosine nucleotides, at least 400 adenosine or cytosine nucleotides, at least 450 adenosine or cytosine nucleotides, at least 500 adenosine or cytosine nucleotides, at least 550 adenosine or cytosine nucleotides, at least 600 adenosine or cytosine nucleotides, at least 650 adenosine or cytosine nucleotides, at least 700 adenosine or cytosine nucleotides, at least 750 adenosine or cytosine nucleotides, at least 800 adenosine or cytosine nucleotides, at least 850 adenosine or cytosine nucleotides, at least 900 adenosine or cytosine nucleotides, at least 950 adenosine or cytosine nucleotides, or at least 1 kb adenosine or cytosine nucleotides, respectively. In some embodiments, a poly A or poly C tail may be about 10 to 800 adenosine or cytosine nucleotides (e.g., about 10 to 200 adenosine or cytosine nucleotides, about 10 to 300 adenosine or cytosine nucleotides, about 10 to 400 adenosine or cytosine nucleotides, about 10 to 500 adenosine or cytosine nucleotides, about 10 to 550 adenosine or cytosine nucleotides, about 10 to 600 adenosine or cytosine nucleotides, about 50 to 600 adenosine or cytosine nucleotides, about 100 to 600 adenosine or cytosine nucleotides, about 150 to 600 adenosine or cytosine nucleotides, about 200 to 600 adenosine or cytosine nucleotides, about 250 to 600 adenosine or cytosine nucleotides, about 300 to 600 adenosine or cytosine nucleotides, about 350 to 600 adenosine or cytosine nucleotides, about 400 to 600 adenosine or cytosine nucleotides, about 450 to 600 adenosine or cytosine nucleotides, about 500 to 600 adenosine or cytosine nucleotides, about 10 to 150 adenosine or cytosine nucleotides, about 10 to 100 adenosine or cytosine nucleotides, about 20 to 70 adenosine or cytosine nucleotides, or about 20 to 60 adenosine or cytosine nucleotides) respectively. In some embodiments, a tail structure includes is a combination of poly (A) and poly (C) tails with various lengths described herein. In some embodiments, a tail structure includes at least 50%, 55%, 65%, 70%, 75%, 80%, 85%, 90%, 92%, 94%, 95%, 96%, 97%, 98%, or 99% adenosine nucleotides. In some embodiments, a tail structure includes at least 50%, 55%, 65%, 70%, 75%, 80%, 85%, 90%, 92%, 94%, 95%, 96%, 97%, 98%, or 99% cytosine nucleotides.

As described herein, the addition of the 5' cap and/or the 3' tail facilitates the detection of abortive transcripts generated during in vitro synthesis because without capping and/or tailing, the size of those prematurely aborted mRNA transcripts can be too small to be detected. Thus, in some embodiments, the 5' cap and/or the 3' tail are added to the synthesized mRNA before the mRNA is tested for purity (e.g., the level of abortive transcripts present in the mRNA). In some embodiments, the 5' cap and/or the 3' tail are added to the synthesized mRNA before the mRNA is purified as described herein. In other embodiments, the 5' cap and/or the 3' tail are added to the synthesized mRNA after the mRNA is purified as described herein.

Delivery Vehicles

According to the present invention, mRNA encoding an anti-C3b antibody or antigen binding fragment as described herein may be delivered as naked RNA (unpackaged) or via delivery vehicles. As used herein, the terms "delivery vehicle," "transfer vehicle," "nanoparticle" or grammatical equivalent, are used interchangeably.

Delivery vehicles can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition. A particular delivery vehicle is selected based upon its ability to facilitate the transfection of a nucleic acid to a target cell.

Liposomal Delivery Vehicles

In some embodiments, a suitable delivery vehicle is a liposomal delivery vehicle, e.g., a lipid nanoparticle (LNP). As used herein, liposomal delivery vehicles, e.g., lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.). In the context of the present invention, a liposomal delivery vehicle typically serves to transport a desired mRNA to a target cell or tissue. In some embodiments, a nanoparticle delivery vehicle is a liposome. In some embodiments, a liposome comprises one or more cationic lipids, one or more non-cationic lipids, one or more cholesterol-based lipids and one or more PEG-modified lipids.

Therapeutic Use of Compositions

In one aspect, the present invention, among other things, provide a method of inducing anti-C3b antibody expression in vivo by administration of nucleic acids encoding an anti-C3b antibody or a fragment thereof, or by administration of an anti-C3b antibody. In some embodiments, a composition comprises nucleic acids encapsulated or complexed with a delivery vehicle. In some embodiments, the delivery vehicle is selected from the group consisting of liposomes, lipid nanoparticles, solid-lipid nanoparticles, polymers, viruses, sol-gels, and nanogels. In some embodiments, nucleic acids encoding an anti-C3b antibody or a fragment thereof are packaged in a viral particle.

Gene Therapy

In some embodiments, a pharmaceutical composition comprising nucleic acids encoding an anti-C3b antibody or a fragment thereof is used to treat subjects in need thereof. In some embodiments, a pharmaceutical composition comprising a rAAV vector described herein is used to treat subjects in need thereof. The pharmaceutical composition containing a rAAV vector or particle of the invention contains a pharmaceutically acceptable excipient, diluent or carrier. Examples of suitable pharmaceutical carriers are well known in the art and include phosphate buffered saline solutions, water, emulsions, such as oil/water emulsions, various types of wetting agents, sterile solutions and the like. The pharmaceutical composition can be in a lyophilized form. Such carriers can be formulated by conventional methods and are administered to the subject at a therapeutically effective amount.

The rAAV vector is administered to a subject in need thereof via a suitable route. In some embodiments, the rAAV vector is administered by intravenous, intraperitoneal, subcutaneous, or intradermal routes. In one embodiment, the rAAV vector is administered intravenously. In embodiments, the intradermal administration comprises administration by use of a "gene gun" or biolistic particle delivery system. In some embodiments, the rAAV vector is administered via a non-viral lipid nanoparticle. For example, a composition comprising the rAAV vector may comprise one or more diluents, buffers, liposomes, a lipid, a lipid complex. In some embodiments, the rAAV vector is comprised within a microsphere or a nanoparticle, such as a lipid nanoparticle or an inorganic nanoparticle.

In some embodiments, a rAAV is pseudotyped. A pseudotyped rAAV is an infectious virus comprising any combination of an AAV capsid protein and a rAAV genome. Pseudotyped rAAV are useful to alter the tissue or cell specificity of rAAV, and may be employed alone or in conjunction with non-pseudotyped rAAV to transfer one or more genes to a cell, e.g., a mammalian cell. For example, pseudotyped rAAV may be employed subsequent to administration with non-pseudotyped rAAV in a mammal which has developed an immune response to the non-pseudotyped rAAV. Capsid proteins from any AAV serotype may be employed with a rAAV genome which is derived or obtainable from a wild-type AAV genome of a different serotype or which is a chimeric genome, i.e., formed from AAV DNA from two or more different serotypes, e.g., a chimeric genome having 2 ITRs, each ITR from a different serotype or chimeric ITRs. The use of chimeric genomes such as those comprising ITRs from two AAV serotypes or chimeric ITRs can result in directional recombination which may further enhance the production of transcriptionally active intermolecular concatamers. Thus, the 5' and 3' ITRs within a rAAV vector of the invention may be homologous, i.e., from the same serotype, heterologous, i.e., from different serotypes, or chimeric, i.e., an ITR which has ITR sequences from more than one AAV serotype.

In some embodiments, the rAAV vector is an AAV1, AAV2, AAV3, AAV4, AAV5, AAV6, AAV7, AAV8, AAV9, AAV10, or AAV11 vector. In some embodiments, the rAAV vector is AAV1. In some embodiments, the rAAV vector is AAV2. In some embodiments, the rAAV vector is AAV3. In some embodiments, the rAAV vector is AAV4. In some embodiments, the rAAV vector is AAV5. In some embodiments, the rAAV vector is AAV6. In some embodiments, the rAAV vector is AAV7. In some embodiments, the rAAV vector is AAV8. In some embodiments, the rAAV vector is AAV9. In some embodiments, the rAAV vector is AAV10. In some embodiments, the rAAV vector is AAV11. In some embodiments, the rAAV vector is sequence optimized. In some embodiments, the rAAV capsid is modified. For example, in some embodiments, the rAAV8 capsid is modified.

Treatment with C3b Antagonists or Anti-C3b Antibodies

In some embodiments, the present invention provides, among other things, a method of treating complement mediated disorders (e.g., C3 glomerulopathy) by administering a C3b antagonist or an anti-C3b antibody. In some embodiments, the present invention provides, among other things, a method of treating complement medicated disorder in a subject comprising administering to the subject a C3b antagonist or an anti-C3b antibody at a therapeutically effective dose and an administration interval for a treatment period sufficient to improve, stabilize or reduce one or more symptoms of the said disorder. In some embodiments, the present invention provides, among other things, a method of treating complement medicated disorder in a subject comprising administering to the subject a composition comprising a nucleic acid encoding a C3b antagonist or an anti-C3b antibody at a therapeutically effective dose and an administration interval for a treatment period sufficient to improve, stabilize or reduce one or more symptoms of the said disorder. In some embodiments, the present invention provides, among other things, a method of treating complement medicated disorder in a subject comprising administering to the subject a composition comprising mRNA encoding a C3b antagonist or an anti-C3b antibody at a therapeutically effective dose and an administration interval for a treatment period sufficient to improve, stabilize or reduce one or more symptoms of the said disorder.

Complement Mediated Disorders

Many autoimmune diseases are characterized by generation of autoantibodies that bind to host proteins or deposit within tissues as a component of immune complexes. The autoantibodies can activate the complement system, which can mediate tissue damage and trigger systemic inflammation. Complement inhibitory drugs may, therefore, be beneficial across a large number of different autoimmune diseases.

C3 glomerulopathy (C3G) is a rare disease that is characterized by accumulation of complement factors in the glomeruli due to overactivation and abnormal regulation of the alternative pathway (AP) of complement. It is an ultra-rare disease with an incidence of approximately 1-3 per million per year. C3 glomerulopathy is an umbrella term for a spectrum of related diseases or disorders characterized by accumulation of the C3 component of complement in renal tissue. Abnormal control of the AP of complement may be due to acquired or genetic abnormalities of the complement regulatory proteins. The deposition of complement factors drives glomerular inflammation, resulting in a proliferative glomerulonephritis. The most common diseases under the C3G umbrella are C3 Glomerulonephritis (C3GN), characterized by mesangial, subendothelial, and intramembranous deposits, and Dense Deposit Disease (DDD), characterized by dense deposits along the glomerular and tubular basement membranes. Presentation of disease ranges from asymptomatic hematuria and proteinuria to an acute presentation with the classic signs and symptoms of glomerulonephritis. C3 glomerulopathy is driven by acquired factors (anti-C3 and C5 convertase autoantibodies) and genetic mutations in complement-related genes. These autoantibodies drive complement dysregulation by increasing the half-life of these vital but normally short-lived enzymes. Genetic mutations in Factor H, Complement Factor H related (CFHR) proteins, C3 can lead to impaired regulation of C3 convertase.

Other diseases associated with AP overactivation includes Paroxysmal Nocturnal Hemoglobinuria with extravascular hemolysis, which is a rare, acquired, blood disorder where RBCs are targeted by C3b rather than MAC. In patients with Paroxysmal Nocturnal Hemoglobinuria, C5 inhibitors do not work and it remains a major unmet medical need. Geographic Atrophy (GA) is another complication that is associated with AP overactivation. Geographic atrophy is an advanced manifestation of Age-related Macular Degeneration (AMD) characterized by progressive and irreversible loss of the retinal pigment epithelium and photoreceptors, a major cause of legal blindness. 98% of wet AMD patients develop GA despite anti-VEGF treatment.

In one aspect, the present invention provides a method of treating a disease or disorder, said method comprises administering a therapeutically effective amount of an anti-C3b antibody or a fragment thereof to a subject in need thereof. In some embodiments, the disease or disorder is complement mediated disorder. In some embodiments, the disease or disorder is C3 glomerulopathy. In some embodiments, the disease or disorder is associated with C3 glomerulopathy. In some embodiments, the disease or disorder is dense deposit disease. In some embodiments, the disease or disorder is C3 glomerulonephritis (C3GN). In some embodiments, the disease or disorder is disorder is characterized by accumulation of the C3 component of complement in renal tissue. In some embodiments, the disease or disorder is hematuria. In some embodiments, the disease or disorder is proteinuria. In some embodiments, the disease or disorder is Acute Kidney Injury (AKI). In some embodiments, the disease or disorder is Chronic Kidney Disease (CKD). In some embodiments, the disease or disorder is associated with AP overactivation. In some embodiments, the disease or disorder is Paroxysmal Nocturnal Hemoglobinuria. In some embodiments, the disease or disorder is Geographic Atrophy (GA). In some embodiments, the disease or disorder is autoimmune hemolytic anemia (AIHA). In some embodiments, the disease or disorder is Age-related Macular Degeneration (AMD). In some embodiments, the disease or disorder is wet Age-related Macular Degeneration (wAMD). In some embodiments, the disease or disorder is Passive Heymann Nephritis (PHN). In some embodiments, the disease or disorder is rheumatoid arthritis (RA). In some embodiments, the disease or disorder is collagen-antibody induced arthritis (CAIA). In some embodiments, the disease or disorder is caused by genetic mutation in Factor H. In some embodiments, the disease or disorder is caused by genetic mutation in CFHR proteins. In some embodiments, the disease or disorder is caused by genetic mutation in C43. In some embodiments, the disease is driven by acquired factors. In some embodiments, the acquired factors are anti-C3 autoantibodies. In some embodiments, the acquired factors are C5 convertase autoantibodies.

Effects of Anti-C3b Antibodies

In some embodiments, the administering of the anti-C3b antibody or a fragment thereof inhibits C3 deposition in the subject. In some embodiments, the administrating the anti-C3b antibody or a fragment thereof inhibits C3 activity or C3 activation.

In some embodiments, the administrating of the anti-C3b antibody or a fragment thereof inhibits alternative pathway (AP). In some embodiments, the administering of the anti-C3b antibody or a fragment thereof inhibits classical pathway (CP). In some embodiments, the administering of the anti-C3b antibody or a fragment thereof inhibits both alternative pathway (AP) and classical pathway (CP). In some embodiments, the administering of the anti-C3b antibody or a fragment thereof inhibits alternative pathway (AP) but does not inhibit classical pathway (CP). In some embodiments, the level of AP inhibition is higher than the level of CP inhibition. In some embodiments, the level of AP inhibition is about or more than 2-fold greater than the level of CP inhibition. In some embodiments, the level of AP inhibition is about or more than 3-fold greater than the level of CP inhibition. In some embodiments, the level of AP inhibition is about or more than 4-fold greater than the level of CP inhibition. In some embodiments, the level of AP inhibition is about or more than 5-fold greater than the level of CP inhibition. In some embodiments, the level of AP inhibition is about or more than 8-fold greater than the level of CP inhibition. In some embodiments, the level of AP inhibition is about or more than 10-fold greater than the level of CP inhibition.

In some embodiments, the administering of the anti-C3b antibody or a fragment thereof inhibits Complement Factor B binding to C3b. In some embodiments, the administering of the anti-C3b antibody or a fragment thereof inhibits Factor B binding to C3b by about 10% as compared to baseline. In some embodiments, the administering of the anti-C3b antibody or a fragment thereof inhibits Factor B binding to C3b by about 15% as compared to baseline. In some embodiments, the administering of the anti-C3b antibody or a fragment thereof inhibits Factor B binding to C3b by about 20% as compared to baseline. In some embodiments, the administering of the anti-C3b antibody or a fragment thereof inhibits Factor B binding to C3b by about 25% as compared to baseline. In some embodiments, the administering of the anti-C3b antibody or a fragment thereof inhibits Factor B binding to C3b by about 30% as compared to baseline. In some embodiments, the administering of the anti-C3b antibody or a fragment thereof inhibits Factor B binding to C3b by about 40% as compared to baseline. In some embodiments, the administering of the anti-C3b antibody or a fragment thereof inhibits Factor B binding to C3b by about 45% as compared to baseline. In some embodiments, the administering of the anti-C3b antibody or a fragment thereof inhibits Factor B binding to C3b by about 50% as compared to baseline. In some embodiments, the administering of the anti-C3b antibody or a fragment thereof inhibits Factor B binding to C3b by about 60% as compared to baseline. In some embodiments, the administering of the anti-C3b antibody or a fragment thereof inhibits Factor B binding to C3b by about 70% as compared to baseline. In some embodiments, the administering of the anti-C3b antibody or a fragment thereof inhibits Factor B binding to C3b by about 80% as compared to baseline. In some embodiments, the administering of the anti-C3b antibody or a fragment thereof inhibits Factor B binding to C3b by about 85% as compared to baseline. In some embodiments, the administering of the anti-C3b antibody or a fragment thereof inhibits Factor B binding to C3b by about 90% as compared to baseline. In some embodiments, the administering of the anti-C3b antibody or a fragment thereof inhibits Factor B binding to C3b by about 95% as compared to baseline. In some embodiments, the administering of the anti-C3b antibody or a fragment thereof inhibits Factor B binding to C3b by about 99% as compared to baseline. In some embodiments, the administering of the anti-C3b antibody or a fragment thereof completely inhibits Factor B binding to C3b. In some embodiments, the administering of the anti-C3b antibody or a fragment thereof partially inhibits Factor B binding to C3b.

In some embodiments, the administering of the anti-C3b antibody or a fragment thereof inhibits Factor P binding to C3bBb. In some embodiments, the administering of the anti-C3b antibody or a fragment thereof inhibits Factor P binding to C3bBb by about 10% as compared to baseline. In some embodiments, the administering of the anti-C3b antibody or a fragment thereof inhibits Factor P binding to C3bBb by about 15% as compared to baseline. In some embodiments, the administering of the anti-C3b antibody or a fragment thereof inhibits Factor P binding to C3bBb by about 20% as compared to baseline. In some embodiments, the administering of the anti-C3b antibody or a fragment thereof inhibits Factor P binding to C3bBb by about 25% as compared to baseline. In some embodiments, the administering of the anti-C3b antibody or a fragment thereof inhibits Factor P binding to C3bBb by about 30% as compared to baseline. In some embodiments, the administering of the anti-C3b antibody or a fragment thereof inhibits Factor P binding to C3bBb by about 40% as compared to baseline. In some embodiments, the administering of the anti-C3b antibody or a fragment thereof inhibits Factor P binding to C3bBb by about 45% as compared to baseline. In some embodiments, the administering of the anti-C3b antibody or a fragment thereof inhibits Factor P binding to C3b by about 50% as compared to baseline. In some embodiments, the administering of the anti-C3b antibody or a fragment thereof inhibits Factor P binding to C3bBb by about 60% as compared to baseline. In some embodiments, the administering of the anti-C3b antibody or a fragment thereof inhibits Factor P binding to C3bBb by about 70% as compared to baseline. In some embodiments, the administering of the anti-C3b antibody or a fragment thereof inhibits Factor P binding to C3bBb by about 80% as compared to baseline. In some embodiments, the administering of the anti-C3b antibody or a fragment thereof inhibits Factor P binding to C3bBb by about 85% as compared to baseline. In some embodiments, the administering of the anti-C3b antibody or a fragment thereof inhibits Factor P binding to C3bBb by about 90% as compared to baseline. In some embodiments, the administering of the anti-C3b antibody or a fragment thereof inhibits Factor P binding to C3bBb by about 95% as compared to baseline. In some embodiments, the administering of the anti-C3b antibody or a fragment thereof inhibits Factor P binding to C3bBb by about 99% as compared to baseline. In some embodiments, the administering of the anti-C3b antibody or a fragment thereof completely inhibits Factor P binding to C3bBb. In some embodiments, the administering of the anti-C3b antibody or a fragment thereof partially inhibits Factor P binding to C3bBb.

Pharmaceutical Compositions and Administration

The antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, intravitreal, and rectal administration. Solutions or suspensions used for parenteral, intradermal, or subcutaneous application can include the following components: a sterile diluent such as sterile water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled-release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Dosing Methods

In certain embodiments, an anti-C3b antibody is administered by any route suitable for the administration of an anti-C3b antibody, such as, for example, intravenous, or subcutaneous.

In some embodiments, a single administration of an anti-C3b antibody is sufficient to improve, stabilize or reduce one or more symptoms for longer than five-days, 1-week, 2-weeks, 4-weeks, 5-weeks, 7-weeks, 12-weeks or more.

In some embodiments a single administration of an anti-C3b antibody is sufficient to improve, stabilize or reduce one or more symptoms so that the subject does not require a repeat dose.

The therapeutically effective amount of an anti-C3b antibody containing pharmaceutical composition to be employed will depend, for example, upon the therapeutic context and objectives. One skilled in the art will appreciate that the appropriate dosage levels for treatment will vary depending, in part, upon the molecule delivered, the indication for which the anti-C3b antibody is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 μg/kg to up to about 1000 mg/kg or more, depending on the factors mentioned above.

In some embodiments, the therapeutic effective dose is between about 1 mg and 1000 mg. In some embodiments, the therapeutic effective dose is between about 10 mg and 500 mg.

EXAMPLES

While certain compounds, compositions and methods of the present invention have been described with specificity in accordance with certain embodiments, the following examples serve only to illustrate the invention and are not intended to limit the same. While certain compounds, compositions and methods of the present invention have been described with specificity in accordance with certain embodiments, the following examples serve only to illustrate the invention and are not intended to limit the same.

Example 1. Pharmacokinetic Analysis of Anti-C3b Antibody

In this study, pharmacokinetics of anti-C3b antibodies was determined in non-human primates. First, Ab1 (anti-C3b VHH fused to modified IgG4 Fc) and control Ab (IC12; control antibody) were intravenously administered at 10 mg/kg to Cynomolgus monkeys. The characteristics of each antibody is shown in Table 1. Plasma samples were collected pre-administration and at 30 minutes, 6 hr, 24 hr, 48 hr, 120 hr, 336 hr, 456 hr, 672 hr, and 792 hr post administration, and % of antibody remaining was measured.

TABLE 1

Description of antibodies used in Pharmacokinetics

| Antibody | Description |
|---|---|
| Ab1 | Anti-C3b VHH fused to modified IgG4 Fc (SEQ ID NO: 6) |
| Control Ab | IC12 (Commercially available antibody; anti-West Nile Virus NS1 antibody) |

Figure 1B:
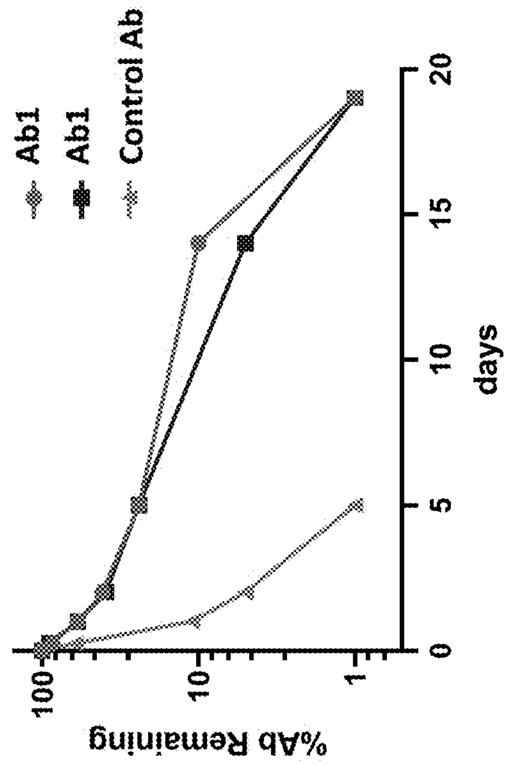

FIG. 1A shows the levels of Ab1 (in duplicates) and the control Ab in plasma levels over 20-days. It was observed that Ab1 persisted in sera for more than 15 days. FIG. 1B shows the percentage of Ab1 (in duplicates) and the control Ab in plasma levels over 20-days. The data shows that significantly higher % of antibody was remaining over time for Ab1, as compared to the control Ab.

Figure 1C:
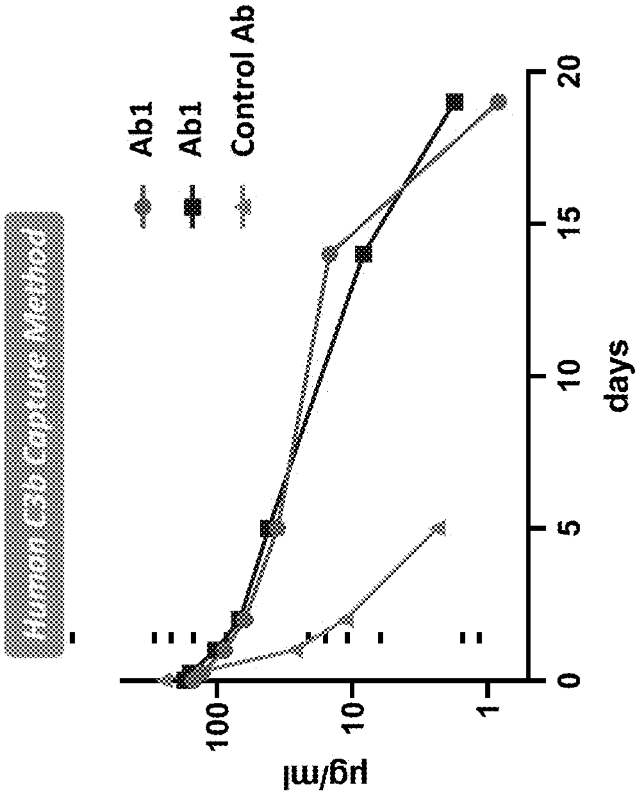
FIG. 1C and FIG. 1D are exemplary graphs showing the C3b antibody levels by capture of human and Cynomolgus C3b, respectively.
Figure 1D:
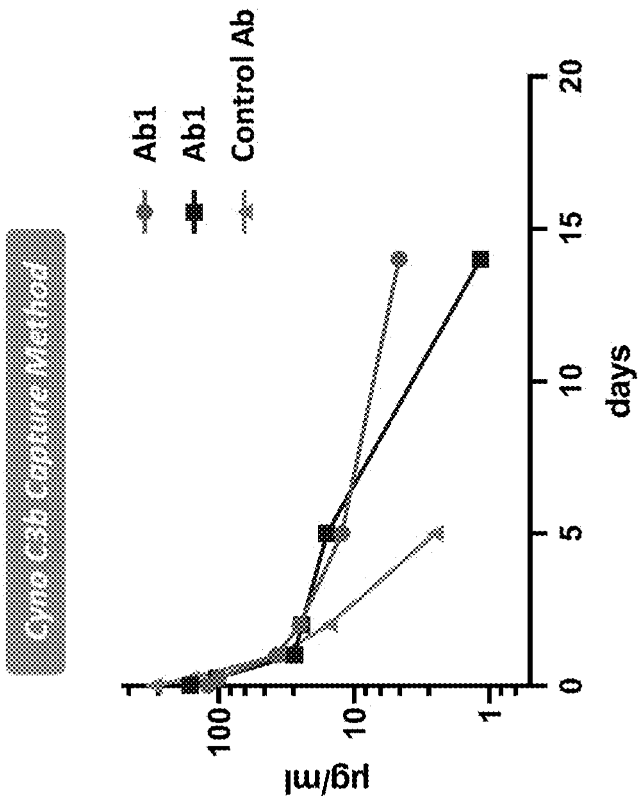

To confirm that the C3b antibody of the present invention binds to human C3b with high affinity, in addition to Cynomolgus C3b, concentrations of antibodies to human C3b or Cynomolgus C3b were measured. As shown in FIG. 1C and FIG. 1D, Ab1 binds to human C3b with high affinity, about 100-fold greater affinity as compared to Cynomolgus C3b.

Figure 1E:
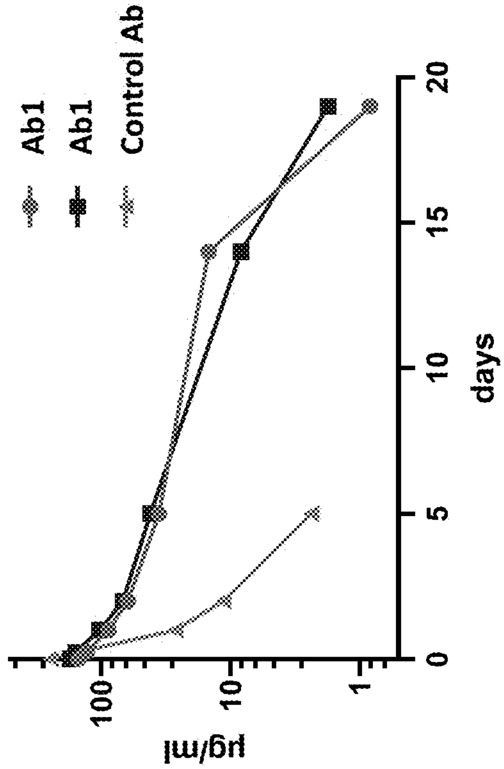
FIG. 1E is an exemplary graph showing the plasma antibody levels in ex vivo C3 deposition assay.
Figure 1F:
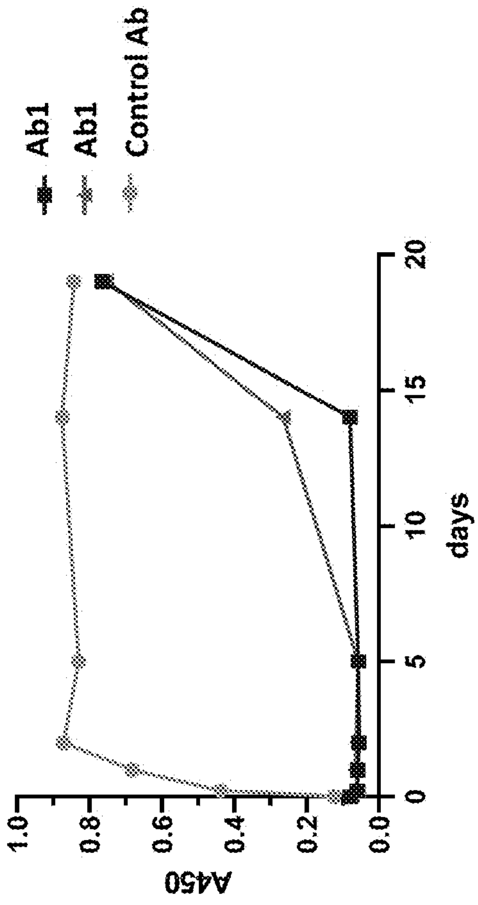
FIG. 1F is an exemplary graph showing the inhibition of C3 deposition as measured by absorbance at 450 nm.

Next, the pharmacodynamics effect of the anti-C3b Ab1 and the control Ab was evaluated. The ex vivo C3 deposition studies were done at 3% serum concentrations, and inhibition of C3 deposition was measured over time. FIG. 1E shows plasma antibody levels, and FIG. 1F shows the inhibition of C3 deposition. Under these conditions, PD effect observed for Ab1 was for more than 14 days. Additionally, the PK/PD of control Ab shows importance of inhibition of C3(H2O) mediated tick-over mechanism on target-mediated drug disposition (TMDD).

Example 2. C3 Convertase Inhibition in Wet Age-Related Macular Degeneration (AMD) by C3b Antibody Wet age-related macular degeneration (wAMD) is the less common but most severe form of AMD and one of the leading cause of blindness in the elderly. wAMD is characterized by choroidal neovascularization (CMV) and acute vision loss. The retina is particularly vulnerable to oxidative damage that trigger complement activation and tissue development of AMD. Current treatment comprises monthly intravitreal injections of anti-VEGF antibodies.

This example illustrates an efficacy of C3b antibody of the present invention in wAMD, using the mouse laser-induced choroidal neovascularization (CNV) model. wAMD-like disease is triggered in the mouse by laser-induced injury to the retina basal membrane (Bruch's membrane) placed at 4 spots around the optical nerve. The injury triggers neovascularization from the underlying capillary layer (choroid) into the retina, leading to inflammatory response.

TABLE 2

Study of different Antibodies in CNV model

| Animal Groups | Description/SEQ ID |
|---|---|
| Vehicle Control | Negative control |
| Eylea (positive control) | Positive control (commercially available VEGF inhibitor) |
| Ab2 | Anti-C3b VHH fused to IgG4 Fc with S228P (SEQ ID NO: 8) |
| Ab3 | Anti-C3b VHH fused to IgG4 Fc with S228P SEQ ID NO: 9 |

Figure 2:
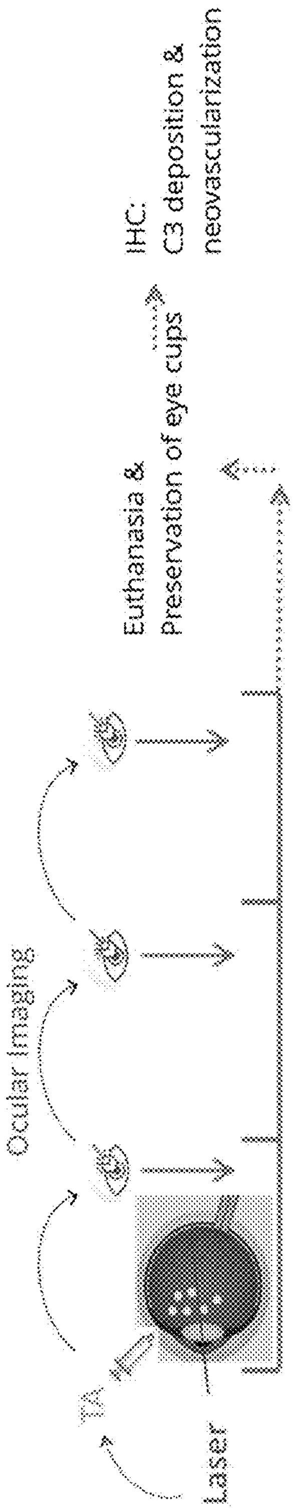
FIG. 2 is an exemplary schematic of study design for assessing efficacy of anti-C3b antibody in mouse laser-induced choroidal neovascularization (CNV) model.

Mice were administered intravitreally with the vehicle or antibodies as shown in Table 2, and ocular imaging was performed on day 0, 1, 3, and 7 according to study design show in FIG. 2. Particularly, two ocular imaging techniques were used in this example. First, by en-face imaging by fluorescein angiography (FA), which uses sodium fluorescein to visualize the ocular vasculature. The extent of CNV is determined by vasculopathy-based scoring system as shown below, and by the size of CNV en-face area. Secondly, ocular imaging is performed by cross-sectional imaging by optical coherence tomography (OTC). The extent of CNV is determined by the size of CNV cross-sectional area.

FA Vasculopathy Scoring System

| Score | Descriptor |
|---|---|
| 1 | No Hyperfluorescence |
| 2 | Hyperfluorescence without leakage |
| 3 | Hyperfluorescence early or mid-transit with late leakage |
| 4 | Hyperfluorescence early or mid-transit with late leakage extending beyond the borders of treated area |

Figure 3A:
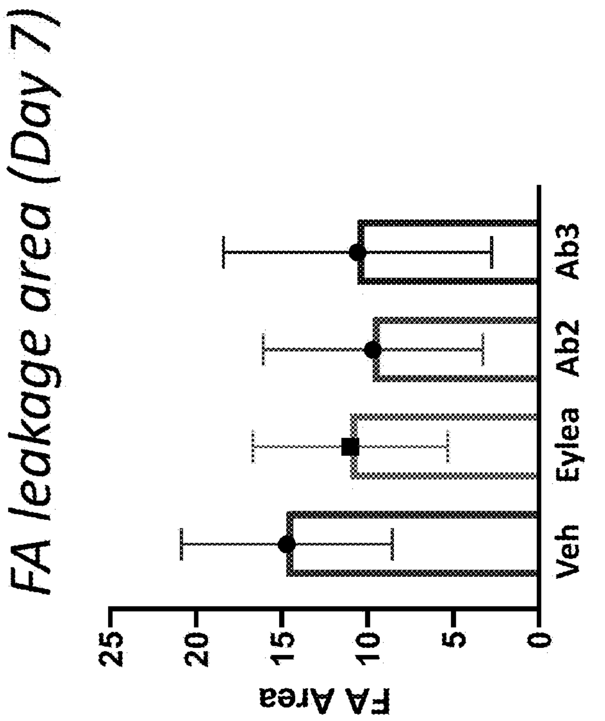
FIGS. 3A and 3B are exemplary graphs showing the effect of C3b antibodies on wAMD.
Figure 3B:
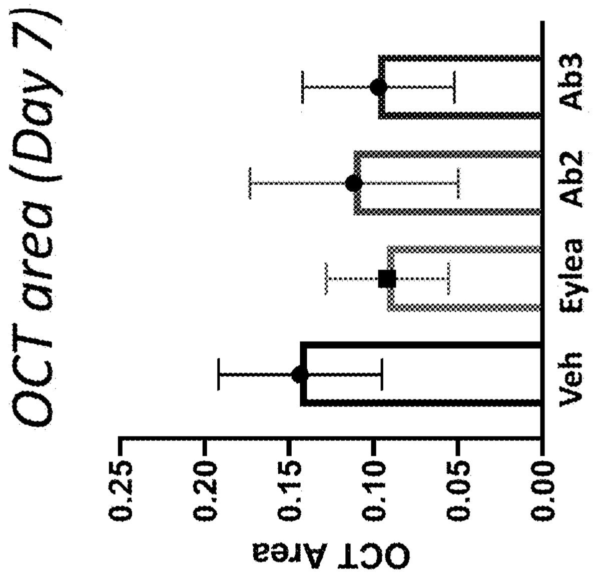

FIG. 3A shows FA leakage area after treatment with each antibody at day 7. FIG. 3B shows the OCT area after treatment with each antibody at day 7. Table 3 shows the percent reduction in OCT area and FA leakage relative to vehicle control. Data shows that both Ab2 and Ab3 provided at least ~30% protection at day 7 in mice. The alternative pathway is only partially responsible for CNV pathology (~35%). Therefore, the 30% reduction in disease suggests that the C3b antibodies of the present invention were highly effective in blocking in AP's contribution to disease progression.

TABLE 3

| Percent reduction relative to control on day 7<br>% Reduction Relative to Vehicle Control (Day 7) | | |
|---|---|---|
| Treatment | FA Area | OCT Area |
| Eylea | −25% | −36% |
| Ab2 | −34% | −22% |
| Ab3 | −28% | −32% |

Example 3. Efficacy of C3b Antibodies on Passive Heymann Nephritis (PHN)

Passive Heymann Nephritis (PHN) mimics human idiotypic membrane nephritis (iMN), which is triggered by autoantibodies to the podocyte antigen PLA2-R. PHN is triggered in rats by a nephrotoxin serum (Fx1A) targeting megalin, a nephritic protein found on the surfaces of podocytes and proximal tubules.

Figure 4:
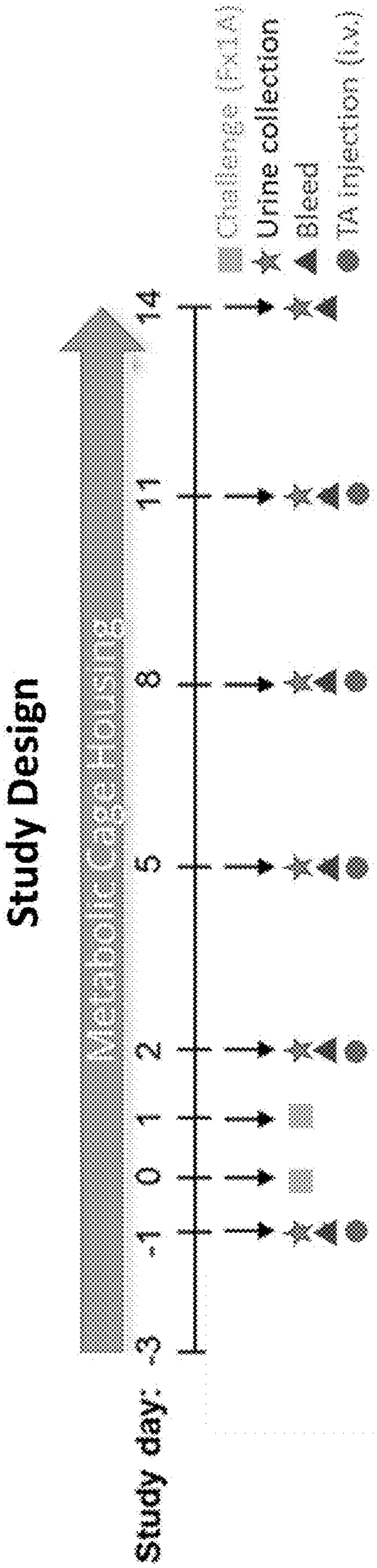
FIG. 4 is an exemplary schematic of study design for assessing efficacy of anti-C3b antibody in PHN.

This experiment evaluated the use of C3b antibodies in PHN mouse models. The study design for this experiment is shown in FIG. 4. The PHN phenotypes were induced in PHN model mice by induction with nephrotoxin serum (Fx1A) targeting megalin. PHN-mice were treated with antibodies as shown in Table 4 on day 2 and were treated twice weekly, by intravenous administration. Serum and urinary biomarkers, and kidney histology were evaluated to assess the efficacy of treated groups.

TABLE 4

| Treatment groups in PHN Study | | |
|---|---|---|
| Animal Groups | Treatment | Dose |
| 1 | No disease control | |
| 2 | Anti-Fx1A<br>(negative control) | |
| 3 | Cobra Venom Factor<br>(Positive control) | |
| 4 | Ab2 | 10 mg/kg |
| 5 | Ab2 | 50 mg/kg |

Figure 5A:
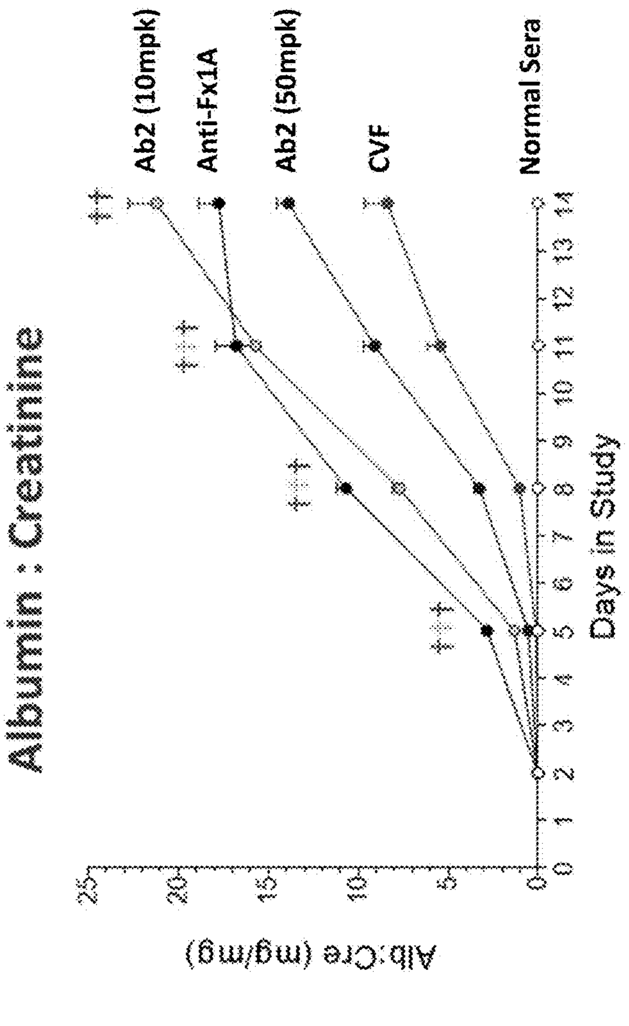
FIG. 5A is an exemplary graph showing the Albumin: Creatinine ratios as urinary biomarkers for measuring effect of subject C3b antibodies on PHN.
Figure 5B:
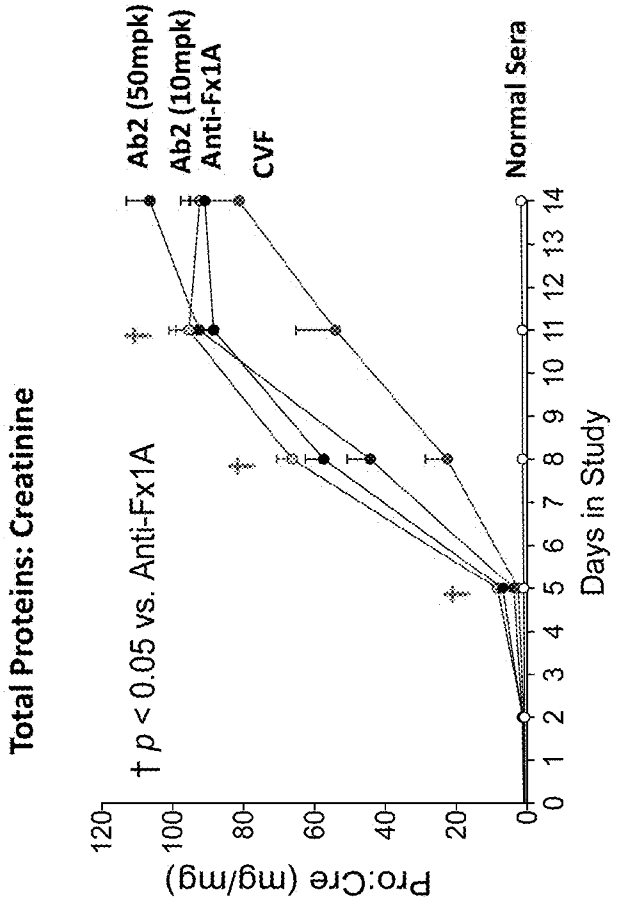
FIG. 5B is an exemplary graph showing the total protein:creatinine level as urinary biomarkers for measuring effect of subject C3b antibodies on PHN.

FIG. 5A shows the Albumin to creatinine ratio (urinary biomarker) in the PHN mouse models treated with Ab2 at different dosages as compared to mice treated with positive and negative controls. It was observed that treatment with 50 mg/kg of Ab2 resulted in significantly low albumin to creatinine ratio. Next, the total protein to creatinine ratio was determined as shown in FIG. 5B.

Figure 6A:
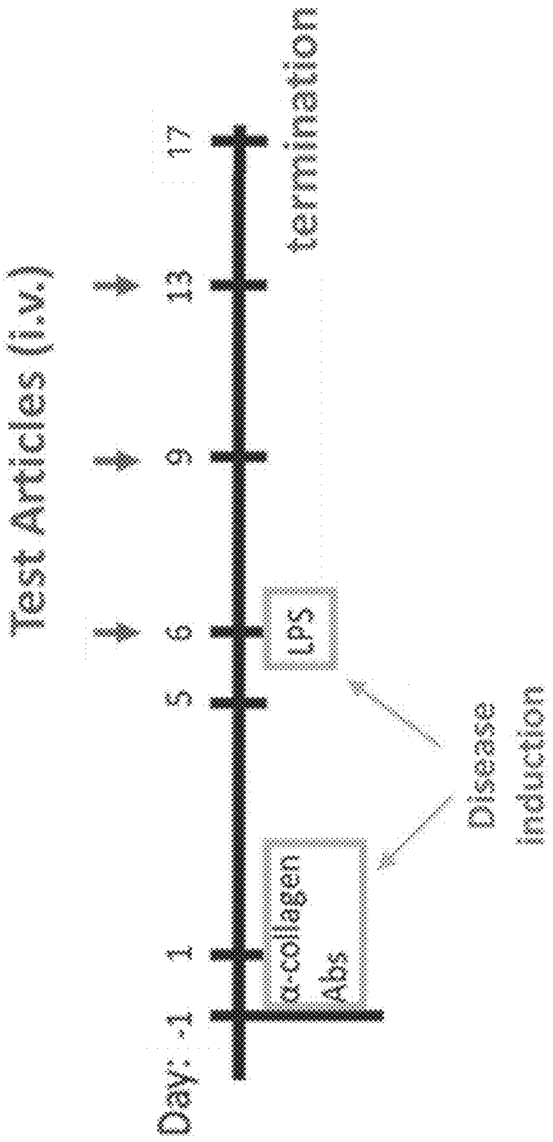
FIG. 6A is an exemplary study design schematic for testing efficacy of C3b antibody in treatment of collagen-antibody induced arthritis mouse model.
Figure 6B:
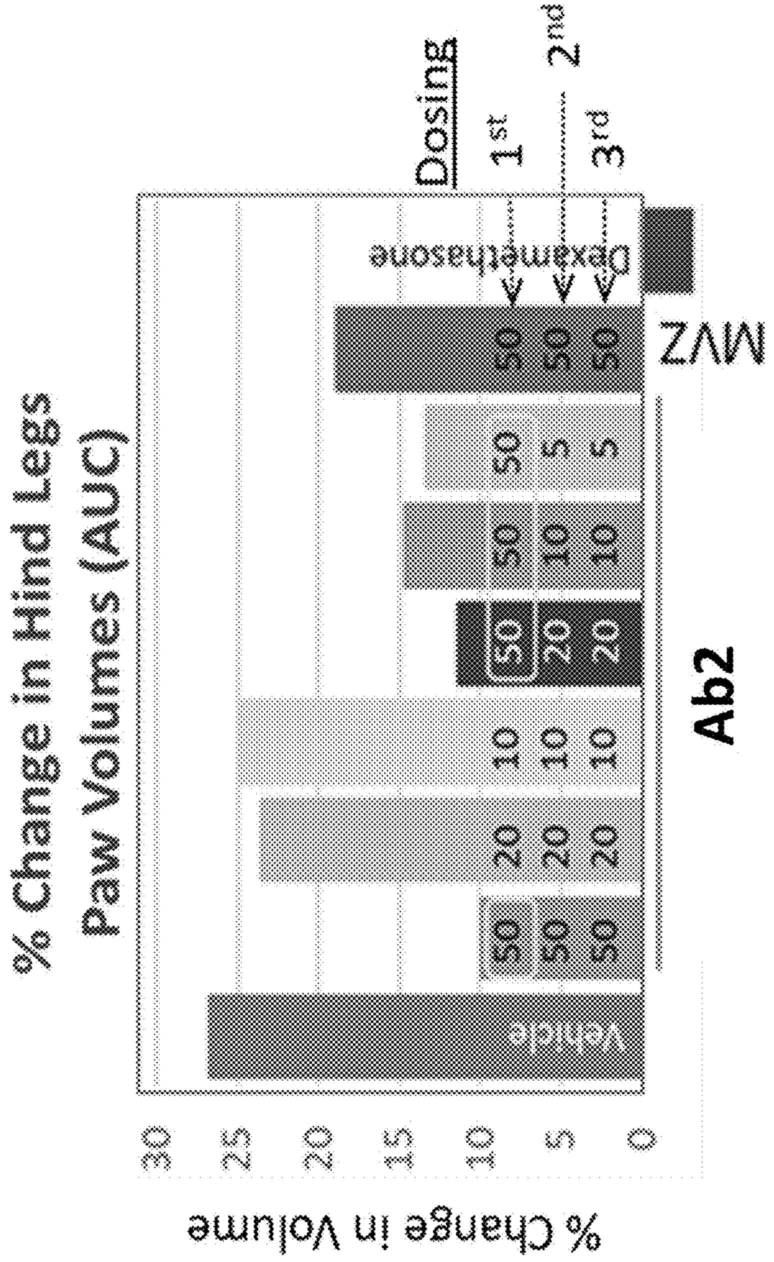
FIG. 6B is an exemplary graph showing the percent change in hind leg paw volumes at different dosages of C3b antibodies as compares to positive and negative controls.

Example 4. Efficacy of C3b Antibodies on Collagen-Antibody Induced Arthritis (CAIA) Mouse Model of RA This experiment evaluated the use of C3b antibodies in Collagen Type II-Specific Monoclonal Antibody-Induced Arthritis (CAIA). The schematic for study design is shown in FIG. 6A. Anti-C3b VHH fused to Fc (Ab2) was administered at various concentrations, on day 6, 9, and 13. MVZ antibody was used as a positive control, and dexamethasone was used as a negative control. FIG. 6B shows the dose dependent reduction of paw volumes of mice in response to treatment with Ab2. Based on data, it appears that protection correlates mainly with the first dose given on day 6 of the study.

Example 5. Efficacy of C3b Antibodies on C3 Convertase Activity in C3G Patients

Figure 7:
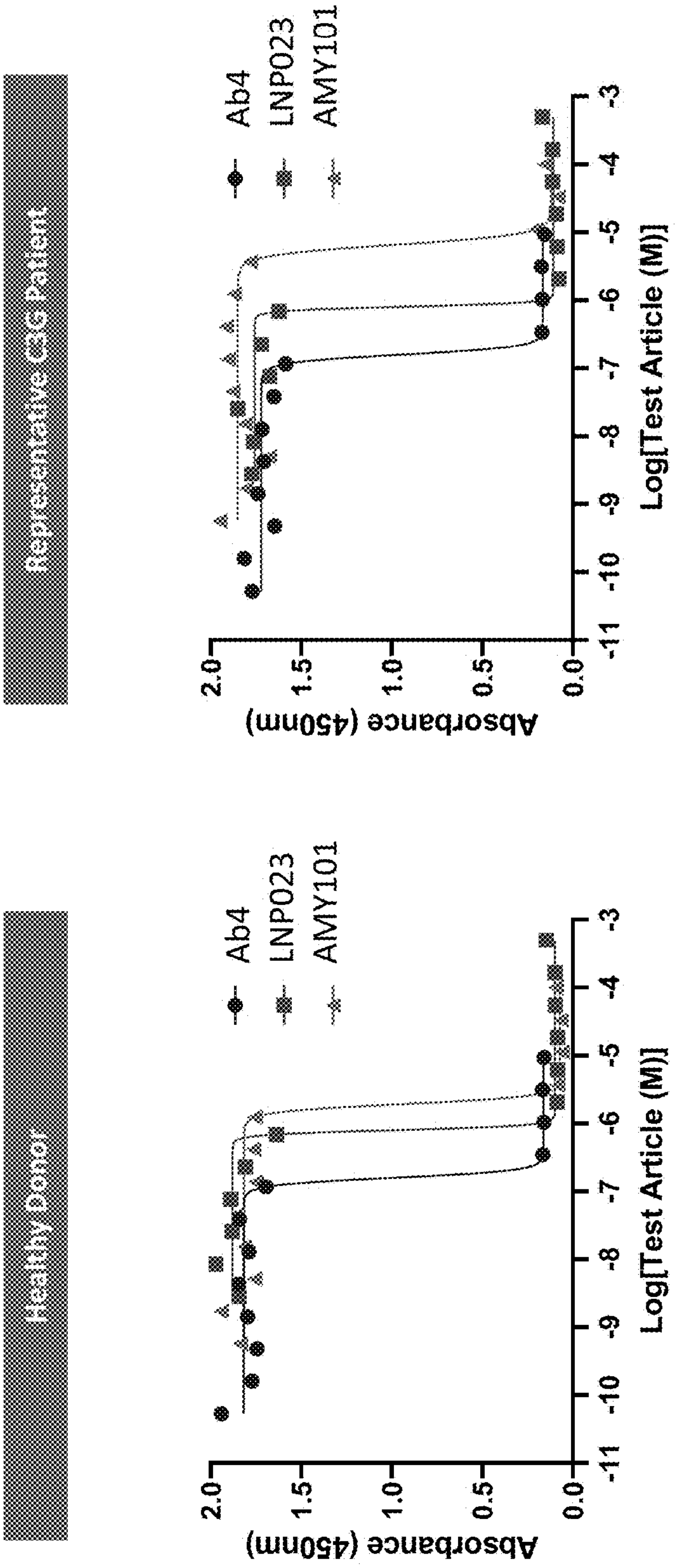
FIG. 7 is an exemplary graph showing inhibition of C3 convertase by Ab4, AMY-101, and LNP023, measured by C3 deposition assay, in the healthy donor and representative C3G patients.

This experiment evaluated the efficacy of C3b antibodies in inhibiting C3 convertase activity in sera of human Complement 3 Glomerulopathy (C3G) patients. C3G patient samples were collected and ex vivo C3 convertase inhibition was measured by C3 deposition assay according to methods known in the art. AMY-101 (a C3 inhibitor) and LNP023 were used as controls. The anti-C3b antibody used in this particular assay was Ab4, which comprises VHH of SEQ ID NO: 13 fused to the Fc domain of SEQ ID NO: 14. As shown in FIG. 7, Ab4 was particularly effective in inhibiting C3 deposition as compared to the controls.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

SEQUENCE LISTING

```
Sequence total quantity: 27
SEQ ID NO: 1           moltype =   length =
SEQUENCE: 1
000

SEQ ID NO: 2           moltype =   length =
SEQUENCE: 2
000

SEQ ID NO: 3           moltype =   length =
SEQUENCE: 3
000

SEQ ID NO: 4           moltype = AA  length = 353
FEATURE                Location/Qualifiers
source                 1..353
                       mol_type = protein
                       organism = synthetic construct
SEQUENCE: 4
EVQLLESGGG LVQPGGSLRL SCAASGRTFS NYHMGWFRQA PGQGREFVAT IIRTGETIYY  60
ADSVKGRFTI SRDNSKNTLY LQMNSLRAED TAVYYCAAAT SGWNIKTVTP YEYWGQGTLV  120
TVSSESKYGP PCPPCPAPEV EGGPSVFLFP PKPKDTLMIS RTPEVTCVVV GVSQEDPEVQ  180
FNWYVDGVEV HNAKTKPREE QFNSTYRVVS VLQVLHVDWL NGKEYKCKVS NKGLPSSIEK  240
```

```
TISKAKGQPR EPQVYTLPPS QEEMTKNQVS LTCLVKGFYP SDIVVEWESN GQPENNYKTT  300
PPVLDSDGSF FLYSRLTVDK SRWQEGNVFS CSVMHEALHN HYTQKSLSLS LGK         353

SEQ ID NO: 5            moltype = AA  length = 353
FEATURE                 Location/Qualifiers
source                  1..353
                        mol_type = protein
                        organism = synthetic construct
SEQUENCE: 5
EVQLLESGGG LVQPGGSLRL SCAASGRTFS NYHMGWFRQA PGQGREFVAT IIRTGKTIYY  60
ADSVKGRFTI SRDNSKNTLY LQMNSLRAED TAVYYCAAAT SGWHIKTVTP YEYWGQGTLV  120
TVSSESKYGP PCPPCPAPEV EGGPSVFLFP PKPKDTLMIS RTPEVTCVVV GVSQEDPEVQ  180
FNWYVDGVEV HNAKTKPREE QFNSTYRVVS VLQVLHVDWL NGKEYKCKVS NKGLPSSIEK  240
TISKAKGQPR EPQVYTLPPS QEEMTKNQVS LTCLVKGFYP SDIVVEWESN GQPENNYKTT  300
PPVLDSDGSF FLYSRLTVDK SRWQEGNVFS CSVMHEALHN HYTQKSLSLS LGK         353

SEQ ID NO: 6            moltype = AA  length = 353
FEATURE                 Location/Qualifiers
source                  1..353
                        mol_type = protein
                        organism = synthetic construct
SEQUENCE: 6
EVQLLESGGG LVQPGGSLRL SCAASGRTFS NYHMGWFRQA PGQGREFVAT IIRTGTTIYY  60
ADSVKGRFTI SRDNSKNTLY LQMNSLRAED TAVYYCAAAT SGWHIKTVTP YEYWGQGTLV  120
TVSSESKYGP PCPPCPAPEV EGGPSVFLFP PKPKDTLMIS RTPEVTCVVV GVSQEDPEVQ  180
FNWYVDGVEV HNAKTKPREE QFNSTYRVVS VLQVLHVDWL NGKEYKCKVS NKGLPSSIEK  240
TISKAKGQPR EPQVYTLPPS QEEMTKNQVS LTCLVKGFYP SDIVVEWESN GQPENNYKTT  300
PPVLDSDGSF FLYSRLTVDK SRWQEGNVFS CSVMHEALHN HYTQKSLSLS LGK         353

SEQ ID NO: 7            moltype = AA  length = 353
FEATURE                 Location/Qualifiers
source                  1..353
                        mol_type = protein
                        organism = synthetic construct
SEQUENCE: 7
EVQLLESGGG LVQPGGSLRL SCAASGRTFS NYHMGWFRQA PGQGREFVAT IIRHGTTIYY  60
ADSVKGRFTI SRDNSKNTLY LQMNSLRAED TAVYYCAAAT SGWHIKTVTP YEYWGQGTLV  120
TVSSESKYGP PCPPCPAPEV EGGPSVFLFP PKPKDTLMIS RTPEVTCVVV GVSQEDPEVQ  180
FNWYVDGVEV HNAKTKPREE QFNSTYRVVS VLQVLHVDWL NGKEYKCKVS NKGLPSSIEK  240
TISKAKGQPR EPQVYTLPPS QEEMTKNQVS LTCLVKGFYP SDIVVEWESN GQPENNYKTT  300
PPVLDSDGSF FLYSRLTVDK SRWQEGNVFS CSVMHEALHN HYTQKSLSLS LGK         353

SEQ ID NO: 8            moltype = AA  length = 353
FEATURE                 Location/Qualifiers
source                  1..353
                        mol_type = protein
                        organism = synthetic construct
SEQUENCE: 8
EVQLLESGGG LVQPGGSLRL SCAASGRTFS NYHMGWFRQA PGQGREFVAT IIRTGETIYY  60
ADSVKGRFTI SRDNSKNTLY LQMNSLRAED TAVYYCAAAT SGWNIKTVTP YEYWGQGTLV  120
TVSSESKYGP PCPPCPAPEF LGGPSVFLFP PKPKDTLMIS RTPEVTCVVV DVSQEDPEVQ  180
FNWYVDGVEV HNAKTKPREE QFNSTYRVVS VLTVLHQDWL NGKEYKCKVS NKGLPSSIEK  240
TISKAKGQPR EPQVYTLPPS QEEMTKNQVS LTCLVKGFYP SDIAVEWESN GQPENNYKTT  300
PPVLDSDGSF FLYSRLTVDK SRWQEGNVFS CSVMHEALHN HYTQKSLSLS LGK         353

SEQ ID NO: 9            moltype = AA  length = 353
FEATURE                 Location/Qualifiers
source                  1..353
                        mol_type = protein
                        organism = synthetic construct
SEQUENCE: 9
EVQLLESGGG LVQPGGSLRL SCAASGRTFS NYHMGWFRQA PGQGREFVAT IIRTGTTIYY  60
ADSVKGRFTI SRDNSKNTLY LQMNSLRAED TAVYYCAAAT SGWHIKTVTP YEYWGQGTLV  120
TVSSESKYGP PCPPCPAPEF LGGPSVFLFP PKPKDTLMIS RTPEVTCVVV DVSQEDPEVQ  180
FNWYVDGVEV HNAKTKPREE QFNSTYRVVS VLTVLHQDWL NGKEYKCKVS NKGLPSSIEK  240
TISKAKGQPR EPQVYTLPPS QEEMTKNQVS LTCLVKGFYP SDIAVEWESN GQPENNYKTT  300
PPVLDSDGSF FLYSRLTVDK SRWQEGNVFS CSVMHEALHN HYTQKSLSLS LGK         353

SEQ ID NO: 10           moltype = AA  length = 124
FEATURE                 Location/Qualifiers
source                  1..124
                        mol_type = protein
                        organism = synthetic construct
SEQUENCE: 10
EVQLLESGGG LVQPGGSLRL SCAASGRTFS NYHMGWFRQA PGQGREFVAT IIRTGETIYY  60
ADSVKGRFTI SRDNSKNTLY LQMNSLRAED TAVYYCAAAT SGWNIKTVTP YEYWGQGTLV  120
TVSS                                                               124

SEQ ID NO: 11           moltype = AA  length = 124
```

```
FEATURE                Location/Qualifiers
source                 1..124
                       mol_type = protein
                       organism = synthetic construct
SEQUENCE: 11
EVQLLESGGG LVQPGGSLRL SCAASGRTFS NYHMGWFRQA PGQGREFVAT IIRTGKTIYY  60
ADSVKGRFTI SRDNSKNTLY LQMNSLRAED TAVYYCAAAT SGWHIKTVTP YEYWGQGTLV  120
TVSS                                                               124

SEQ ID NO: 12          moltype = AA  length = 124
FEATURE                Location/Qualifiers
source                 1..124
                       mol_type = protein
                       organism = synthetic construct
SEQUENCE: 12
EVQLLESGGG LVQPGGSLRL SCAASGRTFS NYHMGWFRQA PGQGREFVAT IIRTGTTIYY  60
ADSVKGRFTI SRDNSKNTLY LQMNSLRAED TAVYYCAAAT SGWHIKTVTP YEYWGQGTLV  120
TVSS                                                               124

SEQ ID NO: 13          moltype = AA  length = 124
FEATURE                Location/Qualifiers
source                 1..124
                       mol_type = protein
                       organism = synthetic construct
SEQUENCE: 13
EVQLLESGGG LVQPGGSLRL SCAASGRTFS NYHMGWFRQA PGQGREFVAT IIRHGTTIYY  60
ADSVKGRFTI SRDNSKNTLY LQMNSLRAED TAVYYCAAAT SGWHIKTVTP YEYWGQGTLV  120
TVSS                                                               124

SEQ ID NO: 14          moltype = AA  length = 229
FEATURE                Location/Qualifiers
source                 1..229
                       mol_type = protein
                       organism = unidentified
SEQUENCE: 14
ESKYGPPCPP CPAPEVEGGP SVFLFPPKPK DTLMISRTPE VTCVVVGVSQ EDPEVQFNWY  60
VDGVEVHNAK TKPREEQFNS TYRVVSVLQV LHVDWLNGKE YKCKVSNKGL PSSIEKTISK  120
AKGQPREPQV YTLPPSQEEM TKNQVSLTCL VKGFYPSDIV VEWESNGQPE NNYKTTPPVL  180
DSDGSFFLYS RLTVDKSRWQ EGNVFSCSVM HEALHNHYTQ KSLSLSLGK             229

SEQ ID NO: 15          moltype = AA  length = 229
FEATURE                Location/Qualifiers
source                 1..229
                       mol_type = protein
                       organism = synthetic construct
SEQUENCE: 15
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK             229

SEQ ID NO: 16          moltype = AA  length = 5
FEATURE                Location/Qualifiers
source                 1..5
                       mol_type = protein
                       organism = synthetic construct
SEQUENCE: 16
NYHMG                                                              5

SEQ ID NO: 17          moltype = AA  length = 17
FEATURE                Location/Qualifiers
source                 1..17
                       mol_type = protein
                       organism = synthetic construct
SEQUENCE: 17
TIIRTGETIY YADSVKG                                                 17

SEQ ID NO: 18          moltype = AA  length = 15
FEATURE                Location/Qualifiers
source                 1..15
                       mol_type = protein
                       organism = synthetic construct
SEQUENCE: 18
ATSGWNIKTV TPYEY                                                   15

SEQ ID NO: 19          moltype = AA  length = 7
FEATURE                Location/Qualifiers
source                 1..7
                       mol_type = protein
```

```
                      organism = synthetic construct
SEQUENCE: 19
GRTFSNY                                                                   7

SEQ ID NO: 20         moltype = AA  length = 6
FEATURE               Location/Qualifiers
source                1..6
                      mol_type = protein
                      organism = synthetic construct
SEQUENCE: 20
IRTGET                                                                    6

SEQ ID NO: 21         moltype = AA  length = 17
FEATURE               Location/Qualifiers
source                1..17
                      mol_type = protein
                      organism = synthetic construct
SEQUENCE: 21
TIIRTGKTIY YADSVKG                                                        17

SEQ ID NO: 22         moltype = AA  length = 15
FEATURE               Location/Qualifiers
source                1..15
                      mol_type = protein
                      organism = synthetic construct
SEQUENCE: 22
ATSGWHIKTV TPYEY                                                          15

SEQ ID NO: 23         moltype = AA  length = 6
FEATURE               Location/Qualifiers
source                1..6
                      mol_type = protein
                      organism = synthetic construct
SEQUENCE: 23
IRTGKT                                                                    6

SEQ ID NO: 24         moltype = AA  length = 17
FEATURE               Location/Qualifiers
source                1..17
                      mol_type = protein
                      organism = synthetic construct
SEQUENCE: 24
TIIRTGTTIY YADSVKG                                                        17

SEQ ID NO: 25         moltype = AA  length = 6
FEATURE               Location/Qualifiers
source                1..6
                      mol_type = protein
                      organism = synthetic construct
SEQUENCE: 25
IRTGTT                                                                    6

SEQ ID NO: 26         moltype = AA  length = 17
FEATURE               Location/Qualifiers
source                1..17
                      mol_type = protein
                      organism = synthetic construct
SEQUENCE: 26
TIIRHGTTIY YADSVKG                                                        17

SEQ ID NO: 27         moltype = AA  length = 6
FEATURE               Location/Qualifiers
source                1..6
                      mol_type = protein
                      organism = synthetic construct
SEQUENCE: 27
IRHGTT                                                                    6
```

The invention claimed is:

1. An antibody or antigen binding fragment thereof that binds to C3b comprising three complementarity determining regions (CDR1 to CDR3, respectively), wherein

```
a)
the CDR1 comprises
                              (SEQ ID NO: 16)
NYHMG,

CDR2 comprises
                              (SEQ ID NO: 17)
TIIRTGETIYYADSVKG
and

CDR3 comprises
                              (SEQ ID NO: 18)
ATSGWNIKTVTPYEY;

b)
the CDR1 comprises
                              (SEQ ID NO: 19)
GRTFSNY,

CDR2 comprises
                              (SEQ ID NO: 20)
IRTGET
and

CDR3 comprises
                              (SEQ ID NO: 18)
ATSGWNIKTVTPYEY;

c)
the CDR1 comprises
                              (SEQ ID NO: 16)
NYHMG,

CDR2 comprises
                              (SEQ ID NO: 26)
TIIRHGTTIYYADSVKG
and

CDR3 comprises
                              (SEQ ID NO: 22)
ATSGWHIKTVTPYEY;

d)
the CDR1 comprises
                              (SEQ ID NO: 19)
GRTFSNY,

CDR2 comprises
                              (SEQ ID NO: 27)
IRHGTT
and

CDR3 comprises
                              (SEQ ID NO: 22)
ATSGWHIKTVTPYEY;

e)
the CDR1 comprises
                              (SEQ ID NO: 16)
NYHMG,

CDR2 comprises
                              (SEQ ID NO: 21)
TIIRTGKTIYYADSVKG
and

CDR3 comprises
                              (SEQ ID NO: 22)
ATSGWHIKTVTPYEY;

f)
the CDR1 comprises
                              (SEQ ID NO: 19)
GRTFSNY,
```

-continued

```
CDR2 comprises
                              (SEQ ID NO: 23)
IRTGKT
and

CDR3 comprises
                              (SEQ ID NO: 22)
ATSGWHIKTVTPYEY;

g)
the CDR1 comprises
                              (SEQ ID NO: 16)
NYHMG,

CDR2 comprises
                              (SEQ ID NO: 24)
TIIRTGTTIYYADSVKG
and

CDR3 comprises
                              (SEQ ID NO: 22)
ATSGWHIKTVTPYEY;
or

h)
the CDR1 comprises
                              (SEQ ID NO: 19)
GRTFSNY,

CDR2 comprises
                              (SEQ ID NO: 25)
IRTGTT
and

CDR3 comprises
                              (SEQ ID NO: 22)
ATSGWHIKTVTPYEY.
```

2. The antibody or antigen binding fragment thereof of claim 1, comprising an amino acid sequence at least 90% identical to any of SEQ ID NOs: 10-13, wherein any differences relative to SEQ ID NOs: 10-13 do not occur in CDRs 1-3.

3. The antibody or antigen binding fragment thereof of claim 1, wherein the antibody or antigen binding fragment thereof is a VHH.

4. The antibody or antigen binding fragment thereof of claim 1, further comprising an Fc domain, wherein the Fc domain is derived from IgG1, IgG2, IgG3, or IgG4.

5. The antibody or antigen binding fragment thereof of claim 1, wherein the antibody or a fragment thereof inhibits formation of C3 convertase and/or C5 convertase.

6. The antibody or antigen binding fragment thereof of claim 1, wherein the antibody or a fragment thereof does not bind to C3 protein.

7. The antibody or antigen binding fragment thereof of claim 1, wherein the antibody or a fragment thereof inhibits the activity of C3 convertase.

8. The antibody or antigen binding fragment thereof of claim 1, comprising an amino acid sequence at least 90% identical to any one of SEQ ID NOs: 4-9, wherein any differences relative to SEQ ID NOs: 4-9 do not occur in CDRs 1-3.

9. The antibody or antigen binding fragment thereof of claim 8, comprising any one of SEQ ID NOs: 4-9.

10. An isolated nucleic acid encoding the antibody or antigen binding fragment thereof of claim 1.

11. A composition comprising the nucleic acid of claim 10, and a delivery vehicle.

12. The composition of claim 11, wherein the delivery vehicle is an adeno-associated virus (AAV) vector or a lipid nanoparticle (LNP).

13. The antibody or antigen binding fragment thereof of claim 2, comprising any one of SEQ ID NOs: 10-13.

14. The antibody or antigen binding fragment thereof of claim 4, wherein the Fc domain is derived from IgG4.

15. The antibody or antigen binding fragment thereof of claim 14, wherein the Fc domain is modified.

16. The antibody or antigen binding fragment thereof of claim 15, wherein the Fc domain comprises T307Q, Q311V, and/or A378V mutations, wherein the Fc domain is numbered according to the EU index.

17. The antibody or antigen binding fragment thereof of claim 15, wherein the Fc domain comprises S228P mutation, wherein the Fc domain is numbered according to the EU index.

18. The antibody or antigen binding fragment thereof of claim 15, wherein the Fc domain comprises F234, L235, and/or D265 mutations, wherein the Fc domain is numbered according to the EU index.

19. The antibody or antigen binding fragment thereof of claim 15, wherein the Fc domain comprises S228P, F234V, L235E, D265G, T307Q, Q311V, and A378V mutations, wherein the Fc domain is numbered according to the EU index.

20. The antibody or antigen binding fragment thereof of claim 19, wherein the Fc domain comprises an amino acid sequence of SEQ ID NO: 14.

21. An antibody or antigen binding fragment thereof that binds to C3b comprising three complementarity determining regions (CDR1 to CDR3, respectively), wherein the CDR1 comprises NYHMG (SEQ ID NO: 16), CDR2 comprises TIIRTGETIYYADSVKG (SEQ ID NO: 17) and CDR3 comprises ATSGWNIKTVTPYEY (SEQ ID NO: 18).

22. An antibody or antigen binding fragment thereof that binds to C3b comprising three complementarity determining regions (CDR1 to CDR3, respectively), wherein the CDR1 comprises NYHMG (SEQ ID NO: 16), CDR2 comprises TIIRHGTTIYYADSVKG (SEQ ID NO: 26) and CDR3 comprises ATSGWHIKTVTPYEY (SEQ ID NO: 22).

23. An antibody or antigen binding fragment thereof that binds to C3b comprising three complementarity determining regions (CDR1 to CDR3, respectively), wherein the CDR1 comprises NYHMG (SEQ ID NO: 16), CDR2 comprises TIIRTGTTIYYADSVKG (SEQ ID NO: 24) and CDR3 comprises ATSGWHIKTVTPYEY (SEQ ID NO: 22).

24. The antibody or antigen binding fragment thereof of claim 21, comprising the amino acid sequence of SEQ ID NO: 10.

25. The antibody or antigen binding fragment thereof of claim 22, comprising the amino acid sequence of SEQ ID NO: 13.

26. The antibody or antigen binding fragment thereof of claim 23, comprising the amino acid sequence of SEQ ID NO: 12.

* * * * *